United States Patent
Sternson et al.

(10) Patent No.: US 11,124,554 B2
(45) Date of Patent: *Sep. 21, 2021

(54) MODIFIED LIGAND-GATED ION CHANNELS AND METHODS OF USE

(71) Applicant: Howard Hughes Medical Institute, Chevy Chase, MD (US)

(72) Inventors: Scott Sternson, Chevy Chase, MD (US); Peter Lee, Chevy Chase, MD (US); Christopher Magnus, Chevy Chase, MD (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/868,205

(22) Filed: May 6, 2020

(65) Prior Publication Data

US 2020/0377566 A1 Dec. 3, 2020

Related U.S. Application Data

(63) Continuation of application No. 15/644,295, filed on Jul. 7, 2017.

(60) Provisional application No. 62/359,534, filed on Jul. 7, 2016, provisional application No. 62/486,779, filed on Apr. 18, 2017.

(51) Int. Cl.

| C07K 14/705 | (2006.01) |
| C07K 19/00 | (2006.01) |
| C07K 14/47 | (2006.01) |
| A61K 38/01 | (2006.01) |
| A61K 38/17 | (2006.01) |
| C12N 15/00 | (2006.01) |
| C12N 15/09 | (2006.01) |

(52) U.S. Cl.
CPC ........ *C07K 14/4713* (2013.01); *A61K 38/012* (2013.01); *A61K 38/1709* (2013.01); *C07K 14/4702* (2013.01); *C07K 14/705* (2013.01); *C07K 14/70571* (2013.01); *C12N 15/00* (2013.01); *C12N 15/09* (2013.01); *C07K 2319/00* (2013.01); *C07K 2319/03* (2013.01)

(58) Field of Classification Search
None
See application file for complete search history.

(56) References Cited

U.S. PATENT DOCUMENTS

| 7,186,870 | B2 | 3/2007 | Singer et al. |
| 8,435,762 | B2 | 5/2013 | Sternson et al. |
| 2005/0250808 | A1 | 11/2005 | Xie et al. |
| 2009/0048289 | A1 | 2/2009 | Tremel et al. |
| 2010/0130420 | A1 | 5/2010 | Sternson et al. |
| 2016/0069901 | A1 | 3/2016 | Laing et al. |
| 2018/0009862 | A1 | 1/2018 | Sternson et al. |
| 2019/0169264 | A1 | 6/2019 | Sternson |
| 2019/0375807 | A1 | 12/2019 | Sternson et al. |

FOREIGN PATENT DOCUMENTS

| WO | WO2010042799 | 4/2010 |
| WO | WO2011014679 | 2/2011 |

OTHER PUBLICATIONS

Craig et al., "Stable expression and characterisation of a human α7 nicotinic subunit chimera: a tool for functional high-throughput screening," European Journal of Pharmacology, Oct. 11, 2004, 502 (1-2): 31-40.

Grutter et al., "Molecular tuning of fast gating in pentameric ligand-gated ion channels," PNAS, Dec. 13, 2005, 102(50): 18207-18212.

Li et al., "Ligand-binding domain of an α7-nicotinic receptor chimera and its complex with agonist," Nat Neurosci., Nov. 5, 2012, 14(10): 1253-1259.

Young et al., "Potentiation of α7 nicotinic acetylcholine receptors via an allosteric transmembrane site," PNAS, Sep. 23, 2008, 105(38): 14686-14691.

Extended European Search Report in European Application No. 17824999.1, dated May 28, 2020, 16 pages.

Mazurov et al., "2-(Arylmethyl)-3-substituted quinuclidines as selective α7 nicotinic receptor ligands," Bioorganic & Medicinal Chemistry Letters, Pergamon, Amsterdam, NL, Apr. 15, 2005, vol. 15, No. 8, pp. 2073-2077, XP027801786.

Rucktooa et al., "Structural Characterization of Binding Mode of Smoking Cessation Drugs to Nicotinic Acetylcholine Receptors through Study of Ligand Complexes with Acetylcholine-binding Protein," Journal of Biological Chemistry, Jul. 6, 2012, vol. 287, No. 28, pp. 23283-23293, XP55073824.

Sadigh-Eteghad et al., "Selective activation of α7 nicotinic acetylcholine receptor by PHA-543613 improves Aβ25-35-mediated cognitive deficits in mice," Neuroscience, Jan. 1, 2015, vol. 298, pp. 81-93, XP029241092.

(Continued)

*Primary Examiner* — Joanne Hama
*Assistant Examiner* — Jon M Lockard
(74) *Attorney, Agent, or Firm* — Fish & Richardson P.C.

(57) ABSTRACT

This document relates to materials and methods for controlling ligand gated ion channel (LGIC) activity. For example, modified LGICs including at least one LGIC subunit having a modified ligand binding domain (LBD) and/or a modified ion pore domain (IPD) are provided. Also provided are exogenous LGIC ligands that can bind to and activate the modified LGIC, as well as methods of modulating ion transport across the membrane of a cell of a mammal, methods of modulating the excitability of a cell in a mammal, and methods of treating a mammal having a channelopathy.

7 Claims, 17 Drawing Sheets

Specification includes a Sequence Listing.

(56) References Cited

OTHER PUBLICATIONS

Teodoro et al., "A Promising PET Tracer for Imaging of α7 Nicotinic Acetylcholine Receptors in the Brain: Design, Synthesis, and in Vivo Evaluation of a Dibenzothiophene-Based Radioligand," Molecules, Oct. 9, 2015, vol. 20, No. 10, pp. 18387-18421, XP55695282.
Wang et al. "Stability of tramadol with three 5-HT3 receptor antagonists in polyolefin bags for patient-controlled delivery systems," Drug Design, Development and Therapy, Jun. 1, 2016, p. 1869, XP55695596.
Cappelli et al., "The interactions of the 5-HT$_3$ receptor with arylpiperazine, tropane, and quinuclidine ligands," Current Topics in Medicinal Chemistry, 2002, 2(6):599-624, 26 pages.
Celie et al., "Nicotine and Carbamycholine Binding to Nicotinic Acetylcholine Receptors as Studied in AChBP Crystal Structures," Mar. 25, 2004, Neuron, 41: 907-914, 8 pages.
Chenna et al., "Multiple sequence alignment with the Clustal series of programs," Jul. 2003, Nucleis Acids Res., 31(13):3497-3500, 4 pages.
Combrink et al., "Characterization of the naturally occurring Arg344His variant of the human 5-HT3A receptor," Oct. 2009, Pharmacological Reports, 61(5): 785-797, 13 pages.
Gao et al., "Derivaties of dibenzothiophene for positron emission tomography imaging of α7-nicotinic acetylcholine receptors," Journal of Medicinal Chemistry, 2013, 56(19):7574-7589, 16 pages.
International Search Report and Written Opinion in International Application No. PCT/US2017/041147, dated Oct. 18, 2017, 22 pages (with English translation).
PCT Invitation to Pay in International Application No. PCT/US2018/060109, dated Jan. 10, 2019, 4 pages.
Price et al., "Varenicline interactions at the 5-HT3 receptor ligand binding site are revealed by 5-HTBP," ACS Chemical Neuroscience, 2015, 6 (7): 1151-1157, 7 pages.
Walker et al., "Design, synthesis, structure-activity relationship, and in vivo activity of azabicyclic aryl amides as alpha7 nicotinic acetylcholine receptor agonists," Bioorg Med Chem., Dec. 2006, 14(24):8219-48, 30 pages.
Wishka et al., "Discovery of N-[(3R)-1-azabicyclo [2.2.2]oct-3-yl]furo[2,3-c]pyridine-5-carboxamide, an agonist of the alpha7 nicotinic acetylcholine receptor, for the potential treatment of cognitive deficits in schizophrenia: synthesis and structure—activity relationship," J Med Chem., Jul. 2006, 49(14):4425-36, 12 pages.
PCT International Search Report and Written Opinion in International Appln. No. PCT/US2018/060109, dated Feb. 28, 2019.
Magnus et al. "Chemical and genetic engineering of selective ligand-ion channel interactions," Science, Sep. 2, 2011 (Sep. 2, 2011), vol. 333, Iss. 6047, pp. 1291-1296. Entire document.
Wells, J.A, "Additivity of mutational effects in proteins. Biochemistry," 1990, 29(37):8509-8517.
Ngo et al., "Computational complexity, protein structure prediction, and the Levinthal paradox. In Merz and Le Grand (Eds.) The Protein Folding Problem and Tertiary Structure Prediction. Birkhauser:Boston," 1994, pp. 491-495.
Galzi et al., "Functional significance of aromatic amino acids from three peptide loops of the α7 neuronal nicotinic receptor site investigated by site-directed mutagenesis," FEBS, Elsevier Science Publishers B.V., Dec. 1991, vol. 294, No. 3, pp. 198-202.

Signal Peptide 1-22

MRCSPGGVWLALAASLLHVSLQGEFQRKLYKELVKNYNPLERPVANDSQP 50
────────── alpha7 nAChR LBD ──────────

LTVYFSLSLLQIMDVDEKNQVLTTNIWLQMSWTDHYLQWNVSEYPGVKTV 100
────────── alpha7 nAChR LBD ──────────

RFPDGQIWKPDILLYNSADERFDATFHTNVLVNSSGHCQYLPPGIFKSSC 150
────────── alpha7 nAChR LBD ──────────

YIDVRWFPFDVQHCKLKFGSWSYGGWSLDLQMQEADISGYIPNGEWDLVG 200
────────── alpha7 nAChR LBD ──────────

IPGKRSERFYECCKEPYPDVTFTVIIRRRPLFYAVSLLLPSIFLMVVDIV 250
────── alpha7 nAchR LBD ──┤ ────── 5HT3a IPD ──────

GFCLPPDSGERVSFKITLLLGYSVFLIIVSDTLPATIGTPLIGVYFVVCM 300
────────── 5HT3a IPD ──────────

ALLVISLAETIFIVRLVHKQDLQRPVPDWLRHLVLDRIAWILCLGEQPMA 350
────────── 5HT3a IPD ──────────

HRPPATEQANKTDDCSGSDLLPAMGNHCSHVGGPQDLEKTPRGRGSPLPP 400
────────── 5HT3a IPD ──────────

PREASLAVRGLLQELSSIRHFLEKRDEMREVARDWLRVGYVLDRLLFRIY 450
────────── 5HT3a IPD ──────────

LLAVLAYSITLVTLWSIWHYS.
────── 5HT3a IPD ──────

FIG. 1A

Signal Peptide 1-22

```
MRCSPGGVWLALAASLLHVSLQGEFQRKLYKELVKNYNPLERPVANDSQP   50
                      alpha7 nAChR LBD LTVYFSLSLLQIMDVDEKNQVLTTNIWLQMSWTDHYLQWNVSEYPGVKTV   100
                      alpha7 nAChR LBD RFPDGQIWKPDILLYNSADERFDATFHTNVLVNSSGHCQYLPPGIFKSSC   150
                      alpha7 nAChR LBD YIDVRWFPFDVQHCKLKFGSWSYGGWSLDLQMQEADISGYIPNGEWDLVG   200
                      alpha7 nAChR LBD IPGKRSERFYECCKEPYPDVTFTVTMRRMGYYLIQMYIPSLLIVILSWI    250
      alpha7 nAchR LBD              GlyR IPD SFWINMDAAPARVGLGITTVLTMTTQSSGSRASLPKVSYVKAIDIWMAVC   300
                          GlyR IPD LLFVFSALLEYAAVNFVSRQHKELLRFRRKRRHHKEDEAGEGRFNESAYG   350
                          GlyR IPD MGPACLQAKDGISVKGANNSNTTNPPPAPSKSPEEMRKLFIQRAKKIDKI   400
                          GlyR IPD SRIGFPMAFLIFNMFYWIIYKIVRREDVHNQ.
                GlyR IPD
```

FIG. 1B

Signal Peptide 1-22

```
MRCSPGGVWLALAASLLHVSLQGEFQRKLYKELVKNYNPLERPVANDSQP    50
─────────────── alpha7 nAChR LBD ───────────────

LTVYFSLSLLQIMDVDEKNQVLTTNIWLQMSWTDHYLQWNVSEYPGVKTV   100
─────────────── alpha7 nAChR LBD ───────────────

RFPDGQIWKPDILLYNSADERFDATFHTNVLVNSSGHCQYLPPGIFKSSC   150
─────────────── alpha7 nAChR LBD ───────────────

YIDVRWFPFDVQHCKLKFGSWSYGGWSLDLQMQEADISGYIPNGEWDLVG   200
─────────────── alpha7 nAChR LBD ───────────────

IPGKRSERFYECCKEPYPDVTFTVIRRRPLFYVVSLLLPSIFLMVMDIV    250
──────── alpha7 nAchR LBD ────────── 5HT3a IPD ─────

GFYLPPNSGERVSFKITLLLGYSVFLIIVSDTLPATAIGTPLIGVYFVVC   300
──────────────── 5HT3a IPD ────────────────

MALLVISLAETIFIVRLVHKQDLQQPVPAWLRHLVLERIAWLLCLREQST   350
──────────────── 5HT3a IPD ────────────────

SQRPPATSQATKTDDCSAMGNHCSHMGGPQDFEKSPRDRCSPPPPPREAS   400
──────────────── 5HT3a IPD ────────────────

LAVCGLLQELSSIRQFLEKRDEIREVARDWLRVGSVLDKLLFHIYLLAVL   450
──────────────── 5HT3a IPD ────────────────

AYSITLVMLWSIWQYA.
──── 5HT3a IPD ────
```

FIG. 1C signal peptide 1-22

```
MRCSPGGVWLALAASLLHVSLQGEFQRKLYKELVKNYNPLERPVANDSQP   50
                      ————— alpha7 nAChR LBD —————

LTVYFSLSLLQIMDVDEKNQVLTTNIWLQMSWTDHYLQWNVSEYPGVKTV  100
                      ————— alpha7 nAChR LBD —————

RFPDGQIWKPDILLYNSADERFDATFHTNVLVNSSGHCQYLPPGIFKSSC  150
                      ————— alpha7 nAChR LBD —————

YIDVRWFPFDVQHCKLKFGSWSYGGWSLDLQMQEADISGYIPNGEWDLVG  200
                      ————— alpha7 nAChR LBD —————

IPGKRSERFYECCKEPYPDVTFTVTMRRRTLYYLLQTYFPATLMVMLSWV  250
            —alpha7 nAchR LBD————  ——GABA C IPD———

SFWIDRRAVPARVPLGITTVLTMSTIITGVNASMPRVSYIKAVDIYLWVS  300
                      ————————— GABA C IPD —————————

FVFVFLSVLEYAAVNYLTTVQERKEQKLREKLPCTSGLPPPRTAMLDGNY  350
                      ————————— GABA C IPD —————————

SDGEVNDLDNYMPENGEKPDRMMVQLTLASERSSPQRKSQRSSYVSMRID  400
                      ————————— GABA C IPD —————————

THAIDKYSRIIFPAAYILFNLIYWSIFS.
      ————— GABA C IPD —————
```

FIG. 1D signal peptide 1-22

MGGGRGGIWLALAAALLHVSLQGEFQRRLYKELVKNYNPLERPVANDSQP 50

LTVYFSLSLLQIMDVDEKNQVLTTNIWLQMSWTDHYLQWNMSEYPGVKNV 100

RFPDGQIWKPDILLYNSADERFDATFHTNVGVNASGHCQYLPPGIFKSSC 150

YIDVRWFPFDVQQCKLKFGSWSYGGWSLDLQMQEADISSYIPNGEWDLMG 200

IPGKRNEKFYECCKEPYPDVTYTVTMRRRTLYYGLNLLIPCVLISALALL 250

VFLLPADSGEKISLGITVLLSLTTFMLLVAEIMPATSDSVPLIAQYFAST 300

MIIVGLSVVVTVIVLRYHHHDPDGGKMPKWTRIILLNWCAWFLRMKRPGE 350

DKVRPACQHKPRRCSLASVELSAGAGPPTSNGNLLYIGFRGLEGMHCAPT 400

PDSGVVCGRLACSPTHDEHLMHGAHPSDGDPDLAKILEEVRYIANRNRCQ 450

DESEVICSEWKFAACVVDPLCLMAFSVFTIICTIGILMSAPNFVEAVSKD 500

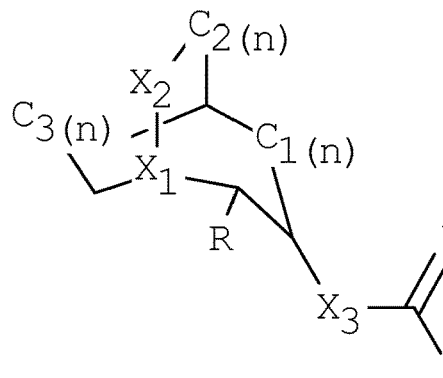

X = CH, CH$_2$, O, NH, NMe
n = 0 or 1
Y = O, S
A = Aromatic
R = Pyridinylmethylene

FIG. 5A

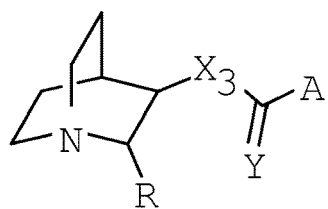
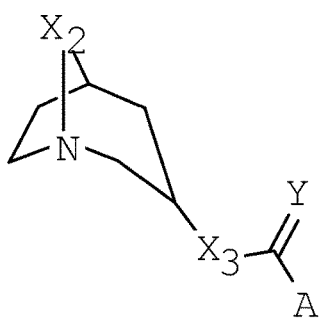
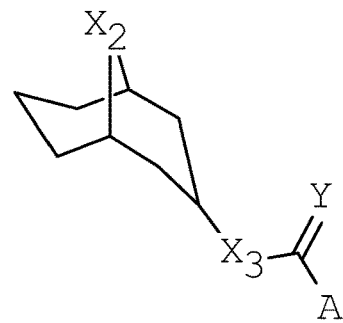

Pharmacophore: Quinuclidine $C_{1(n)}$ = 0
$C_{2(n)}$ = 1
$C_{3(n)}$ = 0
$X_1$ = N
$X_2$ = CH$_2$
$X_3$ = O, NH, CH$_2$
Y = O, S
A = Aromatic
R = Pyridinylmethylene Pharmacophore: Tropane $C_{1(n)}$ = 1
$C_{2(n)}$ = 0
$C_{3(n)}$ = 0
$X_1$ = CH
$X_2$ = NH, NMe
$X_3$ = O, NH, CH$_2$
Y = O, S
A = Aromatic Pharmacophore: 9-azabicyclo[3.3.1]nonane $C_{1(n)}$ = 1
$C_{2(n)}$ = 0
$C_{3(n)}$ = 1
$X_1$ = CH
$X_2$ = NH, NMe
$X_3$ = O, NH, CH$_2$
Y = O, S
A = Aromatic

FIG. 5B

MODIFIED LIGAND-GATED ION CHANNELS AND METHODS OF USE

CROSS-REFERENCE TO RELATED APPLICATIONS

This application is a Continuation of U.S. patent application Ser. No. 15/644,295, filed on Jul. 7, 2017, which claims the benefit of U.S. Patent Application Ser. No. 62/359,534, filed on Jul. 7, 2016, and claims the benefit of U.S. Patent Application Ser. No. 62/486,779, filed on Apr. 18, 2017. The disclosures of the prior applications are considered part of (and are incorporated by reference in) the disclosure of this application.

BACKGROUND

1. Technical Field

This document relates to materials and methods for controlling ligand gated ion channel (LGIC) activity. For example, this document provides modified LGICs including at least one LGIC subunit having a modified ligand binding domain (LBD) and/or a modified ion pore domain (IPD). Also provided are exogenous LGIC ligands that can bind to and activate the modified LGIC. In some cases, a modified LGIC and an exogenous ligand can be used to treat a mammal having a channelopathy (e.g., a neural channelopathy or a muscle channelopathy). In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

2. Background Information

Ion channels mediate ionic flux in cells, which profoundly affects their biological function. A prominent instance of this is in neurons, where ion channels control electrical signaling within between neurons to influence physiology, sensation, behavior, mood, and cognition.

Different LGICs have distinct ligand binding properties as well as specific ion conductance properties (Hille 2001 Ion Channels of Excitable Membranes. pp. 814. Sunderland, Mass.: Sinauer Associates; Kandel et al 2000 Principles of Neural Science. USA: McGraw-Hill Co. 1414 pp). For example, nicotinic acetylcholine receptors (nAChRs) bind the endogenous ligand acetylcholine (ACh), which activates conductances for cations and typically depolarizes cells, thereby increasing cellular excitability. In contrast, the glycine receptor (GlyR) binds the endogenous ligand glycine, which activates chloride anion conductance and typically reduces the excitability of cells by hyperpolarization and/or by an electrical shunt of the cellular membrane resistance.

SUMMARY

Levels of endogenous LGIC agonists such as ACh are not readily controlled.

This document provides materials and methods for controlling LGIC activity (e.g., increasing the sensitivity of LGICs to exogenous ligands and/or reducing sensitivity to endogenous ligands such as ACh). For example, this document provides modified LGICs including at least one modified LGIC subunit having a LBD and an IPD, and having at least one modified amino acid (e.g., an amino acid substitution). Also provided are exogenous LGIC ligands that can bind to and activate the modified LGIC. In some cases, a modified LGIC and an exogenous ligand can be used to treat a mammal having a channelopathy (e.g., a neural channelopathy or a muscle channelopathy). In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

Having the ability to control LGIC activity provides a unique and unrealized opportunity to achieve control of ion transport in cells. For example, modified LGICs having increased sensitivity for one or more exogenous LGIC ligands can be used to provide temporal and spatial control of ion transport and/or cellular excitability based on delivery of the exogenous LGIC ligand. For example, modified LGICs with reduced sensitivity for endogenous LGIC ligands prevent unwanted activation of modified LGICs and allow for selective control over the modified LGIC by exogenous ligands. Further, exogenous LGIC ligands having increased potency for a modified LGIC improve selectivity of targeting of the modified LGIC over endogenous ion channels. Thus, the modified LCIGs and exogenous LGIC ligands provided herein are useful to achieve a therapeutic effect while reducing side effects from the small molecules on unintended targets.

As described herein, one or more mutations in a modified LGIC can enhance potency for exogenous LGIC ligands. Mutation of the α7 LBD of α7-GlyR at residue L131 (e.g., substituting Leu with Gly or Ala) increased potency for varenicline (16-fold) and tropisetron (3.6-fold) while reducing ACh potency (−6.4-fold) relative to α7-GlyR. Mutation of α7 LBD of α7-GlyR at residue G175 (e.g., G175K) or P216 (e.g., P216I) enhanced potency for ACh, nicotine, tropisetron, varenicline, as well as other quinuclidine and tropane agonists. Combining the mutation at residue G175K with mutations that reduce potency of the endogenous agonist ACh (e.g. Y115F) produced α7-GlyR Y115F G175K with increased potency for tropisetron (5.5-fold) and reduced potency from ACh (−8-fold). In addition, combining mutations in the α7 LBD at residues 77 (e.g., substituting Trp with Phe or Tyr) and/or 79 (e.g., substituting Gln with Gly, Ala, or Ser) and/or 131 (e.g., substituting Leu with Gly or Ala) and/or 141 (e.g., substituting Leu with Phe or Pro) in these chimeric channels with potency enhancing mutations at residues G175 (e.g., G175K) or P216 (e.g., P216I) increase potency for distinct ligands and/or reduce ACh potency. For example, a chimeric α7-GlyR LGIC with a α7 nAChR LBD (α7 LBD) having a mutation at residue 79 (e.g., substituting Gln with Gly), a mutation at residue 115 (e.g., substituting Tyr with Phe), and a mutation at residue 175 (e.g., substituting Gly with Lys) has greater than 100-fold increased sensitivity to an exogenous tropane LGIC ligand compound 723 (a tropane), and reduced ACh sensitivity (−15-fold) relative to the unmodified chimeric α7-GlyR LGIC. Furthermore, a modified LGIC including at least one chimeric LGIC subunit having an α7 nAChR LBD (α7 LBD) having a mutation at residue 79 (e.g., substituting Gln with Ala, Gly, or Ser) and a GlyR IPD having a mutation at residue 298 (e.g., substituting Ala with Gly) has nearly 20-fold increased sensitivity for an exogenous LGIC ligand, such as a quinuclidine or a tropane. Additional mutations at residue 27 (e.g., substituting Arg with Asp) and 41 (e.g., substituting Glu with Arg) of the α7 LBD reduced the association of the modified chimeric LGIC with an unmodified ion channels. Additional mutations at residue 115 (e.g., substituting Tyr with Phe), 139 (e.g., substituting Gln with Gly or Leu), 210 (e.g., substituting Tyr with Phe) 217 (e.g., substituting Tyr with Phe), and/or 219 (e.g., substituting Asp with Ala) of the α7 LBD reduced sensitivity of the chimeric LGIC to the endogenous ligand ACh. These chimeric LGICs allow for highly selective control over cellular function in cells of a mammal while minimizing cross-reactivity with endogenous signaling systems in the mammal.

In general, one aspect of this document features a modified LGIC having at least one modified LGIC subunit which includes a LBD having an amino acid modification, and an IPD, where an exogenous LGIC ligand activates the modified LGIC. The modified LGIC can be a chimeric LGIC having a LBD from a first LGIC and an IPD from a second LGIC. The LBD can be an alpha7 nicotinic acetylcholine receptor (α7-nAChR) LBD. The modified LGIC of claim 3, wherein the at least one modified amino acid in the α7-nAChR LBD comprises an amino acid substitution at an amino acid residue selected from the group consisting of residues 77, 79, 131, 139, 141, 175, and 216 of the α7-nAChR LBD. The amino acid substitution can be at residue 79 of the α7 LBD, and the amino acid substitution can be Q79A, Q79G or Q79S. For example, the amino acid substitution at residue 79 of the α7 LBD can be Q79G The IPD can be a serotonin 3 receptor (5HT3) IPD, a glycine receptor (GlyR) IPD, a gamma-aminobutyric acid (GABA) receptor IPD, or an α7-nAChR IPD. The IPD can be a GlyR IPD, and the GlyR IPD can include an amino acid substitution at residue 298 (e.g., a A298G substitution) of the chimeric LGIC. The IPD can be a GABA IPD, and the GABA IPD can include an amino acid substitution at residue 298 (e.g., a W298A substitution) of the modified LGIC. The modified LGIC can be a chimeric LGIC including an α7 LBD having a Q79G amino acid substitution, and a GlyR IPD having a A298G amino acid substitution. The exogenous LGIC ligand can be a synthetic exogenous LGIC ligand selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane. When the synthetic exogenous LGIC ligand is a tropane, the tropane can be tropisetron, pseudo-tropisetron, nortropisetron, compound 723, compound 725, compound 737, or compound 745. When the synthetic exogenous LGIC ligand is a quinuclidine, the quinuclidine can be PNU-282987, PHA-543613, compound 0456, compound 0434, compound 0436, compound 0354, compound 0353, compound 0295, compound 0296, compound 0536, compound 0676, or compound 702. When the synthetic exogenous LGIC ligand is a 6,7,8,9-tetrahydro-6,10-methano-6H-pyrazino(2,3-h)benzazepine, the ligand can be compound 765 or compound 770. When the synthetic exogenous LGIC ligand is a 1,4-diazabicyclo[3.2.2]nonane, the ligand can be compound 773 or compound 774. In some cases, the LBD can be an α7 LBD, and the α7 LBD can also include at least one modified amino acid that confers selective binding to another α7 LBD having the at least one modified amino acid over binding to an unmodified LGIC. The unmodified LGIC can be an endogenous LGIC (e.g., an endogenous α7-nAChR). The at least one modified amino acid in the α7 LBD that confers reduced binding to the unmodified LGIC can include an amino acid substitution at residue 27 (e.g., a R27D substitution) and/or residue 41 (e.g., an E41R substitution). In some cases, the IPD can be a 5HT3 IPD, and the 5HT3 IPD can include at least one modified amino acid that confers increased ion conductance to the modified LGIC. The at least one modified amino acid in the 5HT3 IPD that confers increased ion conductance to the modified LGIC can include an amino acid substitution at an amino acid residue at residue 425 (e.g., a R425Q substitution), 429 (e.g., a R429D substitution), and/or 433 (e.g., a R433A substitution).

In another aspect, this document features a modified LGIC having at least one modified LGIC subunit including a LBD having at least one modified amino acid, and an IPD, where the at least one modified amino acid in the LBD reduces binding with an endogenous LGIC ligand. The modified LGIC can be a chimeric LGIC having a LBD from a first LGIC and an IPD from a second LGIC. The endogenous LGIC ligand can be ACh. The modified LGIC can have an EC50 of greater than 20 μM for Ach. The at least one modified amino acid can include an amino acid substitution at residue 115, 139, 210, 217, and/or 219. When the at least one modified amino acid includes an amino acid substitution at residue 115, the amino acid substitution can be a Y115F substitution. When the at least one modified amino acid includes an amino acid substitution at residue 139, the amino acid substitution can be a Q139G or a Q139L substitution. When the at least one modified amino acid includes an amino acid substitution at residue 210, the amino acid substitution can be a Y210F substitution. When the at least one modified amino acid includes an amino acid substitution at residue 217, the amino acid substitution can be a Y217F substitution. When the at least one modified amino acid includes an amino acid substitution at residue 219, the amino acid substitution can be a D219A substitution.

In another aspect, this document features a ligand having increased potency for a modified ligand gated ion channel (LGIC), wherein the ligand comprises Formula I:

$$\begin{array}{c} C_{2(n)} \\ | \\ C_{3(n)} - X_2 \\ | \\ X_1 - C_{1(n)} \\ | \quad \quad \quad Y \\ R \quad \quad X_3 \diagdown A \end{array}$$

where each of X1, X2, and X3 can independently be CH, CH2, O, NH, or NMe; where each n can independently be 0 or 1; where Y=O or S; where A=an aromatic substituent; and where R=H or pyridinylmethylene. The aromatic substituent can be 1H-indole, 4-(trifluoromethyl) benzene, 2,5-dimethoxy benzene, 4-chloroaniline, aniline, 5-(trifluoromethyl) pyridin-2-yl, 6-(trifluoromethyl) nicotinic, or 4-chloro-benzene.

In some cases, a LGIC ligand can be a quinuclidine and can have a structure shown in Formula II:

$$\begin{array}{c} \diagup N \diagdown \quad X_3 \diagdown A \\ \quad \quad R \quad Y \end{array}$$

where X3=O, NH, or CH2; where Y=O or S; where A=an aromatic substituent; and where R=H or pyridinylmethylene. The aromatic substituent can be 1H-indole, 4-(trifluoromethyl) benzene, 4-chloro benzene, 2,5-dimethoxy benzene, 4-(trifluoromethyl) benzene, 4-chloroaniline, aniline, 5-(trifluoromethyl) pyridin-2-yl, 6-(trifluoromethyl) nicotinic, 3-chloro-4-fluoro benzene, or 1H-indole. The quinuclidine can be PNU-282987, PHA-543613, compound 0456, compound 0434, compound 0436, compound 0354, compound 0353, compound 0295, compound 0296, compound 0536, compound 0676, or compound 702.

In some cases, a LGIC ligand can be a tropane and can have a structure shown in Formula III:

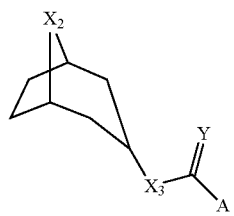

where X2=NH or NMe; where X3=O, NH, or CH2; where Y=O or S; and where A=an aromatic substituent. The aromatic substituent can be 1H-indole, 7-methoxy-1H-indole, 7-methyl-1H-indole, 5-chloro-1H-indole, or 1H-indazole. The tropane can be tropisetron, pseudo-tropisetron, nortropisetron, compound 723, compound 725, compound 737, or compound 745.

In some cases, a LGIC ligand can be a 9-azabicyclo[3.3.1]nonane and can have a structure shown in Formula IV:

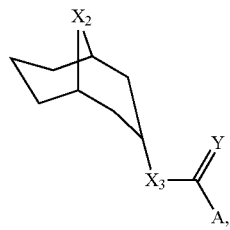

where X1 can be CH, X2 can be NH or NMe, X3 can be O, NH, or CH; Y can be O or S, and A can be an aromatic substituent. The aromatic substituent can be 4-chloro-benzene. The 9-azabicyclo[3.3.1]nonane can be compound 0536.

In another aspect, this document features a ligand having increased potency for a modified ligand gated ion channel (LGIC), where the ligand can be a 6,7,8,9-tetrahydro-6,10-methano-6H-pyrazino(2,3-h)benzazepine and have a structure shown in Formula V:

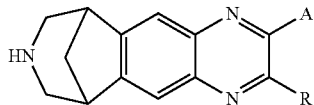

where R can be H or CH3, and where A can be H or an aromatic substituent. The 6,7,8,9-tetrahydro-6,10-methano-6H-pyrazino(2,3-h)benzazepine can be varenicline, compound 0765, or compound 0770.

In another aspect, this document features a ligand having increased potency for a modified ligand gated ion channel (LGIC), where the ligand can be a 1,4-diazabicyclo[3.2.2]nonane and can have a structure shown in Formula VI:

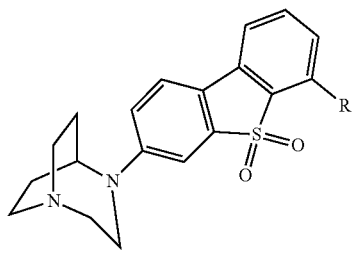

where R can be H, F, or NO2. The 1,4-diazabicyclo[3.2.2]nonane can be 3-(1,4-diazabicyclo[3.2.2]nonan-4-yl)dibenzo[b,d]thiophene 5,5-dioxide, compound 0773, or compound 0774.

In another aspect, this document features methods of treating a channelopathy in a mammal. The methods include, or consist essentially of, administering to a cell in the mammal a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The channelopathy can be Bartter syndrome, Brugada syndrome, catecholaminergic polymorphic ventricular tachycardia (CPVT), congenital hyperinsulinism, cystic fibrosis, Dravet syndrome, episodic ataxia, erythromelalgia, generalized epilepsy (e.g., with febrile seizures), familial hemiplegic migraine, fibromyalgia, hyperkalemic periodic paralysis, hypokalemic periodic paralysis, Lambert-Eaton myasthenic syndrome, long QT syndrome (e.g., Romano-Ward syndrome), short QT syndrome, malignant hyperthermia, mucolipidosis type IV, myasthenia gravis, myotonia congenital, neuromyelitis optica, neuromyotonia, nonsyndromic deafness, paramyotonia congenital, retinitis pigmentosa, timothy syndrome, tinnitus, seizure, trigeminal neuralgia, or multiple sclerosis.

In another aspect, this document features methods of modulating ion transport across a cell membrane of a mammal. The methods include, or consist essentially of, administering to the cell a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include activating or inhibiting ion transport. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid encoding the modified LGIC.

In another aspect, this document features methods of modulating the excitability of a cell in a mammal. The methods include, or consist essentially of, administering to the cell from the mammal a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include increasing the excitability of the cell or decreasing the excitability of the cell. The cell can be an excitable cell. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid encoding the modified LGIC.

In another aspect, this document features methods of modulating the activity of a cell in a mammal. The methods include, or consist essentially of, administering to the cell a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include increasing the activity of the cell or decreasing the activity of the cell. The activity can be ion transport, passive transport, excitation, inhibition, or exocytosis. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid (e.g., via a viral vector such as an adeno-associated virus, a herpes simplex virus, or a lentivirus) encoding the modified LGIC.

In another aspect, this document features a method for identifying a ligand that selectively binds to a modified LGIC. The method includes, or consists essentially of, providing one or more candidate ligands to the modified LGIC described herein, and detecting binding between the candidate ligand and the modified LGIC, thereby identifying a ligand that selectively binds the modified LGIC. The modified LGIC can be a homomeric modified LGIC.

In another aspect, this document features a method for detecting a modified LGIC. The method includes, or consists essentially of, providing one or more modified LGIC subunits described herein, providing an agent that selectively binds the modified LGIC, and detecting binding between the modified LGIC and the agent that selectively binds the modified LGIC, thereby detecting the modified LGIC. The agent that selectively binds the modified LGIC comprises can be antibody, a protein (e.g., bungarotoxin), or a small molecule (e.g., a positron emission tomography (PET) ligand). The agent that selectively binds the modified LGIC can include a detectable label (e.g., a fluorescent label, a radioactive label, or a positron emitting label).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1E show exemplary amino acid sequences of chimeric LGICs. Mutation of amino acid residue 77 (e.g., W77F or W77Y) resulted in sensitivity to granisetron and tropisetron. Mutation of amino acid residue 79 (e.g., Q79G) was most effective for several agonists. Mutations of amino acid residue 131 (e.g., L131G, L131A, L131M, or L131N) altered sensitivity to varenicline, tropisetron, granisetron, and ACh. Potency was considerably enhanced when LBD mutations were combined with mutation at amino acid residue 298 in the GlyR or GABAC IPD. Potency was also enhanced when α7 nAChR LBD mutations were combined with mutation at amino acid residue G175 and P216. FIG. 1A) An amino acid sequence of α7-5HT3 chimeric receptor (SEQ ID NO:6) including a human α7 nAChR LBD (SEQ ID NO:1) and a murine 5HT3 IPD (SEQ ID NO:3) components. FIG. 1B) An amino acid sequence of α7-GlyR chimeric receptor (SEQ ID NO:7), including a human α7 nAChR LBD (SEQ ID NO:2) and a human GlyR IPD (SEQ ID NO:5) components. FIG. 1C) An amino acid sequence of α7-5HT3 chimeric receptor (SEQ ID NO:8) including human α7 nAChR LBD (SEQ ID NO:1) and a human 5HT3 IPD (SEQ ID NO:4) components. FIG. 1D) An amino acid sequence of α7-GABAc chimeric receptor (SEQ ID NO:10) including a human α7 nAChR LBD (SEQ ID NO:2) and a human GABAc IPD (SEQ ID NO:9) components. FIG. 1E) An amino acid sequence of rat nAChR sequence (SEQ ID NO:12).

FIG. 3A) A graph of EC50s normalized to the unmodified α7-5HT3 chimeric channel (log scale). *P<0.05, statistically significant potency changes are noted (ANOVA followed by Dunn's test). FIG. 3B) Chemical structures of known nAChR agonists.

FIG. 4A) A graph of EC50s for Q79 LBD mutants normalized to the unmodified α7-GlyR chimeric channel (log scale). FIG. 4B) A graph of EC50s for A298G IPD mutation normalized to the unmodified α7-GlyR chimeric channel (log scale). FIG. 4C) A graph of EC50s for α7-GlyR$^{A298}$G normalized to the unmodified α7-GlyR chimeric channel and compared to the double mutant channel α7Q79G-GlyR$^{A298G}$ (log scale). *P<0.05, statistically significant potency changes are noted (ANOVA followed by Dunn's test).

FIGS. 5A-5C show schematic structures of LGIC agonists with substitution patterns most compatible with potency enhancement for α7$^{Q79G}$-5HT3 and α7$^{Q79G}$-GlyR$^{A298G}$. FIG. 5A) A gener expressing α7$^{R27D,E41R}$-5HT3 with a V5 epitope tag shows potent responses to PNU-282987.

FIG. 8A) A graph of EC50s for Q79G G175K LBD mutants against known agonists normalized to the unmodified α7-GlyR chimeric channel (log scale). FIG. 8B) A graph of EC50s for ACh and tropisetron for channels with mutations in α7-GlyR chimeric LGICs. Mutations that result in channels with high potency for tropisetron and low potency for the endogenous ligand, acetylcholine (ACh) are optimal (grey shading). Unmod.: unmodified α7-GlyR chimeric LGIC. FIG. 8C) Action potentials of cortical neurons from a mouse brain transduced with α7$^{Q79G,Y115F,G175K}$-GlyR chimeric LGIC. Neurons fire in response to current injection (PRE) and are potently suppressed by 100 nM tropisetron. After washout (WASH) of tropisetron, neuron firing is restored FIG. 9A) A graph of EC50s for L131 LBD mutants against known agonists normalized to the unmodified α7-GlyR chimeric channel (log scale). FIG. 9B) A graph of EC50s for ACh and tropisetron for channels with mutations in α7$^{L131G}$-GlyR chimeric LGICs. FIG. 9C) A graphs showing mutations that result in channels with high potency for varenicline and low potency for the endogenous ligand, acetylcholine (ACh) are optimal (grey shading). Unmod.: unmodified α7-GlyR chimeric LGIC. FIG. 9D) Action potentials of a cortical neuron from a mouse brain transduced with α7$^{L131G,Q139L,Y217F}$-GlyR chimeric LGIC. Neuron fires in response to current injection (PRE) and are potently suppressed by 10 nM varenicline, even with >6-fold greater injected current. After washout (WASH) of tropisetron, neuron firing is restored.

FIG. 10A) Chemical structures of LGIC agonists with substitution patterns most compatible with potency enhancement for α7$^{Q79G,Y115F,G175K}$-GlyR. FIG. 10B) Chemical structures of LGIC agonists with substitution patterns most compatible with potency enhancement for α7$_{L131G,Q139L,Y217F}$-GlyR or α7$^{L131G,Q139L,Y217F}$-5HT3 HC.

DETAILED DESCRIPTION

Figure 2:
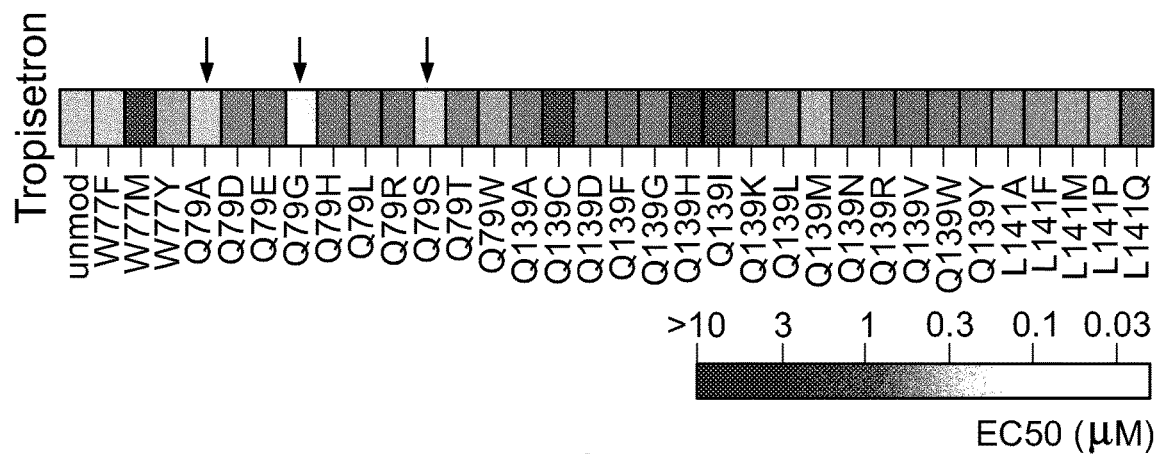
FIG. 2 shows EC50s for tropisetron against a α7-5HT3 chimeric LGIC and variants of the chimeric LGIC with LBD mutations at positions noted in FIG. 1. Multiple mutations at Gln79 showed similar or improved potency relative to the unmodified α7-5HT3 channel (arrows).

This document provides modified LGICs and methods of using them. For example, this document provides modified LGICs including at least one modified LGIC subunit having a LBD and an IPD, and having at least one modified amino acid (e.g., an amino acid substitution). In some cases, a modified LGIC can be a chimeric LGIC. For example, a chimeric LGIC can include a LBD from a first LGIC and an IPD from a second LGIC. In some cases, the modified amino acid can confer pharmacological selectivity to the modified LGIC. For example, the modified amino acid can confer the modified LGIC with selective binding of an exogenous LGIC ligand. For example, the modified amino acid can confer the modified LGIC with reduced (minimized or eliminated) binding of an unmodified LGIC subunit (an LGIC subunit lacking the modification and/or an endogenous LGIC subunit). For example, the modified amino acid can confer the modified LGIC with reduced (minimized or eliminated) binding of an endogenous LGIC ligand.

Modified LGICs provided herein can be used, for example, in methods for treating channelopathies (e.g., a neural channelopathy or a muscle channelopathy). For example, a modified LGIC, and an exogenous LGIC ligand that can bind to and activate the modified LGIC, can be used to treat a mammal having a channelopathy. In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

Modified LGICs

As used herein a "modified" LGIC is an LGIC that includes at least one LGIC subunit. A modified LGIC subunit can include at least one modified amino acid (e.g., an amino acid substitution) in the LBD and/or at least one modified amino acid (e.g., an amino acid substitution) in the IPD. A modified LGIC subunit described herein can be a modification of an LGIC from any appropriate species (e.g., human, rat, mouse, dog, cat, horse, cow, goat, pig, or monkey). In some cases, a modified LGIC can include at least one chimeric LGIC subunit having a non-naturally occurring combination of a LBD from a first LGIC and an IPD from a second LGIC.

A modified LGIC can be a homomeric (e.g., having any number of the same modified LGIC subunits) or heteromeric (e.g., having at least one modified LGIC subunit and any number of different LGIC subunits). In some cases, a modified LGIC described herein can be a homomeric modified LGIC. A modified LGIC described herein can include any suitable number of modified LGIC subunits. In some cases, a modified LGIC can be a trimer, a tetramer, a pentamer, or a hexamer. For example, a modified LGIC described herein can be a pentamer.

A modified LGIC subunit described herein can be a modification of any appropriate LGIC. The LGIC can conduct anions, cations, or both through a cellular membrane in response to the binding of a ligand. For example, the LGIC can transport sodium (Na+), potassium (K+), calcium (Ca2+), and/or chloride (Cl−) ions through a cellular membrane in response to the binding of a ligand. Examples of LGICs include, without limitation, Cys-loop receptors (e.g., AChR such as a nAChR (e.g., a muscle-type nAChR or a neuronal-type nAChR), gamma-aminobutyric acid (GABA; such as GABA$_A$ and GABA$_{A-ρ}$ (also referred to as GABAc) receptors, GlyR, GluCl receptors, and 5HT3 receptors), ionotropic glutamate receptors (iGluR; such as AMPA receptors, kainate receptors, NMDA receptors, and delta receptors), ATP-gated channels (e.g., P2X), and phosphatidylinositol 4,5-bisphosphate (PIP2)-gated channels. In cases where a modified LGIC described herein is a chimeric LGIC, the chimeric LGIC can include a LBD selected from any appropriate LGIC and an IPD selected from any appropriate LGIC. In cases where a LGIC includes multiple different subunits (for example, a neuronal-type nAChR includes α4, β2, and α7 subunits), the LBD and/or IPD can be selected from any of the subunits. For example, a LBD from a nAChR can be a α7 LBD. A representative rat α7 nAChR amino acid sequence (including both a LBD and an IPD) is as follows.

SEQ ID NO: 12
MGGGRGGIWLALAAALLHVSLQGEFQRRLYKELVKNYNPLERPVANDSQP

LTVYFSLSLLQIMDVDEKNQVLTTNIWLQMSWTDHYLQWNMSEYPGVKNV

RFPDGQIWKPDILLYNSADERFDATFHTNVLVNASGHCQYLPPGIFKSSC

YIDVRWFPFDVQQCKLKFGSWSYGGWSLDLQMQEADISSYIPNGEWDLMG

IPGKRNEKFYECCKEPYPDVTYTVTMRRRTLYYGLNLLIPCVLISALALL

VFLLPADSGEKISLGITVLLSLTVFMLLVAEIMPATSDSVPLIAQYFAST

MIIVGLSVVVTVIVLRYHHHDPDGGKMPKWTRIILLNWCAWFLRMKRPGE

DKVRPACQHKPRRCSLASVELSAGAGPPTSNGNLLYIGFRGLEGMHCAPT

PDSGVVCGRLACSPTHDEHLMHGAHPSDGDPDLAKILEEVRYIANRNRCQ

DESEVICSEWKFAACVVDPLCLMAFSVFTIICTIGILMSAPNFVEAVSKD

FA

In some cases, a modified LGIC subunit described herein can include a LBD from a α7 nAChR. Examples of α7 nAChR LBDs include, without limitation, a human α7 nAChR LBD having the amino acid sequence set forth in SEQ ID NO:1, a human α7 nAChR LBD having the amino acid sequence set forth in SEQ ID NO:2, and a human α7 nAChR LBD having the amino acid sequence set forth in SEQ ID NO:11. In some cases, a α7 nAChR LBD can be a homolog, orthologue, or paralog of the human α7 nAChR LBD set forth in SEQ ID NO:1, SEQ ID NO:2, or SEQ ID NO:11. In some cases, a α7 nAChR LBD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:1, SEQ ID NO:2, or SEQ ID NO:11.

SEQ ID NO: 1
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTV

SEQ ID NO: 2
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRR

SEQ ID NO: 11
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRTLYY

In some cases, a modified LGIC subunit described herein can include a IPD from a 5HT3 receptor. Examples of 5HT3 IPDs include, without limitation, a murine 5HT3 IPD having the amino acid sequence set forth in SEQ ID NO:3, and a human 5HT3 IPD having the amino acid sequence set forth in SEQ ID NO:4. In some cases, a 5HT3 IPD can be a homolog, orthologue, or paralog of a 5HT3 IPD set forth in SEQ ID NO:3 or SEQ ID NO:4. In some cases, a 5HT3 IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:3 of SEQ ID NO:4.

SEQ ID NO: 3
IIRRRPLFYAVSLLLPSIFLMVVDIVGFCLPPDSGERVSFKITLLLGYSV

FLIIVSDTLPATIGTPLIGVYFVVCMALLVISLAETIFIVRLVHKQDLQR

PVPDWLRHLVLDRIAWILCLGEQPMAHRPPATFQANKTDDCSGSDLLPAM

GNHCSHVGGPQDLEKTPRGRGSPLPPPREASLAVRGLLQELSSIRHFLEK

RDEMREVARDWLRVGYVLDRLLFRIYLLAVLAYSITLVTLWSIWHYS

SEQ ID NO: 4
IIRRRPLFYVVSLLLPSIFLMVMDIVGFYLPPNSGERVSFKITLLLGYSV

FLIIVSDTLPATAIGTPLIGVYFVVCMALLVISLAETIFIVRLVHKQDLQ

QPVPAWLRHLVLERIAWLLCLREQSTSQRPPATSQATKTDDCSAMGNHCS

HMGGPQDFEKSPRDRCSPPPPPREASLAVCGLLQELSSIRQFLEKRDEIR

EVARDWLRVGSVLDKLLFHIYLLAVLAYSITLVMLWSIWQYA

In some cases, a modified LGIC subunit described herein can include an IPD from a GlyR. Examples of GlyR IPDs include, without limitation, a murine GlyR IPD having the amino acid sequence set forth in SEQ ID NO:5. In some cases, a GlyR IPD can be a homolog, orthologue, or paralog of the human GlyR IPD set forth in SEQ ID NO:5. In some cases, a GlyR IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:5.

SEQ ID NO: 5
MGYYLIQMYIPSLLIVILSWISFWINMDAAPARVGLGITTVLTMTTQSSG

SRASLPKVSYVKAIDIWMAVCLLFVFSALLEYAAVNFVSRQHKELLRFRR

KRRHHKEDEAGEGRFNFSAYGMGPACLQAKDGISVKGANNSNTTNPPPAP

SKSPEEMRKLFIQRAKKIDKISRIGFPMAFLIFNMFYWIIYKIVRREDVH

NQ

In some cases, a modified LGIC subunit described herein can include an IPD from a GABA receptor (e.g., GABA$_{A-\rho}$, also referred to as GABAc). Examples of GABA$_{A-\rho}$ IPDs include, without limitation, a human GABA$_{A-\rho}$ IPD having the amino acid sequence set forth in SEQ ID NO:9. In some cases, a GABA$_{A-\rho}$ IPD can be a homolog, orthologue, or paralog of the human GABA$_{A-\rho}$ IPD set forth in SEQ ID NO:9. In some cases, a GABA$_{A-\rho}$ IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:9.

SEQ ID NO: 9
LLQTYFPATLMVMLSWVSFWIDRRAVPARVPLGITTVLTMSTIITGVNAS

MPRVSYIKAVDIYLWVSFVFVFLSVLEYAAVNYLTTVQERKEQKLREKLP

CTSGLPPPRTAMLDGNYSDGEVNDLDNYMPENGEKPDRMMVQLTLASERS

SPQRKSQRSSYVSMRIDTHAIDKYSRIIFPAAYILFNLIYWSIFS

In calculating percent sequence identity, two sequences are aligned and the number of identical matches of amino acid residues between the two sequences is determined. The number of identical matches is divided by the length of the aligned region (i.e., the number of aligned amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. The alignment of two or more sequences to determine percent sequence identity can be performed using the computer program ClustalW and default parameters, which calculates the best match between a query and one or more subject sequences, and aligns them so that identities, similarities and differences can be determined. See, e.g., Chenna et al., 2003, Nucleic Acids Res., 31(13):3497-500.

In cases where a modified LGIC subunit described herein is a chimeric LGIC subunit, the chimeric LGIC subunit can include a LBD and IPD from the same species or a LBD and IPD from different species. In some cases, a chimeric LGIC subunit can include a LBD from a human LGIC protein and an IPD from a human LGIC protein. For example, a chimeric LGIC subunit can include a human α7 LBD and a human GlyR IPD. In some cases, a chimeric LGIC subunit can include a LBD from a human LGIC protein and an IPD from a murine LGIC protein. For example, a chimeric LGIC subunit can include a human α7 LBD and a murine 5HT3 IPD.

In cases where a modified LGIC subunit described herein is a chimeric LGIC subunit, the chimeric LGIC subunit can include varied fusion points connecting the LBD and the IPD such that the number of amino acids in a LBD may vary when the LBD is fused with different IPDs to form a chimeric channel subunit. For example, the length of an α7 nAChR LBD used to form a chimeric LGIC subunit with a 5HTS IPD is different from the length of an α7 nAChR LBD used to form a chimeric LGIC subunit with a GlyR IPD (compare, for example, FIGS. 1A and 1C to FIG. 1B).

A modified LGIC subunit described herein can include a LBD having at least one modified amino acid and/or an IPD having at least one modified amino acid. For example, a modified LGIC subunit described herein can include a α7 LBD having at least 75 percent sequence identity to SEQ ID NO:1, SEQ ID NO:2, SEQ ID NO:11, or SEQ ID NO:12, and an amino acid substitution at amino acid residue 27, 41, 77, 79, 131, 139, 141, 175, 210, 216, 217, and/or 219. For example, a modified LGIC subunit described herein can include a GlyR IPD having at least 75 percent sequence identity to a sequence set forth in SEQ ID NO:5, and an amino acid substitution at amino acid residue 298 of an α7-GlyR chimeric receptor (e.g., SEQ ID NO:7). For example, a modified LGIC subunit described herein can include a GABAc IPD having at least 75 percent sequence identity to SEQ ID NO:9, and an amino acid substitution at amino acid residue 298 of an α7-GABAc chimeric receptor (e.g., SEQ ID NO:10). In some cases, a modified LGIC subunit described herein can include more than one (e.g., two, three, four, five, six, seven, eight, nine, ten, eleven, twelve, or more) amino acid modifications. The modification can be an amino acid substitution. In some cases, the modified amino acid can confer pharmacological selectivity to the modified LGIC. For example, the modified amino acid can confer the modified LGIC with selective binding of an exogenous LGIC ligand. For example, the modified amino acid can confer the modified LGIC with reduced (minimized or eliminated) binding of an unmodified LGIC subunit (an LGIC subunit lacking the modification and/or an endogenous LGIC subunit). For example, the modified amino acid can confer the modified LGIC with reduced (minimized or eliminated) binding of an endogenous LGIC ligand.

In some aspects, a modified LGIC subunit described herein can include at least one modified amino acid that confers the modified LGIC with selective binding (e.g., enhanced binding or increased potency) with an exogenous LGIC ligand. The binding with an exogenous LGIC ligand can be selective over the binding with an endogenous LGIC ligand. A modified LGIC subunit with selective binding with an exogenous LGIC ligand can include any appropriate LDB (e.g., a α7 LBD). In some aspects, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 77, 79, 131 139, 141, 175, and/or 216. In some cases, the tryptophan at amino acid residue 77 of SEQ ID NO:1, SEQ ID NO:2, SEQ ID NO:11, or SEQ ID NO:12 can be substituted with a hydrophobic amino acid residue such as phenylalanine (e.g., W77F), tyrosine (e.g., W77Y), or methionine (e.g., W77M). For example, a modified LGIC subunit described herein can include a α7 LBD set forth in SEQ ID NO:1, SEQ ID NO:2, SEQ ID NO:11, or SEQ ID NO:12 and having a W77F substitution. In some cases, the glutamine at amino acid residue 79 of SEQ ID NO:1, SEQ ID NO:2, SEQ ID NO:11, or SEQ ID NO:12 can be substituted with an amino acid residue such as alanine (e.g., Q79A), glycine (e.g., Q79G), or serine (e.g., Q79S). For example, a modified LGIC subunit described herein can include a α7 LBD having a Q79G substitution. In some cases, the leucine at amino acid residue 131 of SEQ ID NO:1, SEQ ID NO:2, SEQ ID NO:11, or SEQ ID NO:12 can be substituted with an amino acid residue such as alanine (e.g., L131A), glycine (e.g., L131G), methionine (e.g., L131M), asparagine (e.g., L131N), glutamine (e.g., L131Q), valine (e.g., L131V), or phenylalanine (e.g., L131F). In some cases, the glycine at amino acid residue 175 of SEQ ID NO:1, SEQ ID NO:2, SEQ ID NO:11, or SEQ ID NO:12 can be substituted with an amino acid residue such as lysine (e.g., G175K), alanine (e.g., G175A), phenylalanine (e.g., G175F), histidine (e.g., G175H), methionine (e.g., G175m), arginine (e.g., G175R), serine (e.g., G175S), valine (e.g., G175V). In some cases, the proline at amino acid residue 216 of SEQ ID NO:1, SEQ ID NO:2, SEQ ID NO:11, or SEQ ID NO:12 can be substituted with an amino acid residue such as isoleucine (e.g., P216I). A modified LGIC subunit with selective binding with an exogenous LGIC ligand can include any appropriate IPD (e.g., a GlyR IPD or a $GABA_{A-\rho}$ IPD). In some aspects, the modified LGIC subunit can include a GlyR IPD set forth in SEQ ID NO:5, and the amino acid modification can be a substitution at amino acid residue 298 of an α7-GlyR chimeric receptor (e.g., SEQ ID NO:7). In some cases, the alanine at amino acid residue 298 of SEQ ID NO:7 can be substituted with an amino acid residue such as glycine (e.g., A298G). In some aspects, the modified LGIC subunit can include the a GABA$_{A-\rho}$ IPD set forth in SEQ ID NO:9, and the amino acid modification can be a substitution at amino acid residue 298 of an α7-GABA$_{A-\rho}$ chimeric receptor (e.g., SEQ ID NO:10). In some cases, the tryptophan at amino acid residue 298 of SEQ ID NO:10 can be substituted with an amino acid residue such as alanine (e.g., W298A).

In some cases, a modified LGIC subunit described herein can include more than one (e.g., two, three, four, five, six, seven, eight, nine, ten, eleven, twelve, or more) amino acid modifications. For example, a modified LGIC subunit described herein can have at least 75 percent sequence identity to SEQ ID NO:7 and can include a Q79G substitution and a A298G substitution. Additional examples of modifications that can confer the modified LGIC with selective binding of an exogenous LGIC ligand include modifications described elsewhere (see, e.g., U.S. Pat. No. 8,435,762).

A modified LGIC subunit that selectively binds (e.g., enhanced binding or increased potency) an exogenous LGIC ligand over an endogenous (e.g., a canonical) LGIC ligand can also be described as having enhanced potency for an exogenous ligand. In some cases, a modified LGIC subunit described herein that selectively binds an exogenous LGIC ligand can have at least 4 fold (e.g., at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold) enhanced potency for an exogenous ligand. In some cases, a modified LGIC subunit described herein that selectively binds an exogenous LGIC ligand can have about 4 fold to about 200 fold (e.g., about 4 fold to about 200 fold, about 5 fold to about 180 fold, about 6 fold to about 175 fold, about 7 fold to about 150 fold, about 8 fold to about 125 fold, about 9 fold to about 100 fold, about 10 fold to about 90 fold, about 11 fold to about 75 fold, about 12 fold to about 65 fold, about 13 fold to about 50 fold, about 14 fold to about 40 fold, or about 15 fold to about 30 fold) enhanced potency for an exogenous ligand. For example, a modified LGIC subunit described herein that selectively binds an exogenous LGIC ligand can have about 10 fold to about 100 fold enhanced potency for an exogenous ligand. For example, a modified LGIC subunit described herein that selectively binds an exogenous LGIC ligand can have about 10 fold to about 20 fold enhanced potency for an exogenous ligand.

In some aspects, a modified LGIC subunit described herein can include at least one modified amino acid that confers the modified LGIC with reduced (e.g., minimized or eliminated) binding with an unmodified LGIC subunit. The binding with a modified LGIC subunit having the same modification can be selective over the binding with an unmodified LGIC subunit. An unmodified LGIC subunit can be a LGIC subunit lacking the modification that confers the modified LGIC with reduced binding with an unmodified LGIC subunit or an unmodified LGIC can be an endogenous LGIC subunit. The modification that confers the modified LGIC with reduced binding with an unmodified LGIC subunit can be a charge reversal modification. A modified LGIC subunit with reduced binding with an unmodified LGIC subunit can include any appropriate LBD (e.g., a α7 LBD). In some aspects, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 27 and/or 41. For example, the arginine at amino acid residue 27 of SEQ ID NO:1, SEQ ID NO:2, SEQ ID NO:11, or SEQ ID NO:12 can be substituted with an aspartic acid (e.g., R27D). For example, the glutamic acid at amino acid residue 41 of SEQ ID NO:1, SEQ ID NO:2, SEQ ID NO:11, or SEQ ID NO:12 can be substituted with an arginine (e.g., E41R). In some cases, a modified LGIC subunit described herein can include a α7 LBD having a R27D substitution and a E41R.

In some aspects, a modified LGIC subunit described herein can include at least one modified amino acid that confers the modified LGIC with reduced (e.g., minimized or eliminated) binding of an endogenous LGIC ligand. The endogenous LGIC ligand can be ACh. A modified LGIC subunit with reduced binding of an endogenous LGIC ligand can include any appropriate IPD (e.g., a GlyR LBD). For example, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 115, 131, 139, 210, 217 and/or 219. In some cases, the tyrosine at amino acid residue 115 of SEQ ID NO:1, SEQ ID NO:2, SEQ ID NO:11, or SEQ ID NO:12 can be substituted with a phenylalanine (e.g., Y115F). In some cases, the leucine at amino acid residue 131 of SEQ ID NO:1, SEQ ID NO:2, SEQ ID NO:11, or SEQ ID NO:12 can be substituted with an amino acid residue such as alanine (e.g., L131A), glycine (e.g., L131G), methionine (e.g., L131M), asparagine (e.g., L131N), glutamine (e.g., L131Q), valine (e.g., L131V), or phenylalanine (e.g., L131F). In some cases, the glutamine at amino acid residue 139 of SEQ ID NO:1, SEQ ID NO:2, SEQ ID NO:11, or SEQ ID NO:12 can be substituted with a glycine (e.g., Q139G) or a leucine (e.g., Q139L). In some cases, the tyrosine at amino acid residue 210 of SEQ ID NO:1, SEQ ID NO:2, SEQ ID NO:11, or SEQ ID NO:12 can be substituted with a phenylalanine (e.g., Y210F). In some cases, the tyrosine at amino acid residue 217 of SEQ ID NO:1, SEQ ID NO:2, SEQ ID NO:11, or SEQ ID NO:12 can be substituted with a phenylalanine (e.g., Y217F). In some cases, the aspartate at amino acid residue 219 of SEQ ID NO:1, SEQ ID NO:2, SEQ ID NO:11, or SEQ ID NO:12 can be substituted with an alanine (e.g., D219A).

In some aspects, a modified LGIC subunit described herein can include at least one modified amino acid that confers the modified LGIC with increased ion conductance. In some cases, the modified LGIC subunit can include a 5HT3 IPD set forth in SEQ ID NO:3, and the amino acid modification can be a substitution at amino acid residue 425, 429, and/or 433. For example, a modified LGIC subunit described herein can include a 5HT3 IPD having a R425Q substitution, a R429D substitution, and a R433A substitution. In some cases, the modified LGIC subunit can include a 5HT3 IPD set forth in SEQ ID NO:4, and the amino acid modification can be a substitution at amino acid residue 420, 424, and/or 428. For example, a modified LGIC subunit described herein can include a 5HT3 IPD having a R420Q substitution, a R424D substitution, and a R428A substitution.

In some cases, a modified LGIC described herein can include at least one chimeric α7-5HT3 LGIC subunit (SEQ ID NO:6) having a human α7 nAChR LBD (SEQ ID NO:1) with a Q79G amino acid substitution and a Y115F amino acid substitution, and a murine 5HT3 IPD (SEQ ID NO:3).

In some cases, a modified LGIC described herein can include at least one chimeric α7-5HT3 LGIC subunit (SEQ ID NO:6) having a human α7 nAChR LBD (SEQ ID NO:1) with a Q79G amino acid substitution and a Q139G amino acid substitution, and a murine 5HT3 IPD (SEQ ID NO:3).

In some cases, a modified LGIC described herein can include at least one chimeric α7-GlyR LGIC subunit (SEQ ID NO:7) having a human α7 nAChR LBD (SEQ ID NO:2) with a Q79G amino acid substitution and a Y115F amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a Q79G amino acid substitution and a Q139G amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a R27D amino acid substitution, a E41R amino acid substitution, a Q79G amino acid substitution, and a Y115F amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a substitution at amino acid residue 131 (e.g., L131G, L131A, L131M, or L131N), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and Y115 (e.g., Y115F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and 139 (e.g., Q139L), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and 217 (e.g., Y217F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N), 139 (e.g., Q139L), and 217 (e.g., Y217F), and a human GlyR IPD (SEQ ID NO:5).

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N), and a human 5HT3 IPD (SEQ ID NO:4).

In some cases, a modified LGIC described herein can include at least one chimeric α7-GlyR LGIC subunit (SEQ ID NO:7) having a human α7 nAChR LBD (SEQ ID NO:2) with a substitution at amino acid residue 175 (e.g., G175K), and a human GlyR IPD (SEQ ID NO:5).

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N) and 139 (e.g., Q139L), and a human 5HT3 IPD (SEQ ID NO:4) with a R420Q substitution, a R424D substitution, and a R428A substitution.

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N) and 139 (e.g., Q139L) and 217 (e.g., Y217F), and a human 5HT3 IPD (SEQ ID NO:4) with a R420Q substitution, a R424D substitution, and a R428A substitution.

In some cases, a modified LGIC described herein can include at least one chimeric α7-GlyR LGIC subunit (SEQ ID NO:7) having a human α7 nAChR LBD (SEQ ID NO:2) with a substitution at amino acid residues 175 (e.g., G175K) and 115 (e.g., Y115F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 175 (e.g., G175K) and 115 (e.g., Y115F) and 79 (e.g., Q79G), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 175 (e.g., G175K) and 77 (e.g., W77F) and 79 (e.g., Q79G), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residue 216 (e.g., P216I), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 216 (e.g., P216I) and 79 (e.g., Q79G), and a human GlyR IPD (SEQ ID NO:5).

In some cases, a modified LGIC described herein can include at least one chimeric α7-GlyR LGIC subunit (SEQ ID NO:10) having a human α7 nAChR LBD (SEQ ID NO:2) with a substitution at amino acid residue 131 (e.g., L131A, L131G, L131M, L131N, L131Q, L131V, or L131F), and a human GABAc IPD (SEQ ID NO:9).

In cases where a LBD and/or a IPD is a homolog, orthologue, or paralog of a sequence set forth herein (e.g., SEQ ID NOs:1-5 and/or 9), it is understood that reference to a particular modified amino acid residue can shift to the corresponding amino acid in the homolog, orthologue, or paralog. For example, residues 425, 429, and 433 in a murine 5HT3 IPD set forth in SEQ ID NO:3 correspond to residues 420, 424, and 428 in a human 5HT3 IPD set forth in SEQ ID NO:4, and the R425Q, R429D, and R433A substitutions in a murine 5HT3 IPD correspond to R420Q, R424D, and R428A substitutions in a human 5HT3 IPD.

Any method can be used to obtain a modified LGIC subunit described herein. In some cases, peptide synthesis methods can be used to make a modified LGIC subunit described herein. Examples of methods of peptide synthesis include, without limitation, liquid-phase peptide synthesis, and solid-phase peptide synthesis. In some cases, protein biosynthesis methods can be used to make a modified LGIC subunit described herein. Examples of methods of protein biosynthesis include, without limitation, transcription and/or translation of nucleic acids encoding a phosphorylation-mimicking peptide provided herein. Similar modified LGIC subunits (e.g., modified subunits having essentially the same modifications and/or having essentially the same amino acid sequence) will self-assemble through interactions between the LBDs to form a modified LGIC.

This document also provides nucleic acids encoding modified LGIC subunits described herein as well as constructs (e.g., plasmids, non-viral vectors, viral vectors (such as adeno-associated virus, a herpes simplex virus, or lentivirus vectors)) for expressing nucleic acids encoding modified LGIC subunits described herein. Nucleic acids encoding modified LGIC subunits described herein can be operably linked to any appropriate promoter. A promoter can be a native (i.e., minimal) promoter or a composite promoter. A promoter can be a ubiquitous (i.e., constitutive) promoter or a regulated promoter (e.g., inducible, tissue specific, cell-type specific (e.g., neuron specific, muscle specific, glial specific), and neural subtype-specific). Examples of promoters that can be used to drive expression of nucleic acids encoding modified LGIC subunits described herein include, without limitation, synapsin, CAMKII, CMV, CAG, enolase, TRPV1, POMC, NPY, AGRP, MCH, and Orexin promoters. In some cases, a nucleic acid encoding a modified LGIC subunit described herein can be operably linked to a neuron specific promoter.

This document also provides cells (e.g., mammalian cells) having a modified LGIC described herein. Mammalian cells having a modified LGIC described herein can be obtained by any appropriate method. In some cases, a pre-assembled modified LGIC can be provided to the cell. In some cases, a nucleic acid encoding a modified LGIC subunit described herein can be provided to the cell under conditions in which a modified LGIC subunit is translated and under conditions in which multiple (e.g., three, four, five, six, or more) modified LGIC subunits can assemble into a modified LGIC described herein.

LGIC Ligands

This document also provides LGIC ligands that can bind to and activate modified LGICs described herein. A LGIC ligand that can bind to and activate modified LGICs described herein can be exogenous or endogenous. A LGIC ligand that can bind to and activate modified LGICs described herein can be naturally occurring or synthetic. A LGIC ligand that can bind to and activate modified LGICs described herein can be canonical or non-canonical. A LGIC ligand that can bind to and activate modified LGICs described herein can be an agonist or an antagonist. In some cases, an LGIC ligand is an exogenous LGIC agonist. Examples of LGIC ligands include, without limitation, ACh, nicotine, epibatatine, cytisine, RS56812, tropisetron, nortropisetron, PNU-282987, PHA-543613, compound 0353, compound 0354, compound 0436, compound 0676, compound 702, compound 723, compound 725, granisetron, ivermectin, mequitazine, promazine, varenicline, compound 765, compound 770, 3-(1,4-diazabicyclo[3.2.2]nonan-4-yl) dibenzo[b,d]thiophene 5,5-dioxide, compound 773, and compound 774 (see, e.g., FIG. 3B, FIG. 5C, FIG. 10A, and FIG. 10B).

A LGIC ligand that can bind to and activate modified LGICs described herein can have selective binding (e.g., enhanced binding or increased potency) for a modified LGIC described herein. In some cases, a LGIC ligand that can bind to and activate modified LGICs described herein does not bind to and activate endogenous receptors. A LGIC ligand that selectively binds to and activates a modified LGIC (e.g., a modified LGIC having at least one amino acid modification that confers pharmacological selectivity to the modified LGIC) described herein over an unmodified LGIC ligand can also be described as having enhanced potency for a modified LGIC. In some cases, a modified LGIC subunit described herein that selectively binds an exogenous LGIC ligand can have at least 5 fold (e.g., at least 10 fold, at least 15 fold, at least 20 fold, at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 95 fold, at least 100 fold, at least 125 fold, at least 150 fold, at least 200 fold, at least 250 fold, or at least 300 fold) enhanced potency for a modified LGIC. For example, a LGIC ligand that selectively binds to and activates a modified LGIC can have about 10 fold to about 300 fold (e.g., about 10 fold to about 250 fold, about 10 fold to about 200 fold, about 10 fold to about 150 fold, about 10 fold to about 100 fold, about 25 fold to about 300 fold, about 50 fold to about 300 fold, about 100 fold to about 300 fold, about 200 fold to about 300 fold, about 25 fold to about 250 fold, about 50 fold to about 200 fold, or about 100 fold to about 150 fold) enhanced potency for a modified LGIC. In some cases, a LGIC ligand that binds to and activates a modified LGIC described herein can have a ligand potency of less than 25 nM (e.g., less than 22 nM, less than 20 nM, less than 17 nM, less than 15 nM, less than 13 nM, less than 12 nM, less than 11 nM, less than 10 nM, less than 5 nM, less, than 2 nM, or less than 1 nM). For example, a LGIC ligand that binds to and activates a modified LGIC described herein can have a ligand potency of less than 15 nM. In some cases, a LGIC ligand can have an EC50 of less than 25 nM (e.g., less than 22 nM, less than 20 nM, less than 17 nM, less than 15 nM, less than 13 nM, less than 12 nM, less than 11 nM, or less than 10 nM) for a modified LGIC subunit described herein. For example, a LGIC ligand (e.g., tropisetron) can have an EC50 of about 11 nM for a modified LGIC subunit described herein (e.g., $\alpha7^{Q79G}$-GlyR$^{A298G}$). For example, a LGIC ligand (e.g., nortropisetron) can have an EC50 of about 13 nM for a modified LGIC subunit described herein (e.g. $\alpha7^{Q79G,Y115F}$-GlyR$^{A298G}$), In some cases, a LGIC ligand can have an EC50 of greater than 20 μM (e.g., greater than 22 μM, greater than 25 μM, greater than 35 μM, greater than 50, greater than 65 μM, greater than 80 μM, or greater than 100 μM) for a modified LGIC subunit described herein. For example, a LGIC ligand (e.g., ACh) can have an EC50 of greater than 100 μM for a modified LGIC subunit described herein (e.g., $\alpha7^{Q79G,Y115F}$-GlyR$^{A298G}$).

In some aspects, a LGIC ligand can be a synthetic ligand that can bind to and activate modified LGICs described herein can be a quinuclidine, a tropane, a 9-azabicyclo [3.3.1]nonane, or a 2-phenyl-7,8,9,10-tetrahydro-6H-6,10-methanoazepino[4,5-g]quinoxaline.

A LGIC ligand that can be to and activate a modified LGIC described herein can have Formula I:

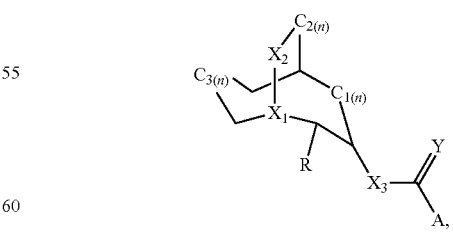

where X1 and X2 can independently be CH, CH2, O, NH, or NMe; each n can independently be 0 or 1; Y can be O or S; A can be an aromatic substituent; and R can be H or pyridinymethylene. Examples of aromatic substituents include, without limitation, 4-chloro-benzene, 1H-indole, 4-(trifluoromethyl) benzene, 4-chloro benzene, 2,5-dimethoxy benzene, 4-chloroaniline, aniline, 5-(trifluoromethyl) pyridin-2-yl, 6-(trifluoromethyl) nicotinic, and 4-chlorobenzene.

A LGIC ligand that can bind to and activate a modified LGIC described herein can be a quinuclidine. A quinuclidine can have the structure of Formula II:

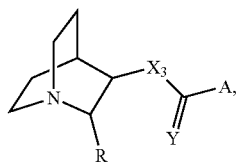

where X3 can be O, NH, or CH2; Y can be O or S; A can be an aromatic substituent; and R can be H or pyridinylmethylene. Examples of aromatic substituents include without limitation, 1H-indole, 4-(trifluoromethyl) benzene, 4-chloro benzene, 2,5-dimethoxy benzene, 4-(trifluoromethyl) benzene, 4-chloroaniline, aniline, 5-(trifluoromethyl) pyridin-2-yl, 6-(trifluoromethyl) nicotinic, 3-chloro-4-fluoro benzene, 4-chloro-benzene, and 1H-indole. Examples of quinuclidines include, without limitation, compounds PNU-282987, PHA-543613, 0456, 0434, 0436, 0354, 0353, 0295, 0296, and 0676 (see, e.g., FIG. 5C, Table 3, and Table 6).

A LGIC ligand that can bind to and activate a modified LGIC described herein can be a tropane. A tropane can have the structure of Formula III:

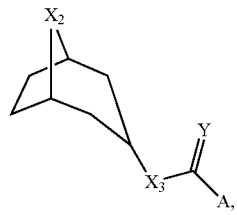

where X2 can be NH or NMe; X3 can be O, NH, or CH2; Y can be O or S; and A can be an aromatic substituent. Example of aromatic substituents include, without limitation, 1H-indole, 7-methoxy-1H-indole, 7-methyl-1H-indole, 5-chloro-1H-indole, and 1H-indazole. Examples of tropanes include, without limitation, tropisetron, pseudo-tropisetron, nortropisetron, compound 737, and compound 745 (see, e.g., FIG. 5C, Table 3, and Table 6).

A LGIC ligand that can bind to and activate a modified LGIC described herein can be a 9-azabicyclo[3.3.1]nonane. A 9-azabicyclo[3.3.1]nonane can have the structure of Formula IV:

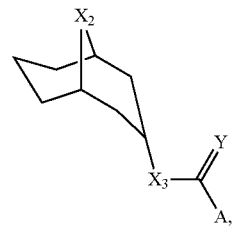

where X1 can be CH, X2 can be NH or NMe, X3 can be O, NH, or CH; Y can be 0 or S; and A can be an aromatic substituent. An example of an aromatic substituent is, without limitation, 4-chloro-benzene. Examples of 9-azabicyclo [3.3.1]nonanes include, without limitation, compound 0536, compound 0749, compound 0751, compound 0760, and compound 0763 (see, e.g., FIG. 5C, Table 3, and Table 6).

In some cases, a LGIC ligand can be an a 6,7,8,9-tetrahydro-6,10-methano-6H-pyrazino(2,3-h)benzazepine and can have a structure shown in Formula V:

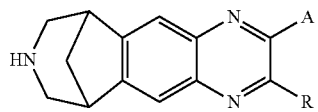

where R=H or CH₃; and where A=H or an aromatic substituent. Examples of 6,7,8,9-tetrahydro-6,10-methano-6H-pyrazino(2,3-h)benzazepines include, without limitation, varenicline, compound 0765, and compound 0770 (see, e.g., FIG. 10A, Table 3, and Table 9).

In some cases, a LGIC ligand can be a 1,4-diazabicyclo [3.2.2]nonane and can have a structure shown in Formula VI:

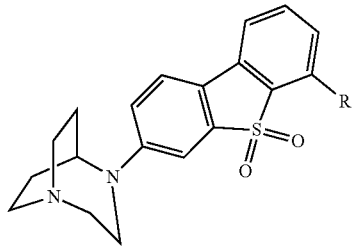

where R=H, F, NO2. Examples of 1,4-diazabicyclo[3.2.2] nonanes include, without limitation, 3-(1,4-diazabicyclo [3.2.2]nonan-4-yl)dibenzo[b,d]thiophene 5,5-dioxide, compound 0773, and compound 0774 (see, e.g., FIG. 10B, Table 6, and Table 9).

Methods of Using

This document also provides methods of using a modified LGIC described herein and a LGIC ligand that can bind to and activate the modified LGIC as described herein. A LGIC ligand that can bind to and activate the modified LGIC can be used to activate a modified LGIC with temporal and/or spatial control based on delivery of the ligand.

In some aspects, a modified LGIC described herein and a LGIC ligand that can bind to and activate the modified LGIC as described herein can be used to identify a ligand that selectively binds to a modified LGIC described herein. For example, such screening methods can include providing one or more candidate ligands to a modified LGIC described herein, and detecting binding between the candidate ligand and the modified LGIC.

Any appropriate method can be used to detect binding between a candidate ligand and the modified LGIC and any appropriate method can be used to detect activity of a modified LGIC. For example, the ability of a ligand to bind to and activate a modified LGIC can be measured by assays including, but not limited to, membrane potential (MP) assay (e.g., a fluorescence MP assay), radioactive binding assays, and/or voltage clamp measurement of peak currents and sustained currents.

In some aspects, a modified LGIC described herein and a LGIC ligand that can bind to and activate the modified LGIC as described herein can be used to treat a mammal having a channelopathy (e.g., a neural channelopathy or a muscle channelopathy). For example, a mammal having a channelopathy can be treated by administering a modified LGIC described herein, and then administering a LGIC ligand that can bind to and activate the modified LGIC. For example, a mammal having a channelopathy can be treated by administering a modified LGIC described herein (e.g., including at least one chimeric α7-GlyR LGIC subunit (SEQ ID NO:6) having a human α7 nAChR LBD (SEQ ID NO:2) with a R27D amino acid substitution, a E41R amino acid substitution, a Q79G amino acid substitution, and a Y115F amino acid substitution, and a human GlyR IPD (SEQ ID NO:5) with a A298G amino acid substitution), and then administering tropisetron. For example, a mammal having a channelopathy can be treated by administering a modified LGIC described herein including a modified human α7 nAChR LBD (e.g., SEQ ID NO:1, SEQ ID NO:2, SEQ ID NO:11, or SEQ ID NO:12) with an L131 amino acid substitution (e.g., L131G, L131A, L131M, or L131N) and, optionally, a Q79S amino acid substitution, a Q139L amino acid substitution, and/or a Y217F amino acid substitution, and then administering varenicline, tropisetron, and/or compound 765.

Any type of mammal can be treated using a modified LGIC described herein and a LGIC ligand that can bind to and activate the modified LGIC as described herein. For example, humans and other primates such as monkeys can be treated using a modified LGIC described herein and a LGIC ligand that can bind to and activate the modified LGIC as described herein. In some cases, dogs, cats, horses, cows, pigs, sheep, rabbits, mice, and rats can be treated using a modified LGIC described herein and a LGIC ligand that can bind to and activate the modified LGIC as described herein.

Any appropriate method can be used to identify a mammal having a channelopathy and/or a mammal at risk of developing a channelopathy. For example, genetic testing can be used to identify a mammal having a channelopathy and/or a mammal at risk of developing a channelopathy.

Once identified as having a channelopathy and/or a mammal at risk of developing a channelopathy, the mammal can be administered or instructed to self-administer a modified LGIC described herein, and then administered or instructed to self-administer a LGIC ligand that can bind to and activate the modified LGIC as described herein. A modified LGIC described herein and a LGIC ligand that can bind to and activate the modified LGIC as described herein can be administered together or can be administered separately.

When treating a mammal having a channelopathy and/or a mammal at risk of developing a channelopathy using the materials and methods described herein, the channelopathy can be any channelopathy. As used herein, a channelopathy can be any disease or disorder caused by aberrant ion channel function and/or aberrant ligand function, or which could be alleviated by modulated ion channel function and/or altered cellular ion flux (e.g., calcium ion flux). A channelopathy can be congenital or acquired. Examples of channelopathies include, without limitation, Bartter syndrome, Brugada syndrome, catecholaminergic polymorphic ventricular tachycardia (CPVT), congenital hyperinsulinism, cystic fibrosis, Dravet syndrome, episodic ataxia, erythromelalgia, generalized epilepsy (e.g., with febrile seizures), familial hemiplegic migraine, fibromyalgia, hyperkalemic periodic paralysis, hypokalemic periodic paralysis, Lambert-Eaton myasthenic syndrome, long QT syndrome (e.g., Romano-Ward syndrome), short QT syndrome, malignant hyperthermia, mucolipidosis type IV, myasthenia gravis, myotonia congenital, neuromyelitis optica, neuromyotonia, nonsyndromic deafness, paramyotonia congenital, retinitis pigmentosa, timothy syndrome, tinnitus, seizure, trigeminal neuralgia, and multiple sclerosis. Alternatively, or in addition, the materials and methods described herein can be used in other applications including, without limitation, pain treatment, cancer cell therapies, appetite control, spasticity treatment, muscle dystonia treatment, tremor treatment, and movement disorder treatment.

In some cases, a modified LGIC described herein and a LGIC ligand that can bind to and activate the modified LGIC as described herein can be used to modulate the activity of a cell. The activity of the cell that is modulated using a modified LGIC described herein and a LGIC ligand that can bind to and activate the modified LGIC as described herein can be any cellular activity. Examples of cellular activities include, without limitation, active transport (e.g., ion transport), passive transport, excitation, inhibition, ion flux (e.g., calcium ion flux), and exocytosis. The cellular activity can be increased or decreased. For example, a modified LGIC described herein and a LGIC ligand that can bind to and activate the modified LGIC as described herein can be used to modulate (e.g., increase) ion transport across the membrane of a cell. For example, a modified LGIC described herein and a LGIC ligand that can bind to and activate the modified LGIC as described herein can be used to modulate (e.g., increase) the excitability of a cell.

A modified LGIC described herein and a LGIC ligand that can bind to and activate the modified LGIC as described herein can be used to modulate the activity of any type of cell in a mammal. The cell can be a neuron, a glial cell, a myocyte, an immune cell (e.g., neutrophils, eosinophils, basophils, lymphocytes, and monocytes), an endocrine cell, or a stem cell (e.g., an embryonic stem cell). In some cases, the cell can be an excitable cell. The cell can be in vivo or ex vivo.

A modified LGIC described herein can be administered by any appropriate method. A modified LGIC can be administered as modified LGIC subunits or as pre-assembled modified LGICs. A modified LGIC can be administered as a nucleic acid encoding a modified LGIC. A modified LGIC can be administered as a nucleic acid encoding a modified LGIC subunit described herein. For example, a nucleic acid can be delivered as naked nucleic acid or using any appropriate vector (e.g., a recombinant vector). Vectors can be a DNA based vector, an RNA based, or combination thereof. Vectors can express a nucleic acid in dividing cells or non-dividing cells. Examples of recombinant vectors include, without limitation, plasmids, viral vectors (e.g., retroviral vectors, adenoviral vectors, adeno-associated viral vectors, and herpes simplex vectors), cosmids, and artificial chromosomes (e.g., yeast artificial chromosomes or bacterial artificial chromosomes). In some cases, a nucleic acid encoding a modified LGIC subunit described herein can be expressed by an adeno-associated viral vector.

A modified LGIC described herein can be detected (e.g., to confirm its presence in a cell) by any appropriate method. In some cases, an agent that selectively binds a modified LGIC can be used to detect the modified LGIC. Examples of agents that can be used to bind to a modified LGIC described herein include, without limitation, antibodies, proteins (e.g., bungarotoxin), and small molecule ligands (e.g., PET ligands). An agent that selectively binds a modified LGIC can include a detectable label (e.g., fluorescent labels, radioactive labels, positron emitting labels, and enzymatic labels). Methods to detect LGIC expression in a cell can include fluorescence imaging, autoradiography, functional MRI, PET, and SPECT.

A modified LGIC described herein and a LGIC ligand that can bind to and activate the modified LGIC as described herein can be administered to a mammal having a channelopathy and/or at risk of developing a channelopathy as a combination therapy with one or more additional agents/therapies used to treat a channelopathy. For example, a combination therapy used to treat a mammal having a channelopathy as described herein can include administering a modified LGIC described herein and a LGIC ligand that can bind to and activate the modified LGIC as described herein and treating with acetazolaminde, dichlorphenamide, mexilitine, glucose, calcium gluconate, L-DOPA, muscle stimulation, spinal stimulation, brain stimulation, and/or nerve stimulation.

In embodiments where a modified LGIC described herein and a LGIC ligand that can bind to and activate the modified LGIC as described herein are used in combination with additional agents/therapies used to treat a channelopathy, the one or more additional agents can be administered at the same time or independently. For example, a modified LGIC described herein and a LGIC ligand that can bind to and activate the modified LGIC as described herein first, and the one or more additional agents administered second, or vice versa. In embodiments where a modified LGIC described herein and a LGIC ligand that can bind to and activate the modified LGIC as described herein are used in combination with one or more additional therapies used to treat a channelopathy, the one or more additional therapies can be performed at the same time or independently of the administration of a modified LGIC described herein and a LGIC ligand that can bind to and activate the modified LGIC as described herein. For example, a modified LGIC described herein and a LGIC ligand that can bind to and activate the modified LGIC as described herein can be administered before, during, or after the one or more additional therapies are performed.

In some cases, a modified LGIC described herein and/or a LGIC ligand that can bind to and activate the modified LGIC as described herein can be formulated into a pharmaceutically acceptable composition for administration to a mammal having a channelopathy or at risk of developing a channelopathy. For example, a therapeutically effective amount of a modified LGIC described herein (e.g., a nucleic acid encoding a modified LGIC described herein) and/or a LGIC ligand that can bind to and activate the modified LGIC as described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing a modified LGIC described herein and/or a LGIC ligand that can bind to and activate the modified LGIC as described herein can be designed for oral, parenteral (including subcutaneous, intracranial, intraarterial, intramuscular, intravenous, intracoronary, intradermal, or topical), or inhaled administration. When being administered orally, a pharmaceutical composition containing a therapeutically effective amount of a modified LGIC described herein (e.g., a nucleic acid encoding a modified LGIC described herein) and/or a LGIC ligand that can bind to and activate the modified LGIC as described herein can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

A pharmaceutically acceptable composition including a therapeutically effective amount of a modified LGIC described herein (e.g., a nucleic acid encoding a modified LGIC described herein) and/or a LGIC ligand that can bind to and activate the modified LGIC as described herein can be administered locally or systemically. In some cases, a composition containing a therapeutically effective amount of a modified LGIC described herein (e.g., a nucleic acid encoding a modified LGIC described herein) and/or a LGIC ligand that can bind to and activate the modified LGIC as described herein can be administered systemically by venous or oral administration to, or inhalation by a mammal (e.g., a human). In some cases, a composition containing a therapeutically effective amount of a modified LGIC described herein (e.g., a nucleic acid encoding a modified LGIC described herein) and/or a LGIC ligand that can bind to and activate the modified LGIC as described herein can be administered locally by percutaneous, subcutaneous, intramuscular, intracranial, or open surgical administration (e.g., injection) to a target tissue of a mammal (e.g., a human).

Effective doses can vary depending on the severity of the channelopathy, the route of administration, the age and general health condition of the subject, excipient usage, the possibility of co-usage with other therapeutic treatments such as use of other agents, and the judgment of the treating physician.

The frequency of administration can be any frequency that improves symptoms of a channelopathy without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing a therapeutically effective amount of a modified LGIC described herein (e.g., a nucleic acid encoding a modified LGIC described herein)

and/or a LGIC ligand that can bind to and activate the modified LGIC as described herein can include rest periods. For example, a composition containing a therapeutically effective amount of a modified LGIC described herein (e.g., a nucleic acid encoding a modified LGIC described herein) and/or a LGIC ligand that can bind to and activate the modified LGIC as described herein can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the channelopathy may require an increase or decrease in administration frequency.

Figure 3A:
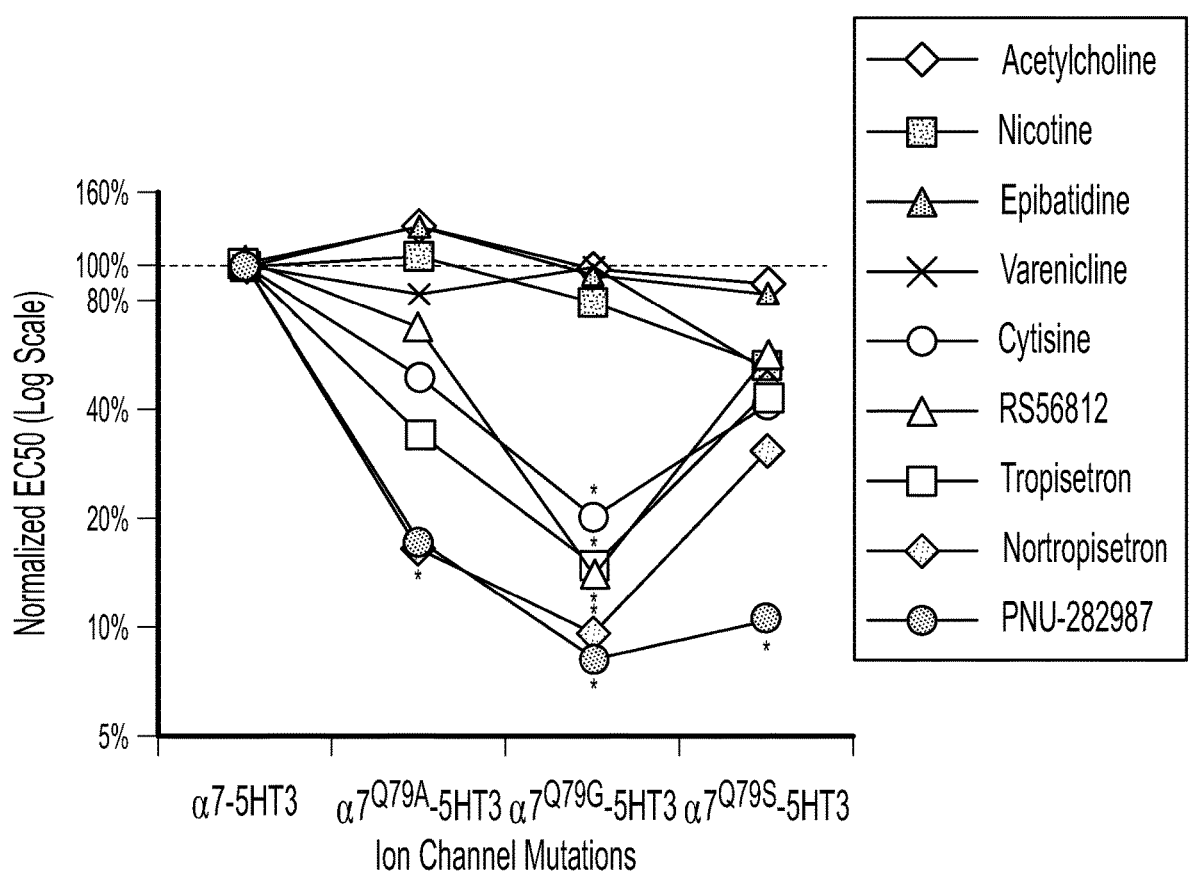
FIGS. 3A-3B show the relative potency of known nAChR agonists for α7-5HT3 chimeric LGICs.
Figure 3B:
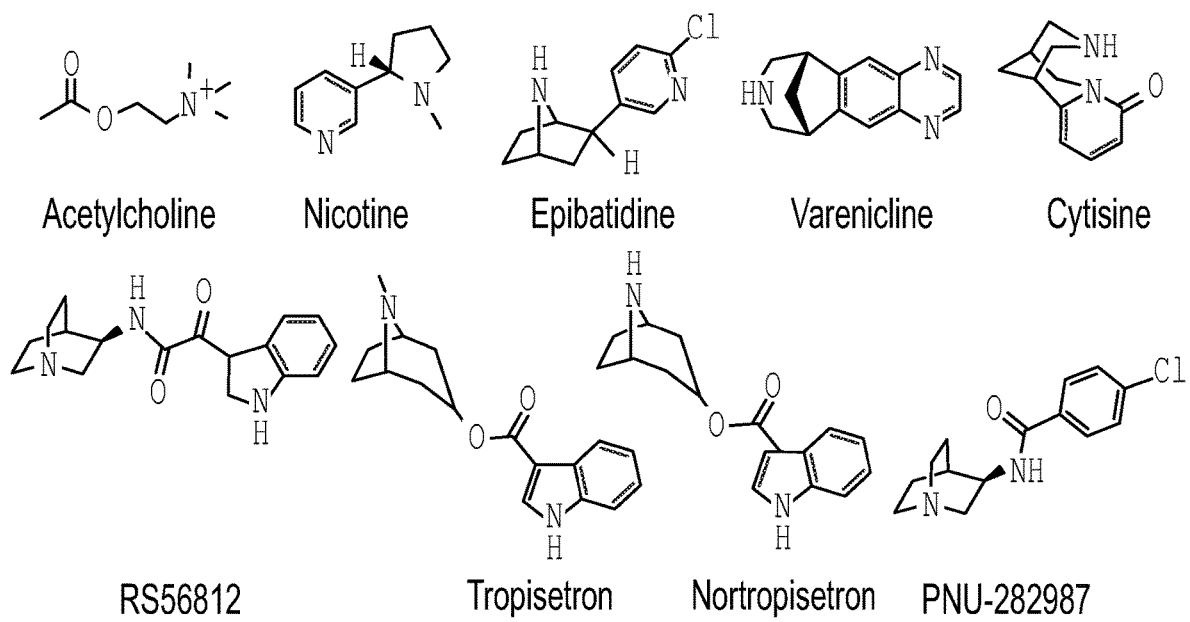

An effective duration for administering a composition containing a therapeutically effective amount of a modified LGIC described herein (e.g., a nucleic acid encoding a modified LGIC described herein) and/or a LGIC ligand that can bind to and activate the modified LGIC as described nAChR LBD that enhanced potency for the known nAChR agonist tropisetron (FIG. 2). These mutations (Q79A, Q79G, Q79S) reduce the size of the amino acid side chain. Some mutant ion channel-ligand combinations gave up to 12-fold improvement in potency (Table 1, FIG. 3). Canonical α7 nAChR agonists, ACh, nicotine, epibatidine, and the anti-smoking drug varenicline were not significantly affected by Q79A, Q79G, or Q79S mutations. However, a subset of α7 nAChR agonists showed enhanced potency with some of the mutations. Cytisine, RS56812, tropisetron, nortropisetron, and PNU-282987 showed significantly improved potency for α7$^{Q79G}$-5HT3. Additionally, nortropisetron and PNU-282987 showed a significantly enhanced potency for α7$^{Q79A}$-5HT3 and α7$^{Q79S}$-5HT3, respectively. In general, agonists based on a quinuclidine or tropane pharmacophore with a linked aromatic structure that interacts with the complementary binding face of the ligand binding domain showed improved potency with Gln79 substitution with the smaller amino acid residues Ala, Gly, or Ser. For most agonists, α7$^{Q79G}$-5HT3 was the most preferred mutant chimeric ion channel.

TABLE 1

Potency of nAChR agonists against chimeric cation channels mutated at Gln79 in HEK cells. Mean EC50, SEM in parentheses (μM).

| Agonist | α7-5HT3 | α7$^{Q79A}$-5HT3 | α7$^{Q79G}$-5HT3 | α7$^{Q79S}$-5HT3 |
|---|---|---|---|---|
| Acetylcholine | 7.0 (0.8) | 9.2 (1.8) | 6.7 (0.6) | 6.2 (1.4) |
| Nicotine | 3.9 (0.4) | 4.1 (1.3) | 3.1 (0.5) | 2.1 (0.4) |
| Epibatidine | 0.053 (0.006) | 0.067 (0.022) | 0.050 (0.008) | 0.044 (0.006) |
| Varenicline | 0.92 (0.16) | 0.76 (0.21) | 0.91 (0.12) | 0.47 (0.07) |
| Cytisine | 8.2 (0.3) | 4.0 (0.9) | 1.7 (0.2) | 4.4 (1.0) |
| RS56812 | 10 (1.8) | 6.8 (1.9) | 1.4 (0.2) | 5.7 (0.8) |
| Tropisetron | 0.24 (0.03) | 0.08 (0.02) | 0.035 (0.002) | 0.11 (0.02) |
| Nortropisetron | 0.061 (0.021) | 0.010 (0.002) | 0.006 (0.001) | 0.019 (0.007) |
| PNU-282987 | 0.22 (0.03) | 0.037 (0.009) | 0.018 (0.003) | 0.023 (0.004) | herein can be any duration that improves symptoms of a channelopathy without producing significant toxicity to the mammal. For example, the effective duration can vary from several days to several weeks, months, or years. In some cases, the effective duration for the treatment of a channelopathy can range in duration from about one month to about 10 years. Multiple factors can influence the actual effective duration used for a particular treatment. For example, an effective duration can vary with the frequency of administration, effective amount, use of multiple treatment agents, route of administration, and severity of the channelopathy being treated.

In certain instances, a course of treatment and the symptoms of the mammal being treated for a channelopathy can be monitored. Any appropriate method can be used to monitor the symptoms of a channelopathy.

The invention will be further described in the following examples, which do not limit the scope of the invention described in the claims.

EXAMPLES

Example 1: Potency-Enhancing Ligand Binding Domain Mutations

A screen was performed with a panel of 41 α7-5HT3 chimeric channels having mutant LBDs against a panel of 51 clinically used drugs with chemical similarity to nicotinic receptor agonists. Mutations were at residues highlighted in FIG. 1. The screen revealed mutations at Gln$^{79}$ in the α7

Figure 4A:
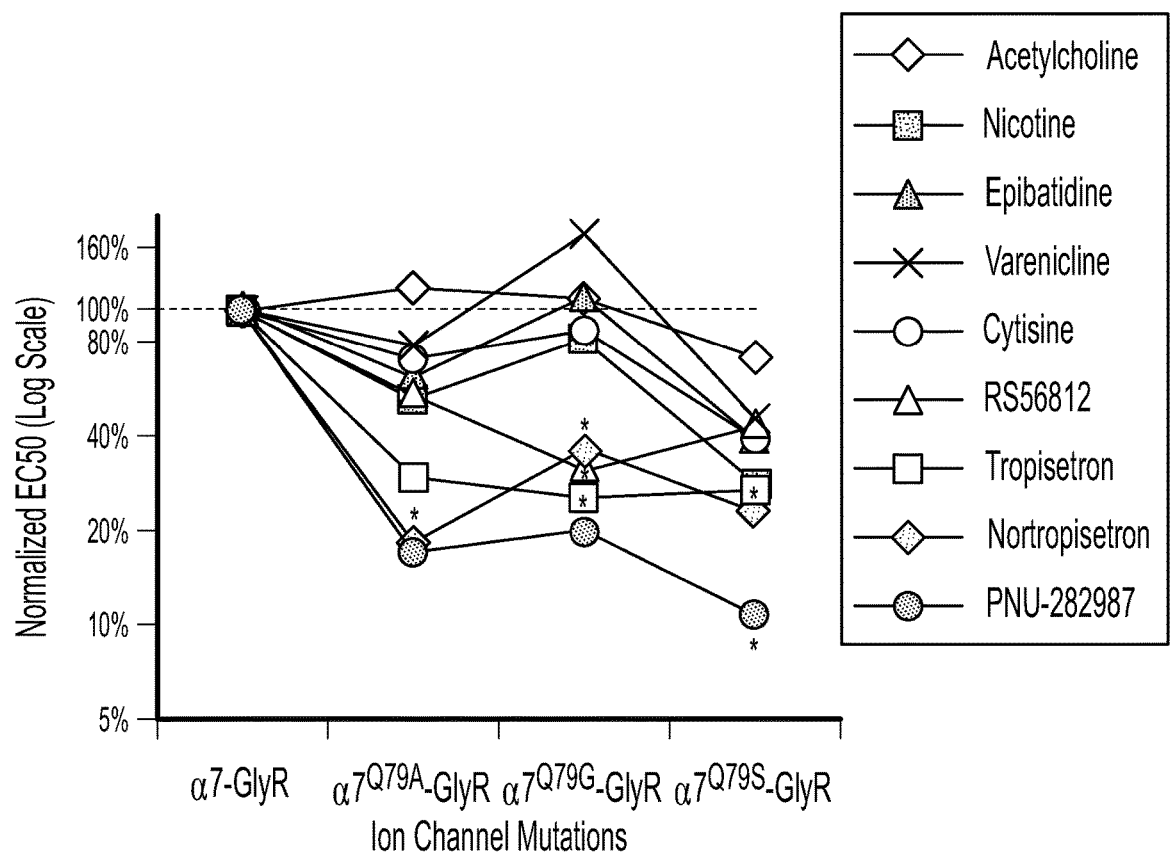
FIGS. 4A-4C show the relative potency of known nAChR agonists for α7-GlyR chimeric LGICs.
Figure 4B:
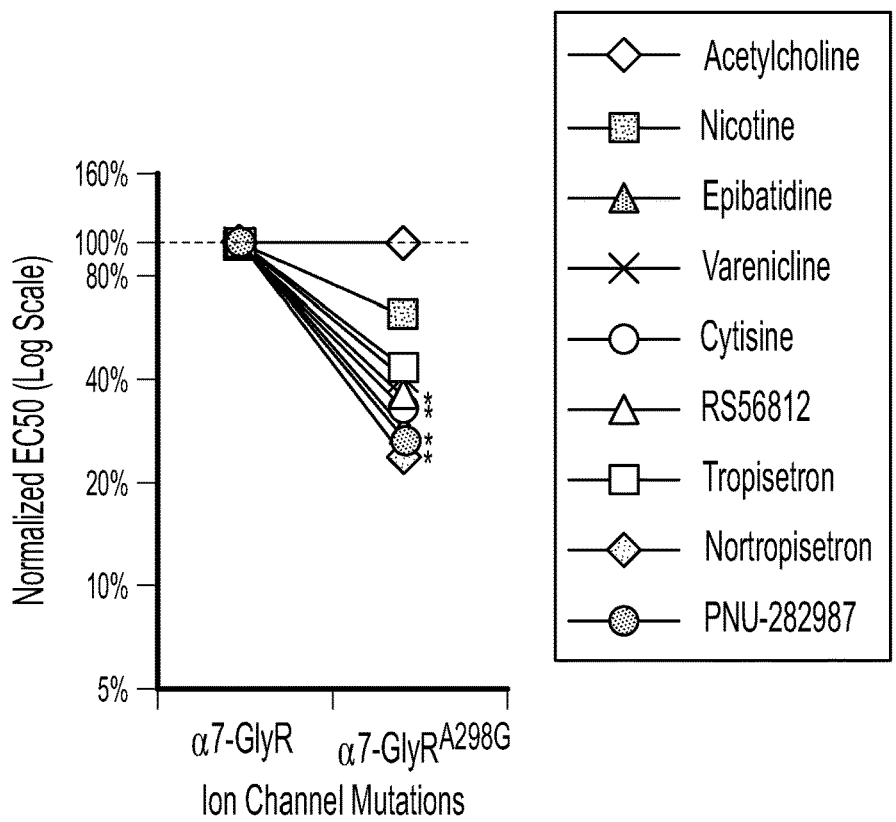
Figure 4C:
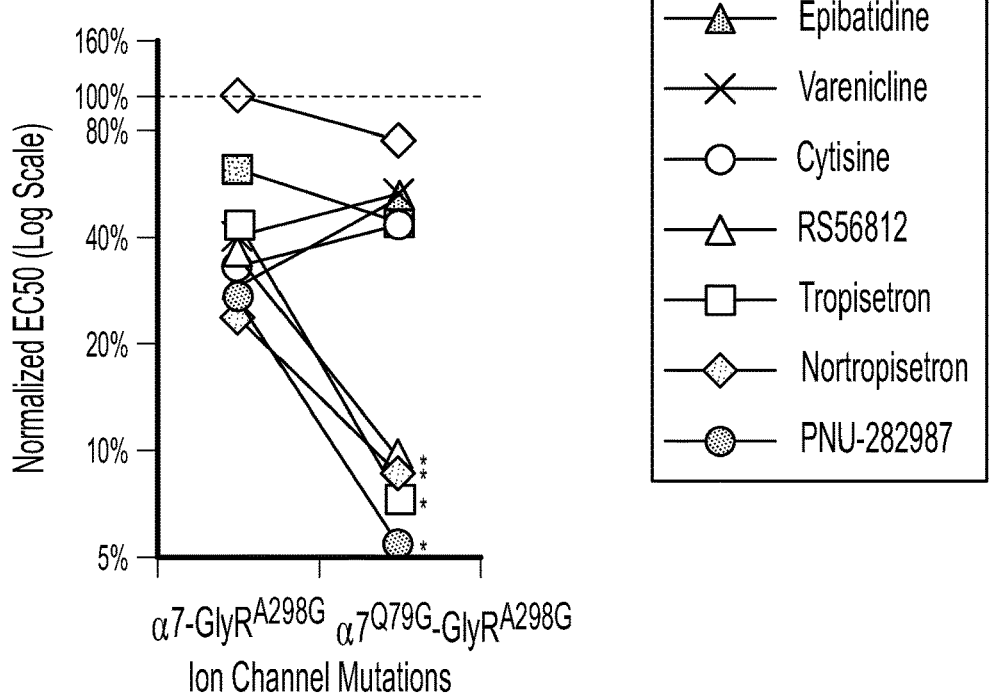
Figure 5C:
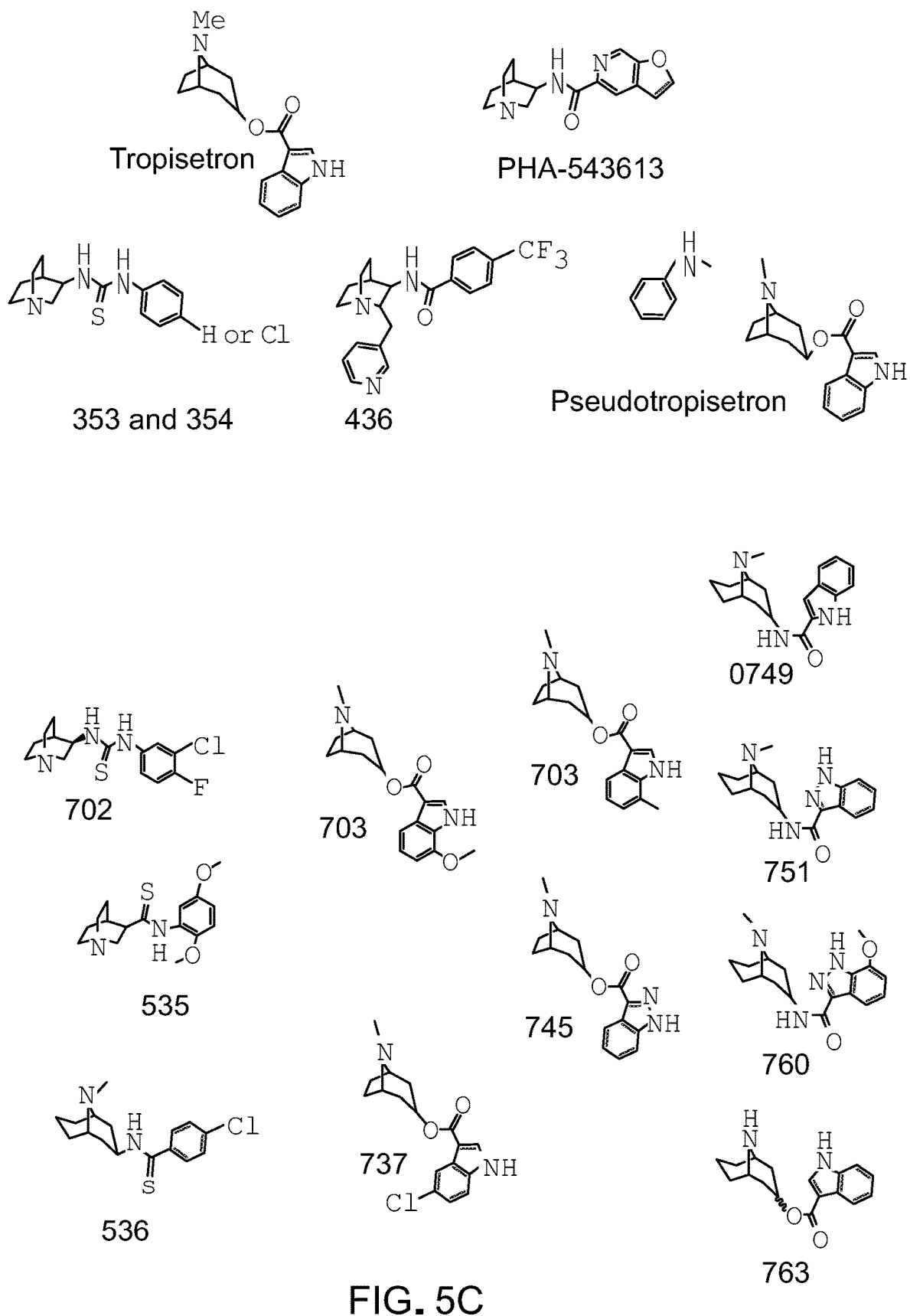

These mutated LBDs were used to generate α7-GlyR chimeric channels having enhanced potency for most of these ligands up to 6-fold (FIG. 4A). Like mutations of α7-5HT3, these mutations at Gln79 did not significantly affect potency of ACh, nicotine, epibatidine, varenicline, or cytisine. However, tropisetron, nortropisetron, and RS56812 showed significantly enhanced potency for α7$^{Q79G}$-GlyR. Similar to LBD mutations for α7-5HT3, nortropisetron had significantly enhanced potency for α7$^{Q79A}$-GlyR, and PNU-282987 showed significantly enhanced potency for α7$^{Q79S}$-GlyR. For most agonists, α7$^{Q79G}$-GlyR was the most preferred mutant chimeric ion channel.

Another relationship that was observed in the small molecule screen was that mutations at Trp77 conferred agonist activity for the drug granisetron at the α7$^{W77F}$-5HT3 (EC50: 1.2 μM), α7$^{W77Y}$-5HT3 (EC50: 1.1 and α7$^{W77F}$-GlyR (EC50: 0.66 μM) receptors. Granisetron is a 5HT3 receptor antagonist granisetron, which does not activate α7-5HT3 or α7-GlyR.

These results show that mutation of Q79 (to A, G, or S) in the α7 nAChR LBD enhanced binding of known LGIC ligands to modified LGICs.

Example 2: Potency Enhancing Ion Pore Domain Mutations

α7-GlyR channels having IPD mutations previously established in full length glycine receptor channels (T258S and A288G, GlyR numbering; equivalent to T268S and A298G for α7-GlyR numbering) were examined for enhanced potency for the allosteric agonist ivermectin. Channels having α7-GlyR$^{T268S}$ were found to have substantial ligand-free open probability, which rendered them unsuitable for ligand-controlled manipulations of cells. Mutations at α7-GlyR$^{A298G}$, which were effective for enhancing ivermectin potency at the full length glycine receptor, led to modest change in open probability in the absence of the ligand; thus this channel was examined for activity against a panel of known agonists. For canonical agonists ACh, nicotine, and epibatidine, as well as for varenicline and tropisetron, the agonist potency was not significantly enhanced in α7-GlyR$^{A298G}$. A subset of α7 nAChR agonists did show up to a modest 4-fold increase in potency: RS56812, cytisine, PNU-282987, and nortropisetron were significantly more potent. Therefore, the effect of the IPD A298G mutation improved ligand potency, but depended on ligand structure and was not as effective as mutations in the LBD.

The Q79G mutation in the LBD and the A298G IPD mutation for α7-GlyR was examined (Table 2). The double mutant chimeric channel, α7$^{Q79G}$-GlyR$^{A298G}$, led to synergistic enhancement of potency showing up to 18-fold enhancement of potency relative to α7-GlyR to α7 nAChR agonists. The enhancement from this double mutant channel was greater than that from the individual mutations for agonists RS56812, tropisetron, nortropisetron, and PNU-282987. Further underscoring the unexpected structural sensitivity of this combination of mutations, multiple agonists, such as ACh, nicotine, epibatidine, varenicline, and cytisine were not significantly changed between α7-GlyR and α7$^{Q79G}$-GlyR$^{A298G}$. Therefore, combination of the LBD mutation Q79G with the IPD mutation A298G led to a synergistic effect where potency for some but not all nicotinic agonists was greatly increased by ~10-20-fold.

TABLE 2

Potency of nAChR agonists against mutated chimeric chloride channels. Mean EC50 and SEM in parentheses (μM) for agonist activity in HEK cells expressing chimeric channels.

| Agonist | α7 GlyR | α7$^{Q79A}$-GlyR | α7$^{Q79G}$-GlyR | α7$^{Q79S}$-GlyR | α7-GlyR$^{A298G}$ | α7$^{Q79G}$-GlyR$^{A298G}$ |
|---|---|---|---|---|---|---|
| Acetylcholine | 6.4 (1.2) | 7.6 (1.7) | 7.1 (1.2) | 4.5 (1.2) | 6.4 (1.8) | 4.8 (0.5) |
| Nicotine | 5.0 (1.8) | 2.6 (0.7) | 4.1 (0.3) | 1.4 (0.4) | 3.1 (1.8) | 2.2 (0.6) |
| Epibatidine | 0.062 (0.021) | 0.038 (0.005) | 0.069 (0.011) | 0.024 (0.003) | 0.018 (0.001) | 0.032 (0.007) |
| Varenicline | 0.62 (0.2) | 0.48 (0.08) | 1.1 (0.25) | 0.28 (0.06) | 0.25 (0.04) | 0.33 (0.08) |
| Cytisine | 6.4 (2.0) | 4.5 (0.6) | 5.6 (2.1) | 2.5 (0.7) | 2.1 (0.28) | 2.8 (1.0) |
| RS56812 | 6.5 (1.8) | 3.5 (0.5) | 2.0 (0.15) | 2.8 (0.5) | 2.3 (0.1) | 0.61 (0.14) |
| Tropisetron | 0.15 (0.045) | 0.044 (0.008) | 0.038 (0.003) | 0.040 (0.009) | 0.065 (0.026) | 0.011 (0.002) |
| Nortropisetron | 0.022 (0.007) | 0.004 (0.001) | 0.008 (0.003) | 0.005 (0.001) | 0.005 (0.001) | 0.002 (0.001) |
| PNU-282987 | 0.13 (0.038) | 0.022 (0.004) | 0.026 (0.005) | 0.014 (0.002) | 0.035 (0.005) | 0.007 (0.001) |

These results show that mutation of Q79 (to A, G, or S) in the α7 nAChR LBD and/or mutation of A298 (to G) in the GlyR IPD further enhanced selective binding of known LGIC ligands to modified LGICs.

Example 3: Molecules Exhibiting Enhanced Potency

Based on the structure activity relationship of known agonists that showed enhanced potency with α7Q79G-GlyR$^{A298G}$, a variety of synthetic molecules comprised of either quinuclidine, tropane, or 9-azabicyclo[3.3.1]nonane pharmacophores with one or more aromatic side chain substituents were tested. In addition, the known α7 nAChR agonist PHA-543613 (Walker et al 2006, Wishka et al 2006) was also tested and showed exceptional potency for α7Q79G-GlyR$^{A298G}$. These molecules generally showed enhanced potency 10-fold to 100-fold (Table 3), indicating that, for these pharmacophores, a range of structural features were compatible with improved potency for α7Q79G-GlyR$^{A298G}$.

These results show that modified LGICs can be activated by synthetic quinuclidine-containing and tropane-containing LGIC ligands.

TABLE 3

Potency of compounds against chimeric channels. Mean EC50 and SEM in parentheses (μM) for agonist activity in HEK cells expressing chimeric channels. Partial refers to partial agonist activity.

| Compound | $X_1$ | $X_2$ | $X_3$ | Y | $C_1$ n | $C_2$ n | $C_3$ n | C-X config | R | A | α7-5HT3 EC$_{50}$ (μM) | α7-GlyR EC$_{50}$ (μM) | α7$^{Q79G}$-GlyR$^{A298G}$ EC$_{50}$ (μM) |
|---|---|---|---|---|---|---|---|---|---|---|---|---|---|
| PNU-282987 | N | CH$_2$ | NH | O | 0 | 1 | 0 | R | H | 4-chloro-benzene | 0.22 | 0.13 | 0.007 |
| Tropisetron | C | NMe | O | O | 1 | 0 | 0 | Endo | H | 1H-indole | 0.24 | 0.15 | 0.011 |
| Pseudo-tropisetron | C | NMe | O | O | 1 | 0 | 0 | Exo | H | 1H-indole | 2 | 0.7 | <0.2 |

TABLE 3-continued

Potency of compounds against chimeric channels. Mean EC50 and SEM in parentheses (μM) for agonist activity in HEK cells expressing chimeric channels. Partial refers to partial agonist activity.

| Compound | $X_1$ | $X_2$ | $X_3$ | Y | $C_1$ n | $C_2$ n | $C_3$ n | C-X config | R | A | α7-5HT3 EC$_{50}$ (μM) | α7-GlyR EC$_{50}$ (μM) | α7$^{Q79G}$-GlyR$^{A298G}$ EC$_{50}$ (μM) |
|---|---|---|---|---|---|---|---|---|---|---|---|---|---|
| Nortropisetron | C | NH | O | O | 1 | 0 | 0 | Endo | H | 1H-indole | 0.061 | 0.022 | 0.002 |
| PHA-543613 | N | CH$_2$ | NH | O | 0 | 1 | 0 | R | H | furo[2,3]pyridine | 0.046 | 0.039 | 0.004 |
| 0542 | C | NMe | NH | S | 1 | 0 | 0 | Endo | H | 1H-indole | 3.8 | 0.58 | 0.072 |
| 0026 | N | CH$_2$ | O | O | 0 | 1 | 0 | S | H | 4-(trifluoromethyl) benzene | — | 13.7 | 1.43 |
| 0456 | N | CH$_2$ | CH$_2$-NH | S | 0 | 1 | 0 | mix | H | 4-chloro benzene | — | 2.8 | 0.47 |
| 0434 | N | CH$_2$ | NH | O | 0 | 1 | 0 | mix | pyridin-3-ylmethyl | 2,5-dimethoxy benzene | >10 | >10 | 0.19 |
| 0436 | N | CH$_2$ | NH | O | 0 | 1 | 0 | mix | pyridin-3-ylmethyl | 4-(trifluoromethyl) benzene | 0.84 | 0.31 | 0.006 |
| 0354 | N | CH$_2$ | NH | S | 0 | 1 | 0 | R | H | 4-chloroaniline | 1.4 partial | 1.0 | 0.03 |
| 0353 | N | CH$_2$ | NH | O | 0 | 1 | 0 | S | H | aniline | 0.65 | 0.27 | 0.01 |
| 0295 | N | CH$_2$ | NH | O | 0 | 1 | 0 | S | H | 5-(trifluoromethyl) pyridin-2-yl | >100 | >100 | 4.6 |
| 0296 | N | CH$_2$ | NH | O | 0 | 1 | 0 | S | H | 6-(trifluoromethyl) nicotinic | >100 | — | 0.45 |
| 0536 | C | NMe | NH | S | 1 | 0 | 1 | Endo | H | 4-chloro-benzene | >33 | >100 | 9.1 |
| 0676 | N | CH$_2$ | NH | O | 0 | 1 | 0 | S | H | 1H-indole | 0.03 | 0.018 | 0.002 |

Example 4: Mutations that Reduce Acetylcholine Responsiveness

The α7 nAChR has relatively low sensitivity to ACh compared to other nAChR isoforms, and potency enhancing mutations for tropane and quinuclidine ligands did not substantially alter the potency of acetylcholine at these channels. Thus, the chimeric channels were further modified to reduce acetylcholine responsiveness of these channels. Acetylcholine responsiveness was considerably reduced to more than 100 μM in some cases with additional LBD mutations Y115F and Q139G that that only modestly reduced the potency of some agonists for α7$^{Q79G,Y115F}$-5HT3, α7$^{Q79G,Q139G}$-5HT3, α7$^{Q79G,Q139G}$-GlyR$^{A298}$, α7$^{Q79G,Y115F}$-GlyR$^{A298G}$. For example, α7$^{Q79G,Y115F}$-GlyR$^{A298G}$ has an EC50 of 13 nM for nortropisetron and >100 μM for ACh (Table 4).

TABLE 4

Potency of nAChR agonists against mutated chimeric chloride channels with low acetylcholine responsiveness. Mean EC50 and SEM in parentheses (μM) for activity in HEK cells expressing chimeric channels.

| | α7$^{Q79G, Y115F}$-5HT3 | α7$^{Q79G, Q139G}$-5HT3 | α7$^{Q79G, Y115F}$-GlyR$^{A298G}$ | α7$^{Q79G, Q139G}$-GlyR$^{A298G}$ | α7$^{R27D, E41R, Q79G, 115F}$-GlyR$^{A298G}$ |
|---|---|---|---|---|---|
| Acetylcholine | >100 | 36 (2) | >100 | 73 (27) | >100 |
| Nicotine | 34 (4) | 24 (4) | 22 (3) | 30 (8) | 7.5 (1.3) |
| Tropisetron | 0.10 (0.12) | 0.31 (0.06) | 0.086 (0.043) | 0.26 (0.04) | 0.035 (0.021) |
| Nortropisetron | 0.028 (0.005) | 0.047 (0.013) | 0.013 (0.001) | 0.031 (0.006) | 0.003 (0.001) |
| PNU-282987 | 0.35 (0.07) | 0.16 (0.04) | 0.22 (0.04) | 0.18 (0.04) | 0.066 (0.010) |

These results show that Y115F and/or Q139G mutations in the α7 nAChR LBD reduced binding of the endogenous LGIC ligand Ach to the modified LGIC.

Figure 6A:
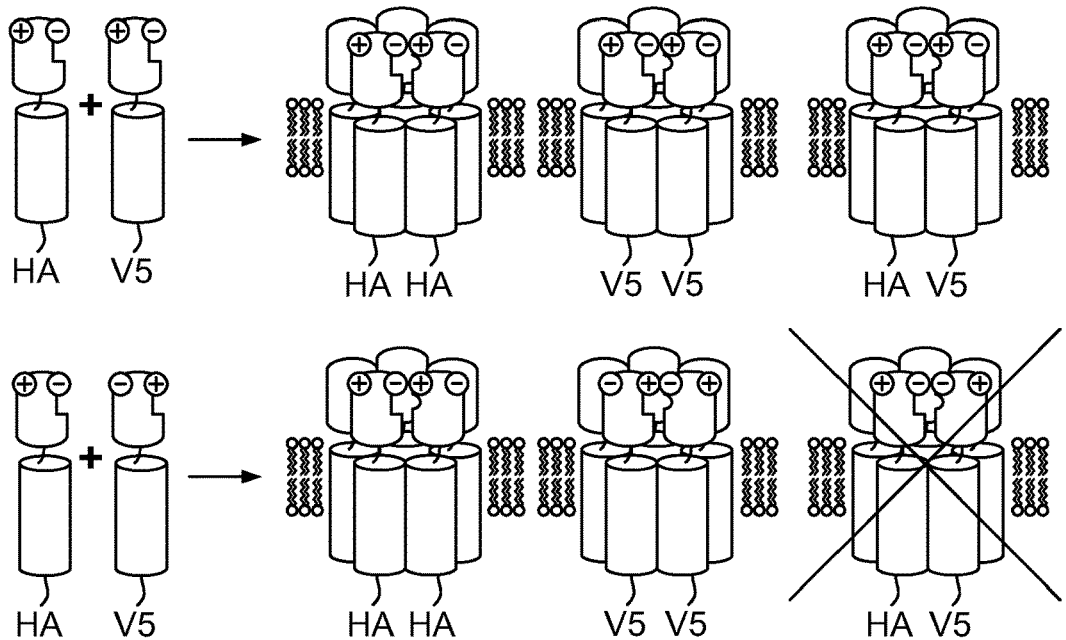
FIG. 6C) Association of α7-5HT3 LGICs with HA and V5 epitope tags in HEK cells was probed by HA immunoprecipitation (left) or total lysate isolation followed by western blotting with either anti-HA (top) or anti-V5 antibodies (bottom). In cells co-expressing channels with the HA and V5 epitopes, anti-HA IP followed by anti-V5 immunoblotting shows the co-immunoprecipation of unmodified channels of each type, but charge reversal mutations in the LBD α7$^{R27D,E41R}$-5HT3-V5 was not immunoprecipitated. MW of α7-5HT3 is ~48 kD (arrow).
Figure 6B:
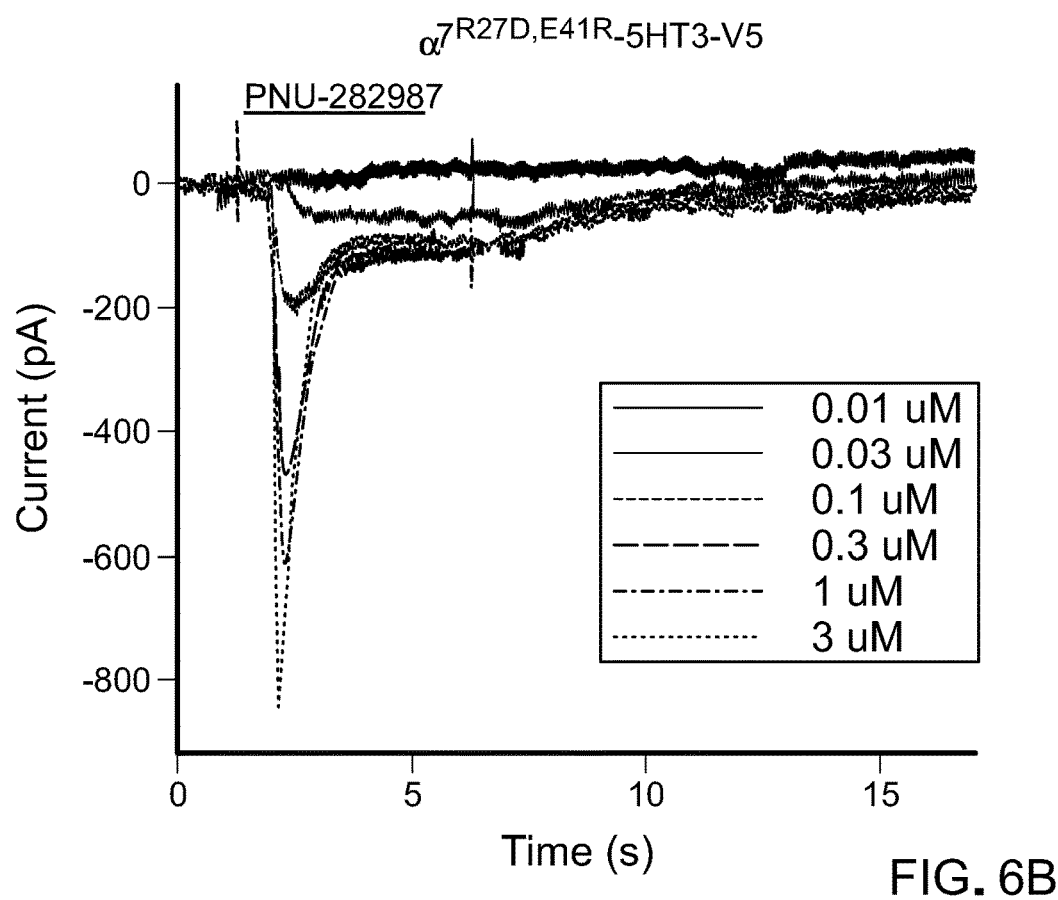
Figure 6C:
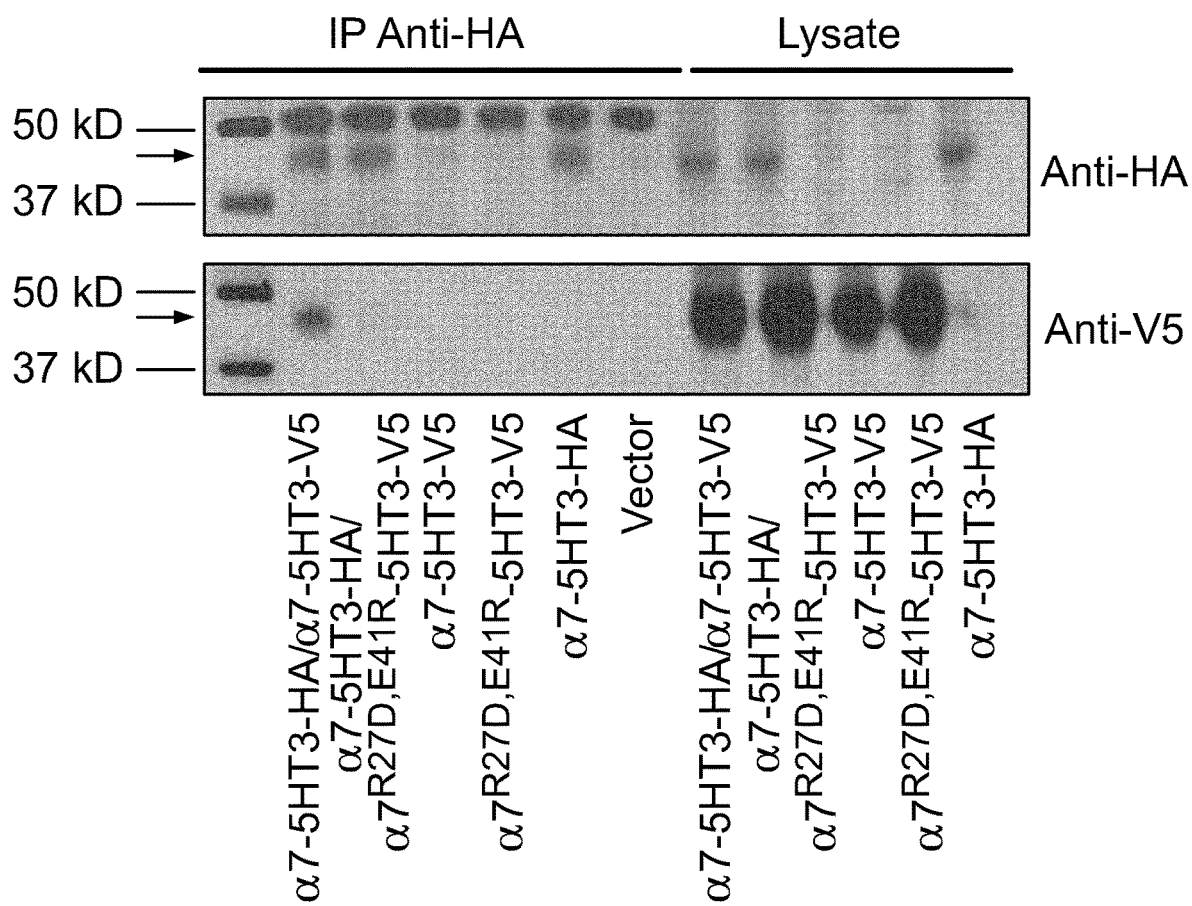

Example 5: Mutations that Reduce Associations with Endogenous Receptor Subunits Assembly of α7 nAChRs is based on associations of five homomeric subunits through interactions between the LBDs (Celie et al 2004 Neuron 41: 907-14). To minimize undesired associations with endogenous α7 nAChR subunits and/or unwanted associations of chimeric channels, potential inter-subunit salt bridges were identified by examining the crystal structure of the acetylcholine binding protein and identifying nearby inter-subunit residues with opposite charge that also have homologous ionic amino acids in the α7 nAChR receptor LBD. Charge reversal mutations (switching the acidic member of a potential salt bridge to a basic residue and its basic partner to an acidic residue) were designed to disrupt inter-subunit interactions with unmodified subunits but preserve interactions between the subunits with charge reversal mutations (FIG. 6A). Chimeric LGIC subunits having charge reversal mutations were able to assemble selectively with each other without interacting with unmodified channels, e.g. endogenous α7 nAChR. The double mutation of R27D,E41R in the α7 nAChR LBD resulted in functional channels (FIG. 6B). Co-expression of these charge reversal channels with α7-5HT3 channels having an unmodified sequence showed that the charge reversal subunits did not co-immunoprecipitate with unmodified channels (FIG. 6C). Combination with potency enhancing mutations and acetylcholine blocking mutations to give the chimeric channel $α7^{R27D,E41R,Q79G,Y115F}$-$GlyR^{A298G}$ revealed that some agonists retained high potency for their cognate agonist (Table 4, right column).

These results show that R27D and E41R mutations in α7 nAChR LBD reduced association of the modified LGIC subunits with other modified and/or endogenous LGIC subunits.

Example 6: LBD Mutations that Increase Ligand Potency

Mutations in $Gly^{175}$ and $Pro^{216}$ of the α7 nAChR LBD in α7-GlyR chimeric channels were tested. Mutation of $Gly^{175}$ to Lys ($α7^{G175K}$-GlyR) showed increased potency for ACh (5-fold) (Table 5). For $α7^{G175K}$-GlyR, it was also found that nicotine potency was enhanced 10-fold relative to the unmodified α7-GlyR chimeric channel (Table 5). Mutation of $Pro^{216}$ to Ile ($α7^{P216I}$-GlyR) did not substantially alter ACh potency (Table 5). However, $α7^{P216I}$-GlyR showed increased nicotine potency by >4-fold relative to unmodified α7-GlyR (Table 5). These potency enhancing mutations in $α7^{G175K}$-GlyR and $α7^{P216I}$-GlyR also affected potency of several other α7-GlyR agonists up to 30-fold (Table 5). For $α7^{G175K}$-GlyR, greater than 10-fold potency enhancement over α7-GlyR was seen for the clinically used drugs tropisetron, varenicline, cytisine, granisetron, and epibatidine. For $α7^{P216I}$-GlyR, potency enhancement was approximately 3-fold (Table 5).

TABLE 5

Agonist potency enhancement by G175K and P216I mutations at a7GlyR chimeric channels.

| Compound | a7GlyR | α7GlyR G175K | α7GlyR P216I | α7GlyR Y115F G175K | α7GlyR G175K Y210F | α7GlyR W77F G175K | α7GlyR Q79G G175K | α7GlyR W77F Q79G G175K | α7GlyR W77F Y115F G175K | α7GlyR W77F G175K Y210F |
|---|---|---|---|---|---|---|---|---|---|---|
| Acetylcholine | 6.4 (1.2) | 1.2 (0.41) | 4.0 (0.5) | 52 (6.6) | 93 (1.3) | 6.8 (1.6) | 4.5 (1.3) | 41 (3.1) | 143 (13) | 80 (31) |
| Nicotine | 5.0 (1.8) | 0.5 (0.25) | 1.4 (0.1) | 4.1 (1.4) | 6 (0.5) | 1.3 (0.4) | 1.1 (0.1) | 2.6 (0.7) | 6.1 (2.0) | 4.2 |
| Epibatidine | 0.062 (0.021) | 0.005 (0.001) | 0.03 (0.01) | 0.036 (0.006) | 0.65 (0.11) | 0.04 (0) | 0.037 (0.013) | 2.6 (2.3) | 0.33 | 0.38 |
| Varenicline | 0.62 (0.2) | 0.056 (0.014) | 0.18 (0.06) | 5.0 (1.7) | 4.3 (0.6) | 0.57 (0.18) | 0.42 (0.1) | 3.3 (1.0) | >10 | >9 |
| Cytisine | 6.4 (2.0) | 0.4 (0.05) | 1.9 (0.2) | 7.1 (1.2) | >10 | 1.5 (0.6) | 2.5 (1.1) | 6.9 (1.2) | 4.02 | 5.1 |
| PNU-282987 | 0.13 (0.038) | 0.005 (0.001) | 0.04 (0.004) | 0.1 (0.01) | 0.7 (0.3) | 0.67 (0.35) | 0.06 (0.05) | 0.5 (0.2) | >1 | >40 |
| Tropisetron | 0.15 (0.045) | 0.011 (0.002) | 0.05 (0.003) | 0.027 (0.004) | 1.1 (0.2) | 0.04 (0.01) | 0.01 (0.001) | 0.024 (0.004) | 0.1 (0.04) | >1 |
| Nortropisetron | 0.022 (0.007) | 0.003 (0.002) | 0.006 (0.0004) | 0.007 (0.001) | 0.28 (0.09) | 0.004 (0.001) | 0.0008 (0.0001) | 0.0026 (0.0004) | 0.014 | >12 |
| PHA-543613 | 0.03 (0.01) | 0.001 (0.0001) | 0.009 (0.001) | 0.02 (0.007) | 0.26 (0.08) | 0.041 (0.016) | 0.003 (0.0004) | 0.12 (0.04) | >0.3 | >3 |
| Granisetron | >100 | 3.3 (0.1) | 6.1 (0.9) | 1.6 (0.6) | 1.4 (0.1) | 0.18 (0.02) | >100 | 1.6 (0.4) | 0.2 | 0.06 (0.01) |
| Ivermectin | nd | nd | nd | nd | nd | nd | nd | nd | nd | 0.21 |

| Compound | α7GlyR Q79G Y115F | α7GlyR Q79G Y115F Y210F | α7GlyR Q79G Y115F K322L | α7GlyR Y115F L141F G175K | α7GlyR Q79G Q139L G175K |
|---|---|---|---|---|---|
| Acetylcholine | 98 (10) | >1000 | >200 | 58 | 53 |
| Nicotine | 13 (0.2) | >100 | 14.5 | 3 | 5.8 |
| Epibatidine | 0.22 (0.015) | >10 | 0.27 | 0.144 | 0.144 |

TABLE 5-continued

Agonist potency enhancement by G175K and P216I mutations at α7GlyR chimeric channels.

| | | | | | |
|---|---|---|---|---|---|
| Varenicline | >10 | >30 | >30 | >8.1 | 0.96 |
| Cytisine | >10 | >30 | >30 | 4.74 | 3.24 |
| PNU-282987 | 0.08 (0.01) | >1 | 0.018 | 0.51 | 0.05 |
| Tropisetron | 0.027 (0.002) | 0.717 | 0.066 | 0.117 | 0.105 |
| Nortropisetron | 0.012 (0.001) | >0.3 | 0.069 | 0.075 | 0.001 |
| PHA-543613 | 0.036 (0.006) | >1 | 0.111 | 0.057 | 0.024 |
| Granisetron | 6.8 (1.7) | 4.8 | >30 | 0.84 | >30 |
| Ivermectin | nd | nd | nd | nd | | nd = not determined

For use in organisms that produce ACh, it is important to reduce the endogenous ACh potency at these channels comprised of the α7 nAChR LBD. Mutation G175K could be further combined with other mutations that reduced sensitivity to ACh, such as Y115F and Y210F. For α7$^{Y115F,G175K}$-GlyR, high potency for agonists based on tropane or quinuclidine core structures were found for tropisetron, granisetron, nortropisetron, PNU-282987, and PHA-543613, and greatly reduced potency for varenicline and cytisine (Table 5). For α7$^{G175K,Y210F}$-GlyR, potency for most agonists was considerably reduced, however potency enhancement for granisetron was observed (Table 5).

To develop channels with reduced ACh responsiveness but high potency for other agonists, α7$^{G175K}$-GlyR was combined with additional mutations that increase the potency of specific agonists. Combination with W77F reduced ACh potency, and α7$^{W77F,G175K}$-GlyR showed increased potency over α7-GlyR for granisetron, nortropisetron, and tropisetron but not for PNU282-987, varenicline, cytisine, or PHA-543613 (Table 5). Combination of G175K with Q79G reduced ACh potency, and α7$^{Q79G,G175K}$-GlyR showed increased potency for nortropisetron, PHA-543613, and tropisetron (Table 5). However, this potency enhancement was not observed for other agonists, such as PNU282-987, or varenicline. α7$^{G175K,Q139L}$-GlyR reduced ACh potency and increased potency for nortropisetron and tropisetron (Table 5).

Further reductions in ACh potency were achieved while maintaining high potency for with synthetic agonists, including those based on tropane and quinuclidine core structures, by incorporating mutations at W77F, Q79G, L141F, Y115F, G175K, and Y210F in various combinations. α7$^{Q79G,Y115F,G175K}$-GlyR reduced ACh responsiveness while maintaining potent responses to tropisetron (Table 5). These mutations also enhanced responsiveness to other tropane and quinuclidine core structures relative to α7$^{Y115F,G175K}$-GlyR as well as relative to α7-5HT3 (representative of endogenous α7 nAChR activity), especially quinuclidine thioureas 702 and 703 as well as tropane ester 723, 725, 726, 736, 737, 738, and 745 (Table 6). α7$^{Q79G,Y115F,G175K}$-GlyR also showed high sensitivity to ivermectin (Table 5). α7$^{W77F,Q79G,G175K}$-GlyR reduced ACh responsiveness while maintaining high potency responses to tropisetron, and nortropisetron (Table 5). α7$^{W77F,Q79G,G175K}$-GlyR also showed enhanced potency for additional tropane-based core structures, such as compounds 723 and 725, as well as the clinically used drugs mequitazine and promazine (Table 6). α7$^{W77F,G175K,Y210F}$-GlyR reduced ACh responsiveness but markedly improved potency to granisetron (Table 5). α7$^{L141F,Y115F,G175K}$-GlyR reduced ACh responsiveness while conferring sensitivity to granisetron (Table 5). α7$^{Q79G,Q139L,G175K}$-GlyR reduced ACh responsiveness but showed potent responses to nortropisetron (Table 5).

TABLE 6

Potency enhancement of tropane, quniuclidine agonists, 9-azabicyclo[3.3.1]nonane agonists, diazabicyclo[3.2.2]nonane agonists, and promazine by G175K and P216I α7GlyR chimeric channels. Indole and indazole aromatic (A) substituents attached at 3-position.

| Agonist class | $X_1$ | $X_2$ | $X_3$ | Y | $C_1$ n | $C_2$ n | $C_3$ n | C-X configuration | R | Aromatic substitution A |
|---|---|---|---|---|---|---|---|---|---|---|
| Quinuclidine | N | $CH_2$ | NH | S | 0 | 1 | 0 | R | H | 3,5-dichloro-aniline |
| Quinuclidine | N | $CH_2$ | NH | S | 0 | 1 | 0 | R | H | 3,4-dichloro-aniline |
| Quinuclidine | N | $CH_2$ | NH | S | 0 | 1 | 0 | R | H | 4-(trifluoromethoxy)aniline |
| Quinuclidine | N | $CH_2$ | NH | S | 0 | 1 | 0 | R | H | 4-fluoroaniline |
| Quinuclidine | N | $CH_2$ | NH | S | 0 | 1 | 0 | R | H | 3-chloro-aniline |
| Quinuclidine | N | $CH_2$ | NH | S | 0 | 1 | 0 | R | H | 3-chloro-2-fluoroaniline |
| Quinuclidine | N | $CH_2$ | NH | S | 0 | 1 | 0 | R | H | 3-chloro-4-fluoroaniline |
| Quinuclidine | N | $CH_2$ | NH | S | 0 | 1 | 0 | R | H | 5-chloro-2-fluoroaniline |

TABLE 6-continued

Potency enhancement of tropane, quniuclidine agonists, 9-azabicyclo[3.3.1]nonane agonists, diazabicyclo[3.2.2]nonane agonists, and promazine by G175K and P216I α7GlyR chimeric channels. Indole and indazole aromatic (A) substituents attached at 3-position.

| | | | | | | | | | | |
|---|---|---|---|---|---|---|---|---|---|---|
| Quinuclidine | N | $CH_2$ | NH | S | 0 | 1 | 0 | R | H | 3-chloro-4-methylaniline |
| Quinuclidine | N | $CH_2$ | NH | S | 0 | 1 | 0 | R | H | 5-chloro-2-methylaniline |
| Quinuclidine | N | $CH_2$ | NH | S | 0 | 1 | 0 | S | H | 4-(trifluoromethoxy) aniline |
| Tropane | C | NMe | NH | S | 1 | 0 | 0 | Endo | H | 1-methyl-1H-indole |
| Tropane | C | NMe | O | O | 1 | 0 | 0 | Endo | H | 4-methoxy-1H-indole |
| Tropane | C | NMe | O | O | 1 | 0 | 0 | Endo | H | 6-methoxy-1H-indole |
| Tropane | C | NMe | O | O | 1 | 0 | 0 | Endo | H | 7-methoxy-1H-indole |
| Tropane | C | NMe | O | O | 1 | 0 | 0 | Endo | H | 4-methyl-1H-indole |
| Tropane | C | NMe | O | O | 1 | 0 | 0 | Endo | H | 7-methyl-1H-indole |
| Tropane | C | NMe | O | O | 1 | 0 | 0 | Endo | H | 4-chloro-1H-indole |
| Tropane | C | NMe | O | O | 1 | 0 | 0 | Endo | H | 5-methoxy-1H-indole |
| Tropane | C | NMe | O | O | 1 | 0 | 0 | Endo | H | 5-chloro-1H-indole |
| Tropane | C | NMe | O | O | 1 | 0 | 0 | Endo | H | 6-chloro-1H-indole |
| Tropane | C | NMe | O | O | 1 | 0 | 0 | Endo | H | 1H-indazole |
| 9-azabicyclo [3.3.1]nonane | CH | NMe | NH | O | 1 | 0 | 1 | Endo | H | 1H-indole |
| 9-azabicyclo [3.3.1]nonane | CH | NMe | NH | O | 1 | 0 | 1 | Endo | H | 1H-indazole |
| 9-azabicyclo [3.3.1]nonane | CH | NMe | NH | O | 1 | 0 | 1 | Endo | H | 7-methoxy-1H-indazole |
| 9-azabicyclo [3.3.1]nonane | CH | NH | O | O | 1 | 0 | 1 | Endo | H | 1H-indole |
| 1,4-diazabicyclo [3.2.2]nonane | | | | | | | | | F | dibenzo[b,d] thiophene 5,5-dioxide |
| 1,4-diazabicyclo [3.2.2]nonane | | | | | | | | | $NO_2$ | dibenzo[b,d] 5,5-dioxide |
| Quinuclidine | N | $CH_2$ | $CH_2$ | | 0 | 1 | 0 | R | H | 10H-phenothiazine |
| N,N-dimethylpropyl amine | | | | | | | | | | 10H-phenothiazine |

| Agonist class | Compound | a7-5HT3 | a7-GlyR | a7GlyR G175K | a7GlyR Q79G G175K | a7GlyR Y115F G175K | a7Gly Q79G G175K Y115F | a7GlyR Q79G G175K Y115F R27D E41R | a7GlyR W77F Q79G G175K |
|---|---|---|---|---|---|---|---|---|---|
| Quinuclidine Quinuclidine | 677 | 10.6 | 4.4 | 0.66 (0.06) | 0.86 (0.004) | 3.7 (0.7) | 0.98 (0.09) | 0.58 (0.14) | nd |
| Quinuclidine | 682 | >100 | 0.2 | 0.12 (0.1) | 0.013 (0.001) | 0.40 (0.01) | 0.13 (0.01) | 0.06 (0.012) | nd |
| Quinuclidine Quinuclidine | 684 | >100 | 1.6 | 0.23 (0.02) | 0.078 (0.022) | 3.0 (0.3) | 0.79 (0.04) | 0.4 (0.03) | nd |
| Quinuclidine | 699 | 2.8 | 3.6 | 0.26 (0.11) | 0.039 (0.009) | 2.9 | 0.52 (0.09) | 0.33 (0.1) | nd |
| Quinuclidine | 700 | 1.8 | 1.9 | 0.081 (0.009) | 0.012 (0.0002) | 1.5 | 0.21 (0.04) | 0.11 (0.02) | nd |
| Quinuclidine | 701 | >100 | nd | 0.47 (0.17) | 0.086 (0.014) | 5.46 | 1.0 (0.2) | 0.58 (0.03) | nd |
| Quinuclidine | 702 | >100 | 0.9 | 0.12 (0.004) | 0.018 (0.003) | 1.6 | 0.17 (0.03) | 0.12 (0.02) | nd |
| Quinuclidine | 703 | >100 | nd | 0.52 (0.08) | 0.03 (0.01) | 12.7 | 1.2 (0.06) | 1.1 (0.5) | nd |
| Quinuclidine | 704 | 0.7 | nd | 0.062 (0.008) | 0.018 (0.002) | 0.76 (0.01) | 0.24 (0.02) | 0.18 (0.06) | nd |
| Tropane Tropane | 705 | >100 | nd | 9.6 | 0.67 (0.14) | >10 | 4.8 (1.4) | 4.5 (2.7) | nd |

TABLE 6-continued

Potency enhancement of tropane, quniuclidine agonists, 9-azabicyclo[3.3.1]nonane agonists, diazabicyclo[3.2.2]nonane agonists, and promazine by G175K and P216I α7GlyR Additional amino acid substitutions at $Gly^{175}$ of the α7 nAChR LBD in $α7^{Y115F}$-GlyR chimeric channels are also enhanced agonist potency. Potency for tropisetron at $α7^{Y115F}$-GlyR chimeric channels was enhanced with additional mutations, which include G175A (7.1-fold), G175F (2-fold), G175H (2.3-fold), G175K (5.6-fold), G175M (2.6-fold), G175R (5.8-fold), G175S (9.3-fold), G175V (16.7-fold).

TABLE 8

Agonist potency enhancement by G175 mutations at a7GlyR Y115F chimeric channels.

| Compound | α7G1yR | α7GlyR Y115F G175K | α7GlyR Y115F G175A | α7GlyR Y115F G175F | α7GlyR Y115F G175H | α7GlyR Y115F G175M | α7GlyR Y115F G175R | α7GlyR Y115F G175S | α7GlyR Y115F G175V |
|---|---|---|---|---|---|---|---|---|---|
| Acetylcholine | 6.4 (1.2) | 52 (6.6) | 24 | 67 | 79 | 71 | 29.5 | 31.5 | 15 |
| Varenicline | 0.62 (0.2) | 5.0 (1.7) | 5.9 | 13.6 | 12.7 | 14.1 | 7.6 | 9.7 | 4.6 |
| Tropisetron | 0.15 (0.045) | 0.027 (0.004) | 0.021 | 0.074 | 0.064 | 0.057 | 0.024 | 0.016 | 0.009 |
| PHA-543613 | 0.03 (0.01) | 0.02 (0.007) | 0.027 | 0.173 | 0.12 | 0.25 | 0.11 | 0.12 | 0.037 | nd = not determined; parentheses: SEM

Figure 9A:
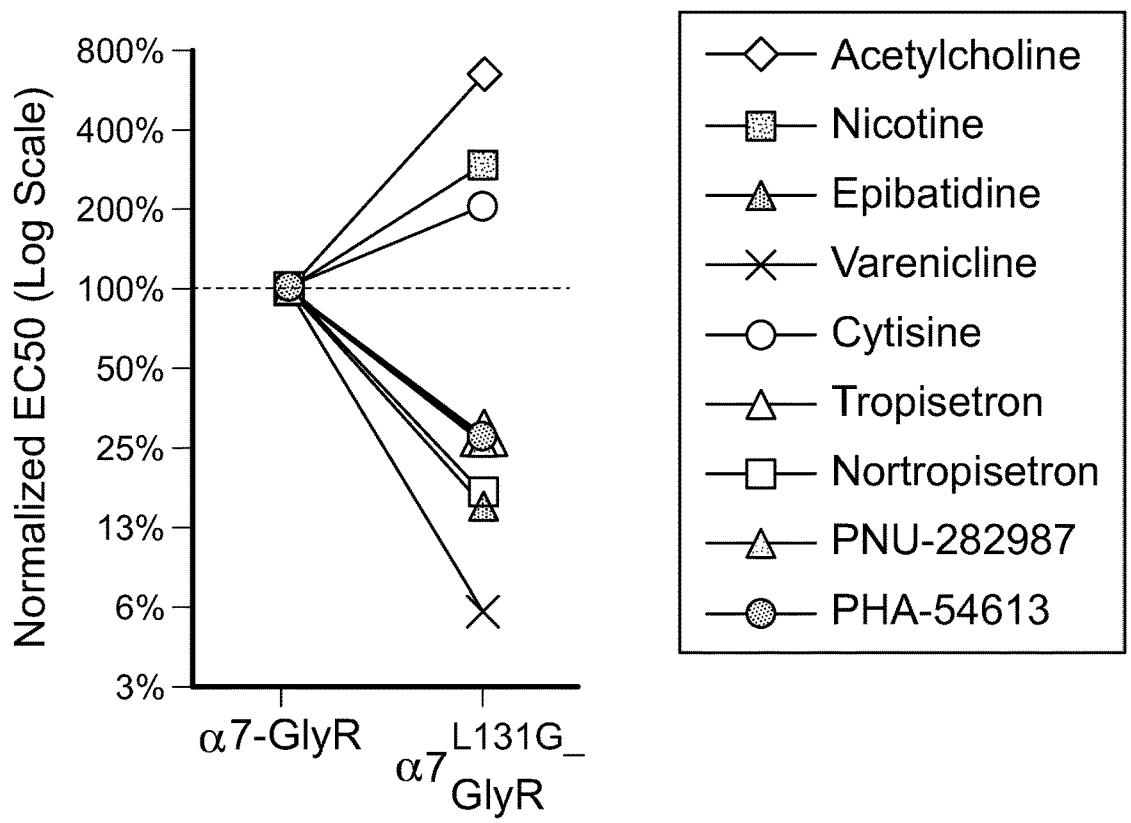
FIGS. 9A-9D show activity of agonists on chimeric LGICs with a L131G mutation.
Figure 9B:
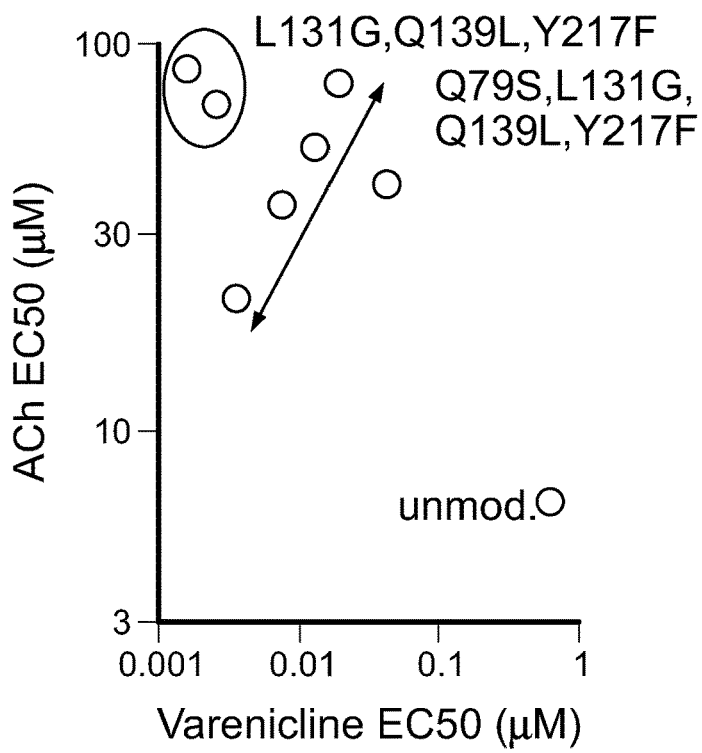

Mutations for $Leu^{131}$ to smaller amino acids were found to reduce the potency of canonical agonists ACh and nicotine, while markedly increasing potency of varenicline, tropisetron and several other agonists. $α7^{L131A}$-GlyR and $α7^{L131G}$-GlyR had reduced ACh responsiveness (6-fold) and enhanced potency for varenicline (8-fold and 17-fold, respectively) and tropisetron (2.5-fold and 3.6-fold, respectively) (Table 9). $α7^{L131G}$-5HT3 HC had reduced ACh responsiveness (5-fold) and enhanced potency for varenicline (16-fold) and tropisetron (2.3-fold) (FIG. 9A and Table 9). $α7^{L131G,Q139L}$-GlyR and $α7^{L131G,Y217F}$-GlyR showed similar potency enhancement over α7-GlyR for varenicline (21-fold) but also reduced ACh sensitivity (−11-fold and −13-fold, respectively). $α7^{Q79S,L131G}$-GlyR further improved potency over α7-GlyR for varenicline (89-fold) and tropisetron (15-fold). $α7^{L131G,Q139L,Y217F}$-GlyR showed the greatest improvement in potency over α7-GlyR for varenicline (387-fold) and also showed reduced ACh potency (13-fold) (FIG. 9B and Table 9). $α7^{L131G,Q139L,Y217F}$-GlyR also showed extremely high potency for compound 770 (0.001 μM), compound 773 (0.00034 μM), and compound 774 (0.00013 μM) (FIG. 10). $α7^{Q79S,L131G,Q139L}$-GlyR also improved potency over α7-GlyR for varenicline (31-fold) and tropisetron (3-fold) but reduced ACh potency (9-fold) (FIG. 9B and Table 9). $α7^{L131M}$-GlyR, $α7^{L131Q}$-GlyR, and $α7^{L131V}$-GlyR reduced ACh potency but enhanced potency to tropisetron, nortropisetron, PHA-543613, and granisetron (Table 9). $α7^{L131F}$-GlyR was found to substantially reduced ACh potency but did not improve potency for other agonists (Table 8). $α7^{L131G}$-GABAc substantially reduced ACh potency but did not improve potency for other agonists (Table 9). $α7^{L131G,Q139L,Y217F}$-5HT3 HC (Table 9) improved varenicline potency by 131-fold over a7-5HT3 (Table 1). $α7^{L131G,Q139L,Y217F}$-5HT3 HC also showed high potency for compound 770 (0.007 μM), compound 773 (0.002 μM), and compound 774 (0.004 μM) (Table 8).

TABLE 9

Agonist potency enhancement by chimeric channels with L131 mutations.

| Compound | α7GlyR | α7GlyR L131A | α7GlyR L131G | α7GlyR L131G Q139L | α7GlyR L131G Y217F | α7GlyR L131G Q139L Y217F | α7GlyR Q79G L131G | α7GlyR Q79S L131G | α7GlyR Q79S L131G Q139L | α7GlyR L131G D219A |
|---|---|---|---|---|---|---|---|---|---|---|
| Acetylcholine | 6.4 (1.2) | 42 (21) | 41 (11) | 68 | 85 | 83 (20) | >500 (3.5) | 21 | 58 | 210 (32) |
| Nicotine | 5.0 (1.8) | 8.0 (3.2) | 15 (3.5) | 26 | 28 | 55 (18) | >100 | 8.2 (0.8) | 25 | 36 |
| Epibatidine | 0.062 (0.021) | 0.027 | 0.009 (0.004) | 0.012 | 0.015 | 0.021 (0.002) | nd | 0.007 (0.001) | 0.012 | 0.16 |
| Varenicline | 0.62 (0.2) | 0.082 (0.068) | 0.037 (0.026) | 0.03 | 0.03 (0.001) | 0.0016 | >10 (0.001) | 0.007 | 0.02 | 0.78 (1.1) |
| Cytisine | 6.4 (2.0) | 20.6 (9.4) | 13.1 (0.66) | 12 | 30 | nd | >30 | 8.1 (0.3) | 10 | >30 |
| PNU-282987 | 0.13 (0.038) | 0.055 (0.025) | 0.034 (0.008) | 0.063 | 0.054 (0.03) | 0.16 | 0.096 (0.002) | 0.006 | 0.018 | 0.41 (0.04) |
| Tropisetron | 0.15 (0.045) | 0.06 (0.021) | 0.042 (0.01) | 0.13 | 0.087 | 0.31 (0.05) | 0.09 | 0.01 (0.003) | 0.045 | 0.36 |
| Nortropisetron | 0.022 (0.007) | 0.006 (0.003) | 0.004 (0.001) | 0.024 | 0.018 (0.006) | 0.047 | 0.012 (0.002) | 0.004 | 0.006 | 0.07 (0.008) |
| PHA-543613 | 0.03 (0.01) | 0.012 (0.006) | 0.008 (0.002) | 0.021 | 0.016 | 0.045 (0.008) | 0.066 | 0.002 (0.0005) | 0.009 | 0.038 |
| Granisetron | >100 | 17.2 (12.8) | 6.7 (1.6) | 4 | 4 | nd | nd | 4.2 (0.8) | nd | >30 |

TABLE 9-continued

Agonist potency enhancement by chimeric channels with L131 mutations.

| | | | | | | | | | | |
|---|---|---|---|---|---|---|---|---|---|---|
| 765 | >100 | nd | nd | nd | nd | 0.031 (0.02) | 0.027 | 0.024 | nd | nd |
| 770 | nd | nd | nd | nd | nd | 0.001 (0.0003) | nd | nd | nd | nd |
| 773 | 0.001 | nd | 0.00013 | 0.00004 | nd | 0.00034 | 0.00004 | nd | nd | nd |
| 774 | 0.006 | nd | 0.00004 | 0.00004 | nd | 0.00018 | 0.00004 | nd | nd | nd |

| Compound | α7GlyR L131F | α7GlyR Q79S L131G Q139L Y217F | α7GlyR L131M | α7GlyR Y115F L131M | α7GlyR L131N | α7GlyR L131Q | α7GlyR L131V | α75HT3 L131G HC | α75HT3 L131G Q139L Y217F HC | α7-GABAc L131G |
|---|---|---|---|---|---|---|---|---|---|---|
| Acetylcholine | 92 | 67 (3) | 29 | >500 (0.5) | 5 | 58 (5) | 16 | 35 | 39 | >500 |
| Nicotine | 20 (6.3) | 41(8) | 15 | nd | nd | 13 | 3.9 (0.7) | 15 | 20 | >500 |
| Epibatidine | 0.24 (0.05) | 0.022 (0.004) | 0.042 | nd | nd | 0.027 | 0.21 (0.04) | 0.009 | nd | |
| Varenicline | 2.6 (0.001) | 0.003 | 0.53 | >100 (0.027) | 0.069 | 0.72 (0.21) | 0.33 | 0.04 | 0.007 | 0.3 |
| Cytisine | 10.5 (1.8) | nd | 7 | nd | nd | >30 | 4.3 (0.7) | 11 | nd | >500 |
| PNU-282987 | 0.20 (0.01) | 0.05 | 0.021 | nd | nd | 0.048 (0.018) | 0.064 | 0.033 | 0.015 | 0.12 |
| Tropisetron | 0.39 (0.2) | 0.084 (0.009) | 0.024 | 0.035 | 0.025 (0.005) | 0.048 | 0.062 (0.013) | 0.066 | 0.04 | 0.18 |
| Nortropisetron | 0.027 (0.002) | 0.014 | 0.006 | nd | nd | 0.009 (0.001) | 0.003 | 0.009 | nd | 0.021 |
| PHA-543613 | 0.04 (0.007) | 0.015 (0.001) | 0.009 | 0.028 | 0.02 | 0.015 | 0.011 (0.002) | 0.012 | 0.009 | 0.027 |
| Granisetron | >100 | nd | 4 | nd | nd | 4 | 5.4 (1.3) | 4 | nd | >500 |
| 765 | nd | 0.034 (0.013) | nd | nd | >10 | nd | nd | nd | 0.11 | nd |
| 770 | 0.034 | 0.001 (0.0001) | 0.03 | nd | >10 | >0.3 | nd | nd | 0.007 | nd |
| 773 | 0.0005 | nd | 0.00005 | nd | 0.0004 | 0.006 | nd | nd | 0.002 | nd |
| 774 | 0.0013 | nd | 0.001 | nd | 0.0006 | 0.002 | nd | nd | 0.004 | nd | nd = not determined; parentheses: SEM

Example 7: Chimeric LGICs in Neurons

Figure 7:
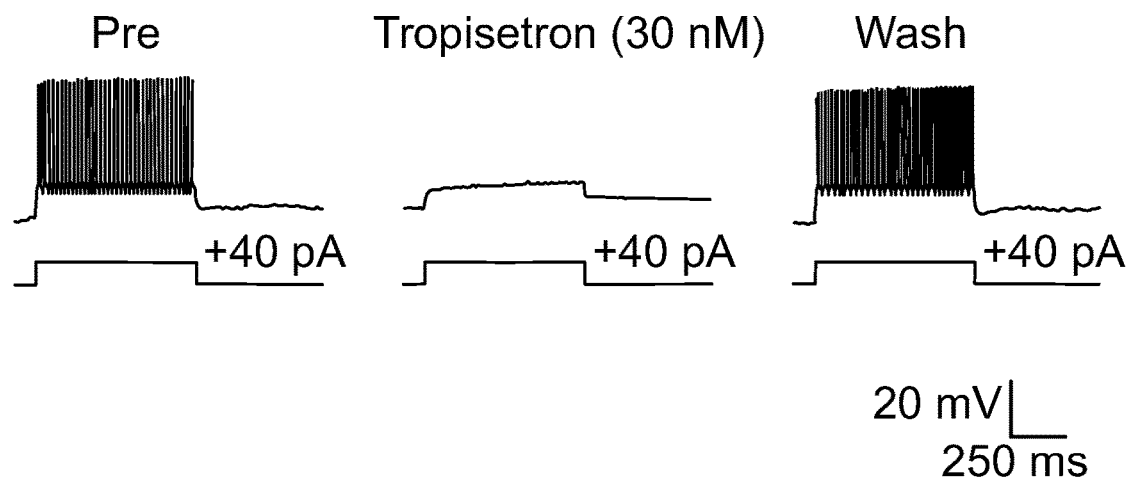
FIG. 7 shows that chimeric LGICs can be controlled using an exogenous ligand. Cortical neurons from a mouse brain transduced with α7$^{Q79G}$-GlyR$^{A298G}$ chimeric LGIC via adeno-associated virus (AAV) vectors fires action potentials in response to 40 pA current injection (PRE) that are potently suppressed by 30 nM tropisetron. After washout (WASH) of tropisetron, neuron firing is restored.
Figure 8A:
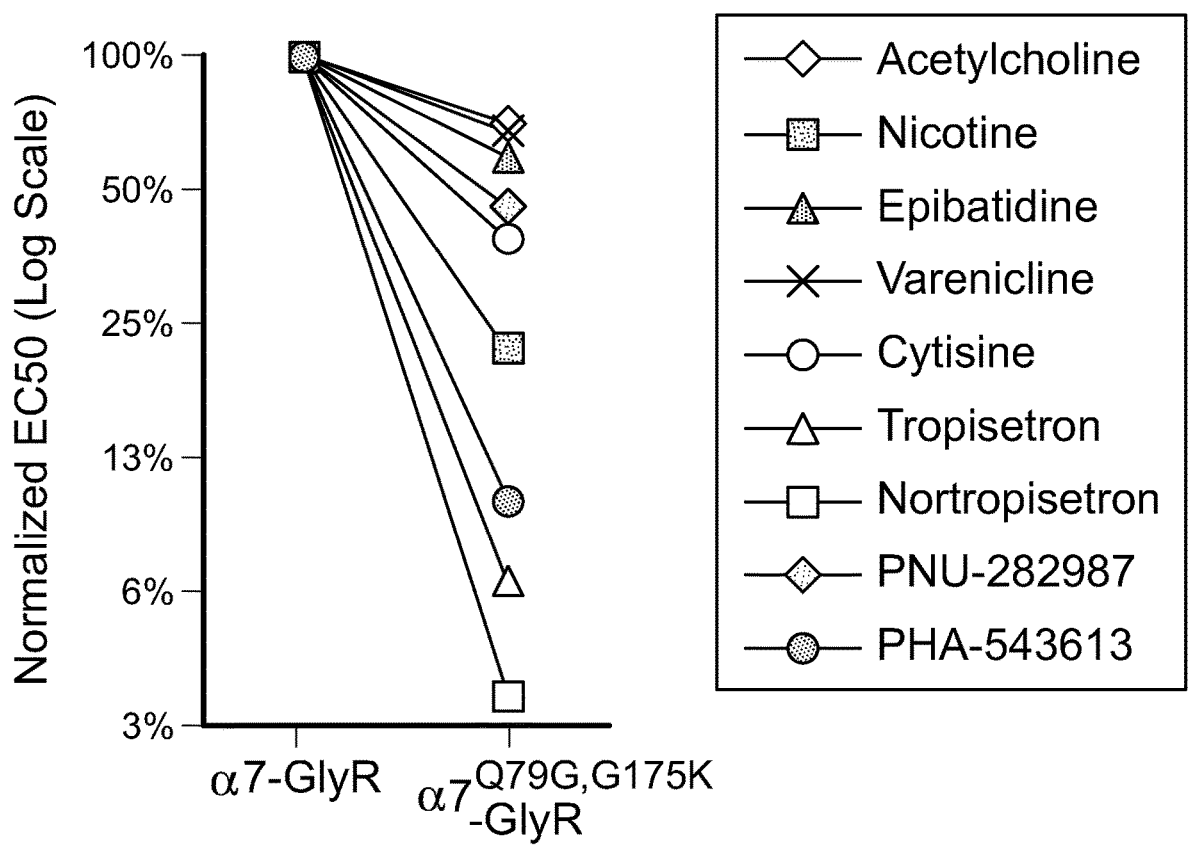
FIGS. 8A-8C show activity of agonists on chimeric LGICs with a G175K mutation.
Figure 8B:
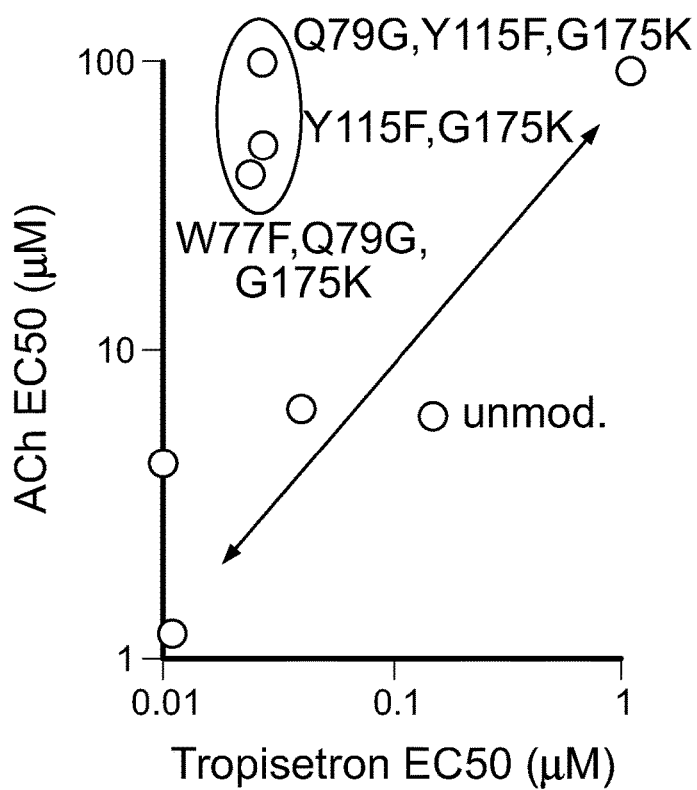
Figure 8C:
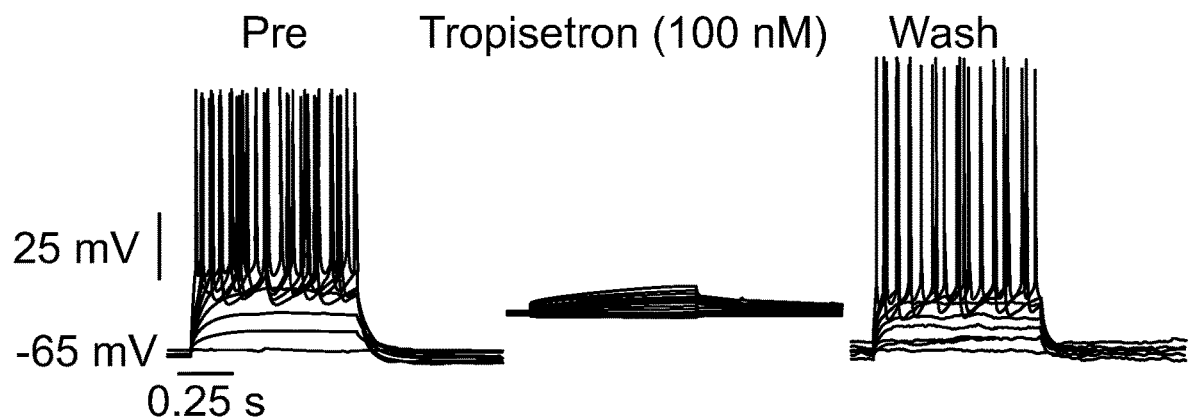

AAVs or DNA plasmids containing nucleic acids encoding a $\alpha7^{Q79G}$-GlyR$^{A298G}$ or $\alpha$7Q79G,Y115F,G175K-GlyR chimeric LGICs were transduced into mouse cortical neurons. A low concentration of tropisetron (30 nM or 100 nM) was administered to mouse cortical neurons. Neuron activity was silenced by application of low concentration of agonist (FIG. 7 and FIG. 8C).

Figure 9C:
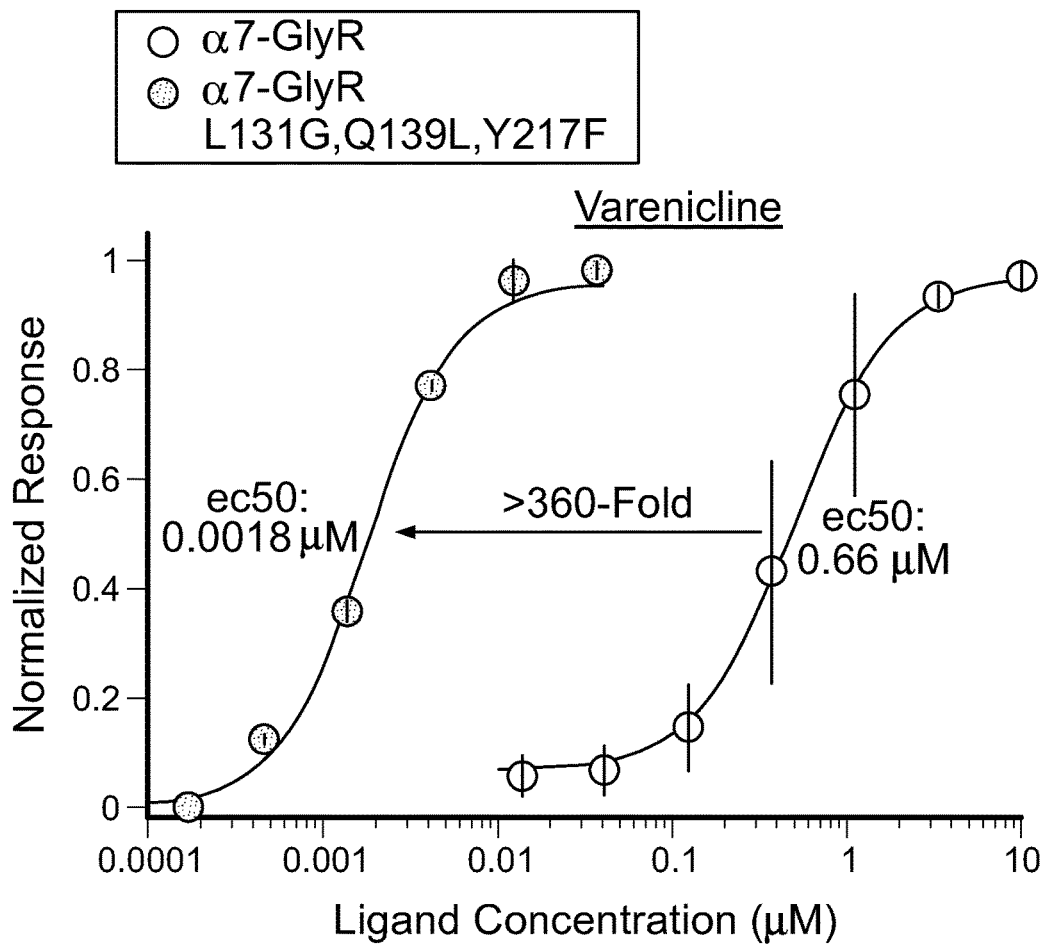
Figure 9D:
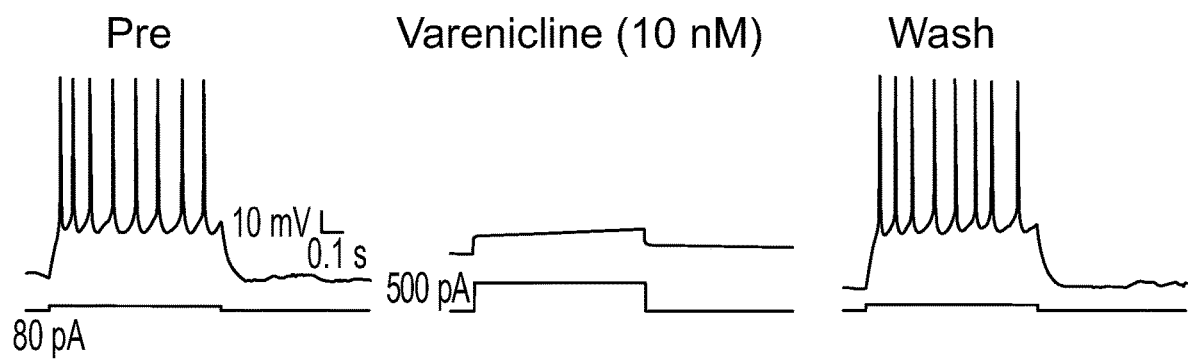
Figure 10A:
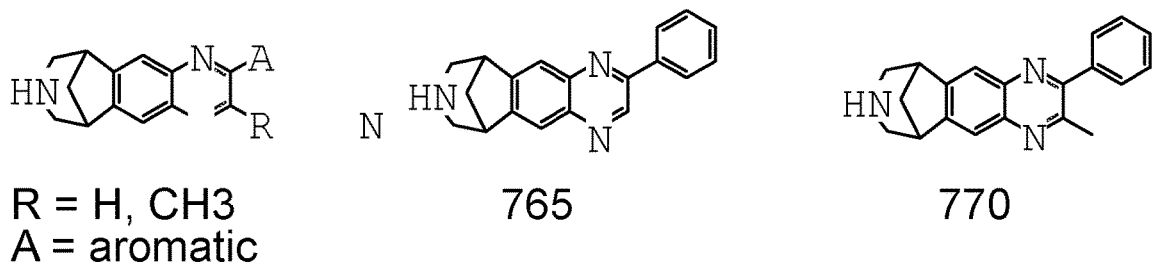
FIGS. 10A-10B show chemical structures of LGIC agonists.
Figure 10B:
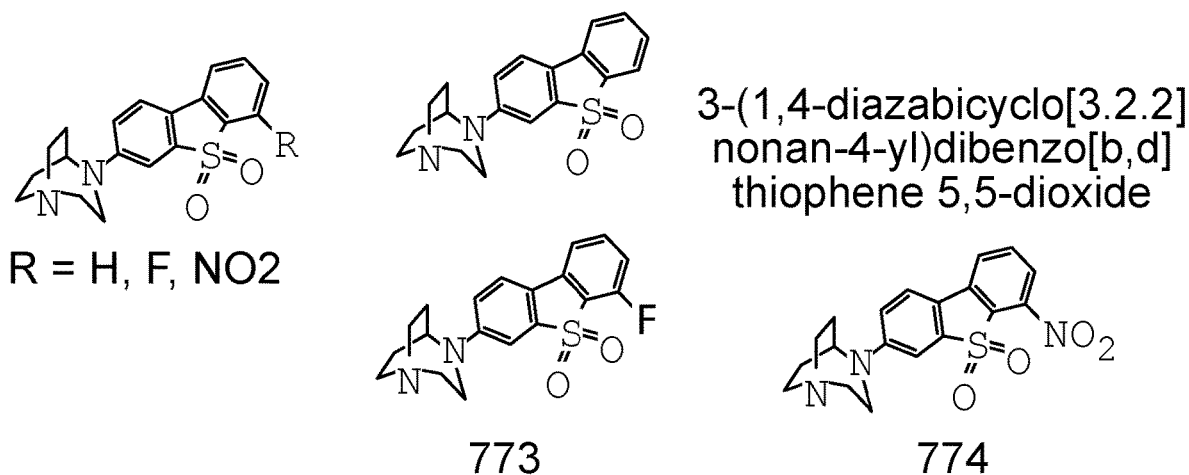

DNA plasmids containing nucleic acids encoding a $\alpha$7L131G,Q139L,Y217F-GlyR chimeric LGICs were transfected into mouse cortical neurons. Low concentration of varenicline (10 nM) was administered to mouse cortical neurons. Neuron activity was silenced by application of low concentration of agonist (FIG. 9C).

These results show that modified LGIC activity can be controlled in neurons using low concentration of the LGIC ligands tropisetron and varenicline.

Example 8: Chimeric LGICs in Therapy

Chemogenetic tools offer an attractive strategy for combined drug and gene therapy. This is because cellular function can be modulated in a consistent manner across different cell types in various indications using the same ion channels and ligands by use of an exogenously delivered ion channel that is selectively engaged by administration of a drug. Identification of ion channels that are gated by well tolerated, clinically used drugs are especially attractive for potentially extending chemogenetics to human therapeutic use.

For the drug tropisetron, we have found that it activates $\alpha7^{Q79G}$-GlyR$^{A298G}$ with an EC50 of 11 nM, which is similar to the reported IC50 of 10 nM tropisetron for its therapeutic target, the 5HT3 receptor (Combrink et al 2009 Pharmacological reports: PR 61: 785-97).

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A chimeric ligand gated ion channel (LGIC) receptor comprising at least one modified LGIC subunit, said modified LGIC subunit comprising:
   (a) a human alpha7 nicotinic acetylcholine receptor (α7-nAChR) ligand binding domain (LBD) comprising a Cys-loop domain, wherein said Cys-loop domain comprises amino acids 150-164 as numbered in SEQ ID NO:2, and
   (b) a human glycine receptor (GlyR) ion pore domain (IPD).

2. The chimeric LGIC receptor of claim 1, wherein the α7 nAChR LBD comprises a sequence having at least 93 percent sequence identity to a sequence set forth in SEQ ID NO:2.

3. The chimeric LGIC receptor of claim 2, wherein the α7-nAChR LBD comprises an amino acid substitution at amino acid residue L131 as numbered in SEQ ID NO:2.

4. The chimeric LGIC receptor of claim 2, wherein the modified LGIC subunit comprises a sequence having at least 93 percent sequence identity to SEQ ID NO:7.

5. The chimeric LGIC receptor of claim 2, wherein the α7-nAChR LBD comprises an amino acid substitution at one or more of amino acid residues W77, Q79, Y115, L131, Q139, L141, Y210, and Y217 as numbered in SEQ ID NO:2.

6. The chimeric LGIC receptor of claim 5, wherein the amino acid substitution at residue W77 is W77F, W77Y, or W77IM; wherein the amino acid substitution at residue Q79 is Q79A, Q79G, or Q79S; wherein the amino acid substitution at residue Y115 is Y115F; wherein amino acid substitution at residue L131 is L131G, L131A, L131M, L131N, L131Q, L131V, or L131F; wherein the amino acid substitution at residue Q139 is Q139G or Q139L; wherein the amino acid substitution at residue L141 is L141F or L141P; wherein the amino acid substitution at residue Y210 is Y210F; and wherein the amino acid substitution at residue Y217 is Y217F.

7. The chimeric LGIC receptor of claim 1, wherein an exogenous LGIC ligand activates the chimeric LGIC receptor, and wherein the exogenous LGIC ligand is a synthetic exogenous LGIC ligand selected from the group consisting of a quinuclidine, a tropane, a 9-azabicyclo[3.3.1]nonane, varenicline, and a 1,4-diazabicyclo[3.2.2]nonane.

* * * * *

SEQUENCE LISTING

<160> NUMBER OF SEQ ID NOS: 12

<210> SEQ ID NO 1
<211> LENGTH: 224
<212> TYPE: PRT
<213> ORGANISM: human

<400> SEQUENCE: 1

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

<210> SEQ ID NO 2
<211> LENGTH: 229
<212> TYPE: PRT
<213> ORGANISM: human

<400> SEQUENCE: 2

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile

```
            100                 105                 110
Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg
225

<210> SEQ ID NO 3
<211> LENGTH: 247
<212> TYPE: PRT
<213> ORGANISM: mouse

<400> SEQUENCE: 3

Ile Ile Arg Arg Arg Pro Leu Phe Tyr Ala Val Ser Leu Leu Leu Pro
1               5                   10                  15

Ser Ile Phe Leu Met Val Val Asp Ile Val Gly Phe Cys Leu Pro Pro
                20                  25                  30

Asp Ser Gly Glu Arg Val Ser Phe Lys Ile Thr Leu Leu Leu Gly Tyr
            35                  40                  45

Ser Val Phe Leu Ile Ile Val Ser Asp Thr Leu Pro Ala Thr Ile Gly
        50                  55                  60

Thr Pro Leu Ile Gly Val Tyr Phe Val Val Cys Met Ala Leu Leu Val
65                  70                  75                  80

Ile Ser Leu Ala Glu Thr Ile Phe Ile Val Arg Leu Val His Lys Gln
                85                  90                  95

Asp Leu Gln Arg Pro Val Pro Asp Trp Leu Arg His Leu Val Leu Asp
                100                 105                 110

Arg Ile Ala Trp Ile Leu Cys Leu Gly Glu Gln Pro Met Ala His Arg
            115                 120                 125

Pro Pro Ala Thr Phe Gln Ala Asn Lys Thr Asp Asp Cys Ser Gly Ser
        130                 135                 140

Asp Leu Leu Pro Ala Met Gly Asn His Cys Ser His Val Gly Gly Pro
145                 150                 155                 160

Gln Asp Leu Glu Lys Thr Pro Arg Gly Arg Gly Ser Pro Leu Pro Pro
                165                 170                 175

Pro Arg Glu Ala Ser Leu Ala Val Arg Gly Leu Leu Gln Glu Leu Ser
            180                 185                 190

Ser Ile Arg His Phe Leu Glu Lys Arg Asp Glu Met Arg Glu Val Ala
        195                 200                 205

Arg Asp Trp Leu Arg Val Gly Tyr Val Leu Asp Arg Leu Leu Phe Arg
210                 215                 220

Ile Tyr Leu Leu Ala Val Leu Ala Tyr Ser Ile Thr Leu Val Thr Leu
225                 230                 235                 240
```

Trp Ser Ile Trp His Tyr Ser
                245

<210> SEQ ID NO 4
<211> LENGTH: 241
<212> TYPE: PRT
<213> ORGANISM: human

<400> SEQUENCE: 4

Ile Ile Arg Arg Arg Leu Phe Tyr Val Val Ser Leu Leu Pro Ser
1               5                   10                  15

Ile Phe Leu Met Val Met Asp Ile Val Gly Phe Tyr Leu Pro Pro Asn
                20                  25                  30

Ser Gly Glu Arg Val Ser Phe Lys Ile Thr Leu Leu Leu Gly Tyr Ser
            35                  40                  45

Val Phe Leu Ile Ile Val Ser Asp Thr Leu Pro Ala Thr Ala Ile Gly
    50                  55                  60

Thr Pro Leu Ile Gly Val Tyr Phe Val Val Cys Met Ala Leu Leu Val
65                  70                  75                  80

Ile Ser Leu Ala Glu Thr Ile Phe Ile Val Arg Leu Val His Lys Gln
                85                  90                  95

Asp Leu Gln Gln Pro Val Pro Ala Trp Leu Arg His Leu Val Leu Glu
            100                 105                 110

Arg Ile Ala Trp Leu Leu Cys Leu Arg Glu Gln Ser Thr Ser Gln Arg
        115                 120                 125

Pro Pro Ala Thr Ser Gln Ala Thr Lys Thr Asp Asp Cys Ser Ala Met
    130                 135                 140

Gly Asn His Cys Ser His Met Gly Gly Pro Gln Asp Phe Glu Lys Ser
145                 150                 155                 160

Pro Arg Asp Arg Cys Ser Pro Pro Pro Arg Glu Ala Ser Leu
                165                 170                 175

Ala Val Cys Gly Leu Leu Gln Glu Leu Ser Ser Ile Arg Gln Phe Leu
            180                 185                 190

Glu Lys Arg Asp Glu Ile Arg Glu Val Ala Arg Asp Trp Leu Arg Val
        195                 200                 205

Gly Ser Val Leu Asp Lys Leu Leu Phe His Ile Tyr Leu Leu Ala Val
    210                 215                 220

Leu Ala Tyr Ser Ile Thr Leu Val Met Leu Trp Ser Ile Trp Gln Tyr
225                 230                 235                 240

Ala

<210> SEQ ID NO 5
<211> LENGTH: 202
<212> TYPE: PRT
<213> ORGANISM: mouse

<400> SEQUENCE: 5

Met Gly Tyr Tyr Leu Ile Gln Met Tyr Ile Pro Ser Leu Leu Ile Val
1               5                   10                  15

Ile Leu Ser Trp Ile Ser Phe Trp Ile Asn Met Asp Ala Ala Pro Ala
                20                  25                  30

Arg Val Gly Leu Gly Ile Thr Thr Val Leu Thr Met Thr Thr Gln Ser
            35                  40                  45

Ser Gly Ser Arg Ala Ser Leu Pro Lys Val Ser Tyr Val Lys Ala Ile
    50                  55                  60

Asp Ile Trp Met Ala Val Cys Leu Leu Phe Val Phe Ser Ala Leu Leu

```
            65                  70                  75                  80
        Glu Tyr Ala Ala Val Asn Phe Val Ser Arg Gln His Lys Glu Leu Leu
                        85                  90                  95

Arg Phe Arg Arg Lys Arg Arg His His Lys Glu Asp Glu Ala Gly Glu
                        100                 105                 110

Gly Arg Phe Asn Phe Ser Ala Tyr Gly Met Gly Pro Ala Cys Leu Gln
                        115                 120                 125

Ala Lys Asp Gly Ile Ser Val Lys Gly Ala Asn Asn Ser Asn Thr Thr
                        130                 135                 140

Asn Pro Pro Ala Pro Ser Lys Ser Pro Glu Glu Met Arg Lys Leu
        145                 150                 155                 160

Phe Ile Gln Arg Ala Lys Lys Ile Asp Lys Ile Ser Arg Ile Gly Phe
                        165                 170                 175

Pro Met Ala Phe Leu Ile Phe Asn Met Phe Tyr Trp Ile Ile Tyr Lys
                        180                 185                 190

Ile Val Arg Arg Glu Asp Val His Asn Gln
                        195                 200

<210> SEQ ID NO 6
<211> LENGTH: 471
<212> TYPE: PRT
<213> ORGANISM: artificial
<220> FEATURE:
<223> OTHER INFORMATION: (alpha)7-5HT3 chimeric receptor

<400> SEQUENCE: 6

Met Arg Cys Ser Pro Gly Gly Val Trp Leu Ala Leu Ala Ala Ser Leu
        1               5                   10                  15

Leu His Val Ser Leu Gln Gly Glu Phe Gln Arg Lys Leu Tyr Lys Glu
                        20                  25                  30

Leu Val Lys Asn Tyr Asn Pro Leu Glu Arg Pro Val Ala Asn Asp Ser
                        35                  40                  45

Gln Pro Leu Thr Val Tyr Phe Ser Leu Ser Leu Gln Ile Met Asp
                        50                  55                  60

Val Asp Glu Lys Asn Gln Val Leu Thr Thr Asn Ile Trp Leu Gln Met
        65                  70                  75                  80

Ser Trp Thr Asp His Tyr Leu Gln Trp Asn Val Ser Glu Tyr Pro Gly
                        85                  90                  95

Val Lys Thr Val Arg Phe Pro Asp Gly Gln Ile Trp Lys Pro Asp Ile
                        100                 105                 110

Leu Leu Tyr Asn Ser Ala Asp Glu Arg Phe Asp Ala Thr Phe His Thr
                        115                 120                 125

Asn Val Leu Val Asn Ser Ser Gly His Cys Gln Tyr Leu Pro Pro Gly
                        130                 135                 140

Ile Phe Lys Ser Ser Cys Tyr Ile Asp Val Arg Trp Phe Pro Phe Asp
        145                 150                 155                 160

Val Gln His Cys Lys Leu Lys Phe Gly Ser Trp Ser Tyr Gly Gly Trp
                        165                 170                 175

Ser Leu Asp Leu Gln Met Gln Glu Ala Asp Ile Ser Gly Tyr Ile Pro
                        180                 185                 190

Asn Gly Glu Trp Asp Leu Val Gly Ile Pro Gly Lys Arg Ser Glu Arg
                        195                 200                 205

Phe Tyr Glu Cys Cys Lys Glu Pro Tyr Pro Asp Val Thr Phe Thr Val
                        210                 215                 220

Ile Ile Arg Arg Arg Pro Leu Phe Tyr Ala Val Ser Leu Leu Leu Pro
```

```
225                 230                 235                 240
Ser Ile Phe Leu Met Val Val Asp Ile Val Gly Phe Cys Leu Pro Pro
                245                 250                 255

Asp Ser Gly Glu Arg Val Ser Phe Lys Ile Thr Leu Leu Gly Tyr
            260                 265                 270

Ser Val Phe Leu Ile Ile Val Ser Asp Thr Leu Pro Ala Thr Ile Gly
            275                 280                 285

Thr Pro Leu Ile Gly Val Tyr Phe Val Val Cys Met Ala Leu Leu Val
            290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335

Arg Ile Ala Trp Ile Leu Cys Leu Gly Glu Gln Pro Met Ala His Arg
                340                 345                 350

Pro Pro Ala Thr Phe Gln Ala Asn Lys Thr Asp Asp Cys Ser Gly Ser
            355                 360                 365

Asp Leu Leu Pro Ala Met Gly Asn His Cys Ser His Val Gly Gly Pro
370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
                405                 410                 415

Ser Ile Arg His Phe Leu Glu Lys Arg Asp Glu Met Arg Glu Val Ala
                420                 425                 430

Arg Asp Trp Leu Arg Val Gly Tyr Val Leu Asp Arg Leu Leu Phe Arg
                435                 440                 445

Ile Tyr Leu Leu Ala Val Leu Ala Tyr Ser Ile Thr Leu Val Thr Leu
            450                 455                 460

Trp Ser Ile Trp His Tyr Ser
465                 470

<210> SEQ ID NO 7
<211> LENGTH: 431
<212> TYPE: PRT
<213> ORGANISM: artificial
<220> FEATURE:
<223> OTHER INFORMATION: (alpha)7-GlyR chimeric receptor

<400> SEQUENCE: 7

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
```

```
            115                 120                 125
Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Glu
                325                 330                 335

Asp Glu Ala Gly Glu Gly Arg Phe Asn Phe Ser Ala Tyr Gly Met Gly
            340                 345                 350

Pro Ala Cys Leu Gln Ala Lys Asp Gly Ile Ser Val Lys Gly Ala Asn
        355                 360                 365

Asn Ser Asn Thr Thr Asn Pro Pro Ala Pro Ser Lys Ser Pro Glu
        370                 375                 380

Glu Met Arg Lys Leu Phe Ile Gln Arg Ala Lys Lys Ile Asp Lys Ile
385                 390                 395                 400

Ser Arg Ile Gly Phe Pro Met Ala Phe Leu Ile Phe Asn Met Phe Tyr
                405                 410                 415

Trp Ile Ile Tyr Lys Ile Val Arg Arg Glu Asp Val His Asn Gln
            420                 425                 430

<210> SEQ ID NO 8
<211> LENGTH: 466
<212> TYPE: PRT
<213> ORGANISM: artificial
<220> FEATURE:
<223> OTHER INFORMATION: (alpha)7-5HT3 chimeric receptor

<400> SEQUENCE: 8

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
```

```
                50                  55                  60
Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
                115                 120                 125

Asn Val Leu Val Asn Ser Ser Gly His Cys Gln Tyr Leu Pro Pro Gly
                130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
                195                 200                 205

Phe Tyr Glu Cys Cys Lys Glu Pro Tyr Pro Asp Val Thr Phe Thr Val
                210                 215                 220

Ile Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
                260                 265                 270

Ser Val Phe Leu Ile Ile Val Ser Asp Thr Leu Pro Ala Thr Ala Ile
                275                 280                 285

Gly Thr Pro Leu Ile Gly Val Tyr Phe Val Val Cys Met Ala Leu Leu
                290                 295                 300

Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
                325                 330                 335

Glu Arg Ile Ala Trp Leu Leu Cys Leu Arg Glu Gln Ser Thr Ser Gln
                340                 345                 350

Arg Pro Pro Ala Thr Ser Gln Ala Thr Lys Thr Asp Asp Cys Ser Ala
                355                 360                 365

Met Gly Asn His Cys Ser His Met Gly Gly Pro Gln Asp Phe Glu Lys
                370                 375                 380

Ser Pro Arg Asp Arg Cys Ser Pro Pro Pro Pro Arg Glu Ala Ser
385                 390                 395                 400

Leu Ala Val Cys Gly Leu Leu Gln Glu Leu Ser Ser Ile Arg Gln Phe
                405                 410                 415

Leu Glu Lys Arg Asp Glu Ile Arg Glu Val Ala Arg Asp Trp Leu Arg
                420                 425                 430

Val Gly Ser Val Leu Asp Lys Leu Leu Phe His Ile Tyr Leu Leu Ala
                435                 440                 445

Val Leu Ala Tyr Ser Ile Thr Leu Val Met Leu Trp Ser Ile Trp Gln
450                 455                 460

Tyr Ala
465
```

<210> SEQ ID NO 9
<211> LENGTH: 195
<212> TYPE: PRT
<213> ORGANISM: human

<400> SEQUENCE: 9

```
Leu Leu Gln Thr Tyr Phe Pro Ala Thr Leu Met Val Met Leu Ser Trp
1               5                   10                  15

Val Ser Phe Trp Ile Asp Arg Arg Ala Val Pro Ala Arg Val Pro Leu
            20                  25                  30

Gly Ile Thr Thr Val Leu Thr Met Ser Thr Ile Ile Thr Gly Val Asn
        35                  40                  45

Ala Ser Met Pro Arg Val Ser Tyr Ile Lys Ala Val Asp Ile Tyr Leu
    50                  55                  60

Trp Val Ser Phe Val Phe Val Phe Leu Ser Val Leu Glu Tyr Ala Ala
65                  70                  75                  80

Val Asn Tyr Leu Thr Thr Val Gln Glu Arg Lys Glu Gln Lys Leu Arg
                85                  90                  95

Glu Lys Leu Pro Cys Thr Ser Gly Leu Pro Pro Arg Thr Ala Met
            100                 105                 110

Leu Asp Gly Asn Tyr Ser Asp Gly Glu Val Asn Asp Leu Asp Asn Tyr
        115                 120                 125

Met Pro Glu Asn Gly Glu Lys Pro Asp Arg Met Met Val Gln Leu Thr
    130                 135                 140

Leu Ala Ser Glu Arg Ser Ser Pro Gln Arg Lys Ser Gln Arg Ser Ser
145                 150                 155                 160

Tyr Val Ser Met Arg Ile Asp Thr His Ala Ile Asp Lys Tyr Ser Arg
                165                 170                 175

Ile Ile Phe Pro Ala Ala Tyr Ile Leu Phe Asn Leu Ile Tyr Trp Ser
            180                 185                 190

Ile Phe Ser
        195
```

<210> SEQ ID NO 10
<211> LENGTH: 428
<212> TYPE: PRT
<213> ORGANISM: artificial
<220> FEATURE:
<223> OTHER INFORMATION: (alpha)7- GABAC chimeric receptor

<400> SEQUENCE: 10

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110
```

```
Leu Leu Tyr Asn Ser Ala Asp Glu Arg Phe Asp Ala Thr Phe His Thr
            115                 120                 125
Asn Val Leu Val Asn Ser Gly His Cys Gln Tyr Leu Pro Pro Gly
    130                 135                 140
Ile Phe Lys Ser Ser Cys Tyr Ile Asp Val Arg Trp Phe Pro Phe Asp
145                 150                 155                 160
Val Gln His Cys Lys Leu Lys Phe Gly Ser Trp Ser Tyr Gly Gly Trp
                165                 170                 175
Ser Leu Asp Leu Gln Met Gln Glu Ala Asp Ile Ser Gly Tyr Ile Pro
            180                 185                 190
Asn Gly Glu Trp Asp Leu Val Gly Ile Pro Gly Lys Arg Ser Glu Arg
        195                 200                 205
Phe Tyr Glu Cys Cys Lys Glu Pro Tyr Pro Asp Val Thr Phe Thr Val
    210                 215                 220
Thr Met Arg Arg Arg Thr Leu Tyr Tyr Leu Leu Gln Thr Tyr Phe Pro
225                 230                 235                 240
Ala Thr Leu Met Val Met Leu Ser Trp Val Ser Phe Trp Ile Asp Arg
                245                 250                 255
Arg Ala Val Pro Ala Arg Val Pro Leu Gly Ile Thr Thr Val Leu Thr
            260                 265                 270
Met Ser Thr Ile Ile Thr Gly Val Asn Ala Ser Met Pro Arg Val Ser
        275                 280                 285
Tyr Ile Lys Ala Val Asp Ile Tyr Leu Trp Val Ser Phe Val Phe Val
    290                 295                 300
Phe Leu Ser Val Leu Glu Tyr Ala Ala Val Asn Tyr Leu Thr Thr Val
305                 310                 315                 320
Gln Glu Arg Lys Glu Gln Lys Leu Arg Glu Lys Leu Pro Cys Thr Ser
                325                 330                 335
Gly Leu Pro Pro Arg Thr Ala Met Leu Asp Gly Asn Tyr Ser Asp
            340                 345                 350
Gly Glu Val Asn Asp Leu Asp Asn Tyr Met Pro Glu Asn Gly Glu Lys
        355                 360                 365
Pro Asp Arg Met Met Val Gln Leu Thr Leu Ala Ser Glu Arg Ser Ser
    370                 375                 380
Pro Gln Arg Lys Ser Gln Arg Ser Ser Tyr Val Ser Met Arg Ile Asp
385                 390                 395                 400
Thr His Ala Ile Asp Lys Tyr Ser Arg Ile Ile Phe Pro Ala Ala Tyr
                405                 410                 415
Ile Leu Phe Asn Leu Ile Tyr Trp Ser Ile Phe Ser
            420                 425

<210> SEQ ID NO 11
<211> LENGTH: 233
<212> TYPE: PRT
<213> ORGANISM: human

<400> SEQUENCE: 11

Met Arg Cys Ser Pro Gly Gly Val Trp Leu Ala Leu Ala Ala Ser Leu
1               5                   10                  15
Leu His Val Ser Leu Gln Gly Glu Phe Gln Arg Lys Leu Tyr Lys Glu
                20                  25                  30
Leu Val Lys Asn Tyr Asn Pro Leu Glu Arg Pro Val Ala Asn Asp Ser
            35                  40                  45
Gln Pro Leu Thr Val Tyr Phe Ser Leu Ser Leu Leu Gln Ile Met Asp
        50                  55                  60
```

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
210                 215                 220

Thr Met Arg Arg Arg Thr Leu Tyr Tyr
225                 230

<210> SEQ ID NO 12
<211> LENGTH: 502
<212> TYPE: PRT
<213> ORGANISM: rat

<400> SEQUENCE: 12

Met Gly Gly Gly Arg Gly Gly Ile Trp Leu Ala Leu Ala Ala Ala Leu
1               5                   10                  15

Leu His Val Ser Leu Gln Gly Glu Phe Gln Arg Arg Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Met Ser Glu Tyr Pro Gly
                85                  90                  95

Val Lys Asn Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ala Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln Gln Cys Lys Leu Lys Phe Gly Ser Trp Ser Tyr Gly Gly Trp
                165                 170                 175

Ser Leu Asp Leu Gln Met Gln Glu Ala Asp Ile Ser Ser Tyr Ile Pro
            180                 185                 190

Asn Gly Glu Trp Asp Leu Met Gly Ile Pro Gly Lys Arg Asn Glu Lys

```
                    195                 200                 205
Phe Tyr Glu Cys Cys Lys Glu Pro Tyr Pro Asp Val Thr Tyr Thr Val
    210                 215                 220

Thr Met Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                    245                 250                 255

Asp Ser Gly Glu Lys Ile Ser Leu Gly Ile Thr Val Leu Leu Ser Leu
                260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
    290                 295                 300

Gly Leu Ser Val Val Thr Val Ile Val Leu Arg Tyr His His His
305                 310                 315                 320

Asp Pro Asp Gly Gly Lys Met Pro Lys Trp Thr Arg Ile Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Pro Arg Arg Cys Ser Leu Ala Ser
                355                 360                 365

Val Glu Leu Ser Ala Gly Ala Gly Pro Pro Thr Ser Asn Gly Asn Leu
    370                 375                 380

Leu Tyr Ile Gly Phe Arg Gly Leu Glu Gly Met His Cys Ala Pro Thr
385                 390                 395                 400

Pro Asp Ser Gly Val Val Cys Gly Arg Leu Ala Cys Ser Pro Thr His
                    405                 410                 415

Asp Glu His Leu Met His Gly Ala His Pro Ser Asp Gly Asp Pro Asp
                420                 425                 430

Leu Ala Lys Ile Leu Glu Glu Val Arg Tyr Ile Ala Asn Arg Asn Arg
                435                 440                 445

Cys Gln Asp Glu Ser Glu Val Ile Cys Ser Glu Trp Lys Phe Ala Ala
    450                 455                 460

Cys Val Val Asp Pro Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
                500
```